United States Patent
McWeeney et al.

(10) Patent No.: US 7,922,650 B2
(45) Date of Patent: Apr. 12, 2011

(54) MEDICAL VISUALIZATION SYSTEM WITH ENDOSCOPE AND MOUNTED CATHETER

(75) Inventors: John O. McWeeney, Brighton, MA (US); Benjamin E. Morris, Louisville, KY (US); David W. Robertson, Framingham, MA (US); David I. Freed, Westborough, MA (US); James F. Schuermann, Natick, MA (US); John B. Golden, Norton, MA (US); Jozef Slanda, Milford, MA (US); Brian Keith Wells, LaGrange, KY (US); Jesse Leonard Farris, III, Andover, MA (US); Michael S. H. Chu, Brookline, MA (US); Oscar R. Carrillo, Jr., Attleboro, MA (US); Todd A. Hall, Goshen, KY (US); Yem Chin, Burlington, MA (US); Mark L. Adams, Sandy, UT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1169 days.

(21) Appl. No.: 11/089,520

(22) Filed: Mar. 23, 2005

(65) Prior Publication Data

US 2005/0272975 A1 Dec. 8, 2005

Related U.S. Application Data

(63) Continuation-in-part of application No. 10/914,411, filed on Aug. 9, 2004.

(60) Provisional application No. 60/555,356, filed on Mar. 23, 2004, provisional application No. 60/656,801, filed on Feb. 25, 2005.

(51) Int. Cl.
*A61B 1/00* (2006.01)

(52) U.S. Cl. ......... 600/104; 600/160; 600/172; 600/182
(58) Field of Classification Search ............... 600/104, 600/109, 153, 160, 173, 182, 113–115, 120–123, 600/130, 172, 175
See application file for complete search history.

(56) References Cited

U.S. PATENT DOCUMENTS 3,886,933 A * 6/1975 Mori et al. ................ 600/135
(Continued)

FOREIGN PATENT DOCUMENTS

EP 0 815 895 A1 1/1998
(Continued)

OTHER PUBLICATIONS

A communication from the Japanese Patent Office citing the above Japanese Patents in Patent Application No. 2007-505103, mailed Nov. 10, 2009.

(Continued)

*Primary Examiner* — John P Leubecker
*Assistant Examiner* — Victoria W Chen
(74) *Attorney, Agent, or Firm* — Finnegan Henderson, Farabow, Garrett & Dunner, LLP

(57) ABSTRACT

The present invention is directed to features and aspects of an in-vivo visualization system that comprises a catheter having an access port leading to an interior lumen through which an image transmission member is routed, and an endoscope having an access port leading to an interior lumen through which the catheter is routed. The catheter and endoscope are connected by an endoscope attachment device such that a handle of the catheter is mounted distal of the endoscope access port and the catheter access port is distal to the mounted position.

17 Claims, 49 Drawing Sheets

U.S. PATENT DOCUMENTS

| | | | | |
|---|---|---|---|---|
| 4,586,491 | A | * | 5/1986 | Carpenter .................... 600/113 |
| 4,802,461 | A | | 2/1989 | Cho |
| 4,807,595 | A | * | 2/1989 | Hiltebrandt .................. 600/104 |
| 4,905,667 | A | * | 3/1990 | Foerster et al. .............. 600/104 |
| 4,911,148 | A | | 3/1990 | Sosnowski et al. |
| 4,979,496 | A | * | 12/1990 | Komi ............................ 600/113 |
| 5,114,402 | A | | 5/1992 | McCoy |
| 5,178,130 | A | * | 1/1993 | Kaiya .......................... 600/109 |
| 5,403,311 | A | * | 4/1995 | Abele et al. ................... 606/49 |
| 5,733,242 | A | | 3/1998 | Rayburn et al. |
| 5,803,898 | A | | 9/1998 | Bashour |
| 5,860,914 | A | | 1/1999 | Chiba et al. |
| 5,879,287 | A | * | 3/1999 | Yoshihashi ................... 600/160 |
| 5,993,447 | A | * | 11/1999 | Blewett et al. ................. 606/50 |
| 6,007,531 | A | | 12/1999 | Snoke et al. |
| 6,096,009 | A | * | 8/2000 | Windheuser et al. ..... 604/165.01 |
| 6,296,608 | B1 | * | 10/2001 | Daniels et al. ................ 600/104 |
| 6,328,730 | B1 | * | 12/2001 | Harkrider, Jr. ................ 604/523 |
| 6,589,163 | B2 | | 7/2003 | Aizawa et al. |
| 7,198,599 | B2 | | 4/2007 | Goto et al. |
| 7,232,434 | B2 | | 6/2007 | Suyama et al. |
| 2002/0026188 | A1 | | 2/2002 | Balbierz et al. |
| 2002/0115983 | A1 | | 8/2002 | Sekino et al. |
| 2002/0188285 | A1 | | 12/2002 | Brown |
| 2003/0004460 | A1 | | 1/2003 | Bedell |
| 2003/0028200 | A1 | * | 2/2003 | Berg et al. ..................... 606/108 |
| 2004/0015050 | A1 | * | 1/2004 | Goto et al. ..................... 600/104 |
| 2004/0116800 | A1 | | 6/2004 | Helfer et al. |
| 2005/0165288 | A1 | * | 7/2005 | Rioux et al. ................... 600/342 |
| 2010/0198009 | A1 | | 8/2010 | Farr et al. |

FOREIGN PATENT DOCUMENTS

| | | |
|---|---|---|
| JP | 04-354926 | 12/1992 |
| JP | 3004466 | 9/1994 |
| JP | 2000-121962 | 4/2000 |
| JP | 2000-157486 | 6/2000 |
| JP | 2002-521114 | 7/2002 |
| JP | 2002-272675 | 9/2002 |
| JP | 2004-49891 | 2/2004 |
| JP | 2004-503339 | 2/2004 |
| WO | WO 97/29679 A | 8/1997 |
| WO | WO 00/06013 | 2/2000 |
| WO | WO 02/05885 | 1/2002 |

OTHER PUBLICATIONS

An English language version of a communication from the Japanese Patent Office citing the above Japanese Patents in Patent Application No. 2007-505103, mailed Mar. 29, 2010.

* cited by examiner

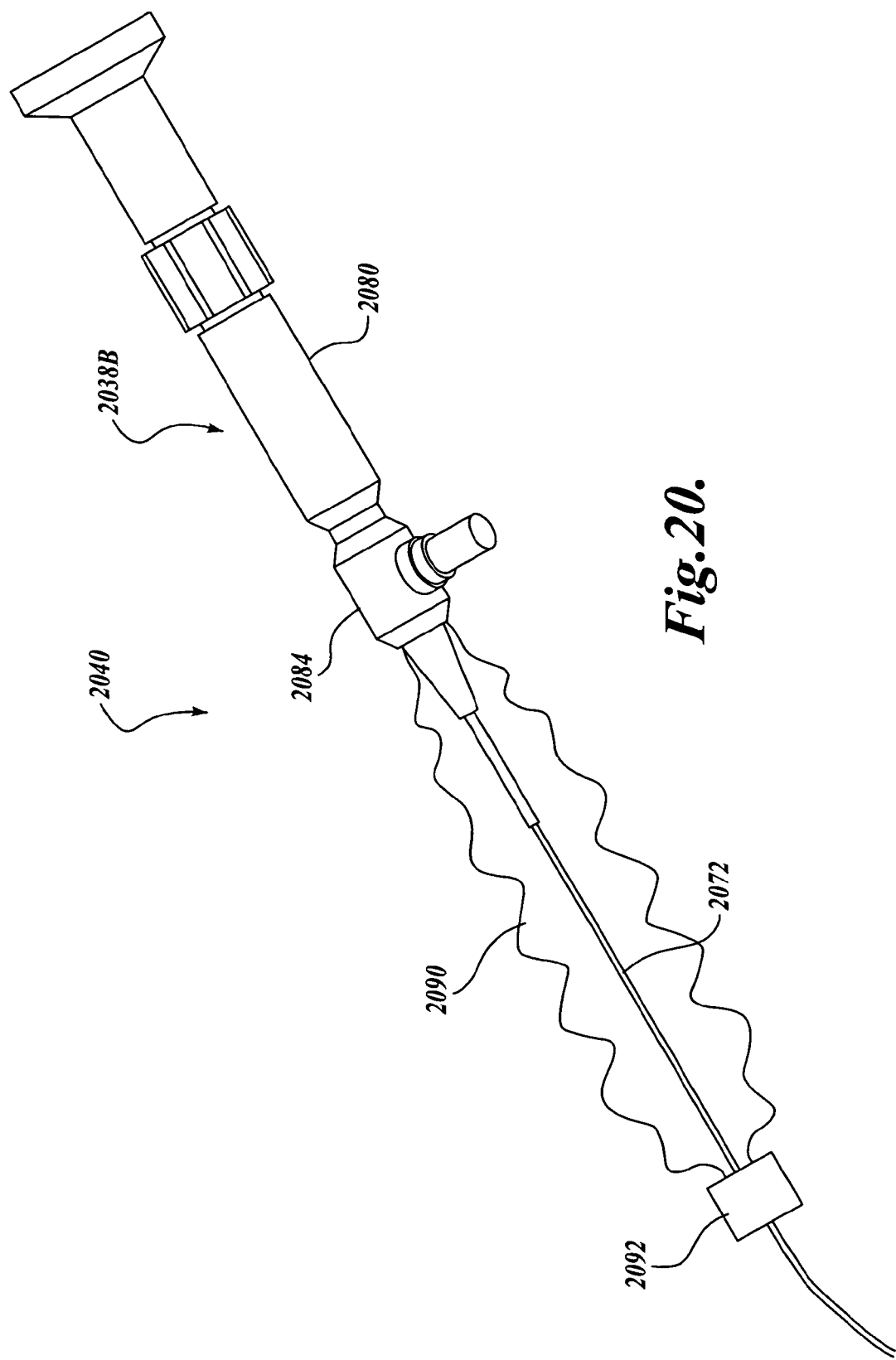

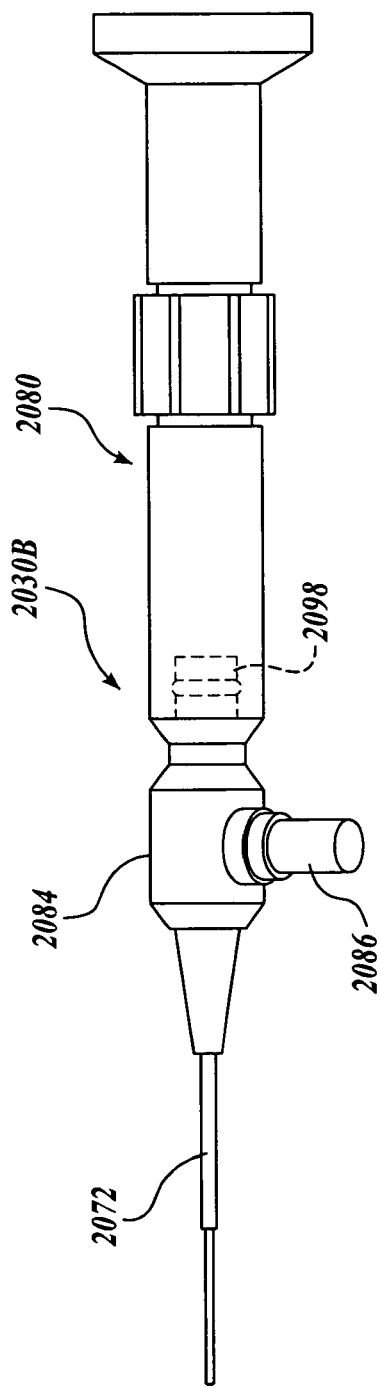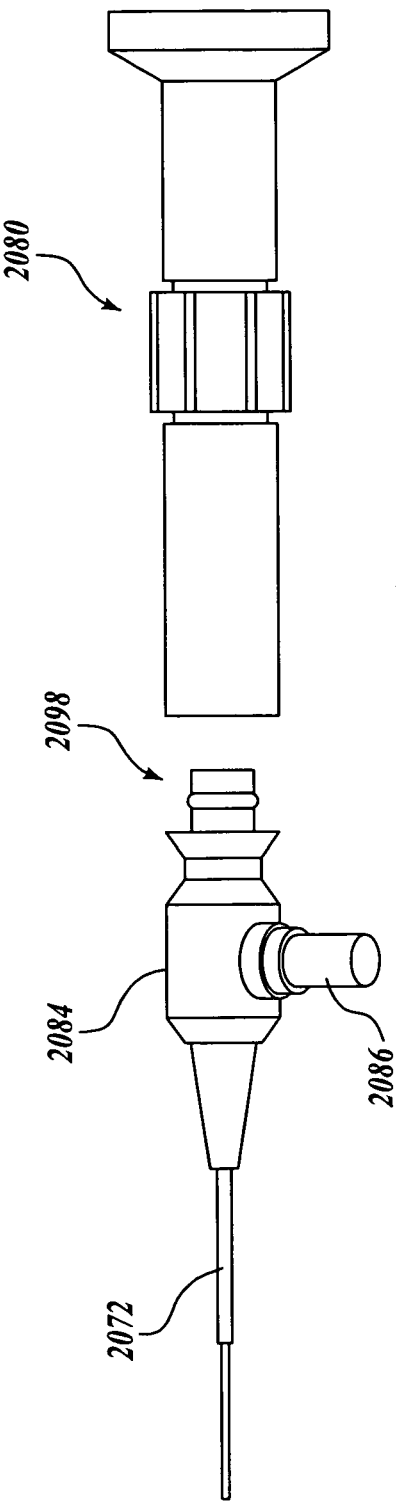
Fig.23A.
Fig.23B.

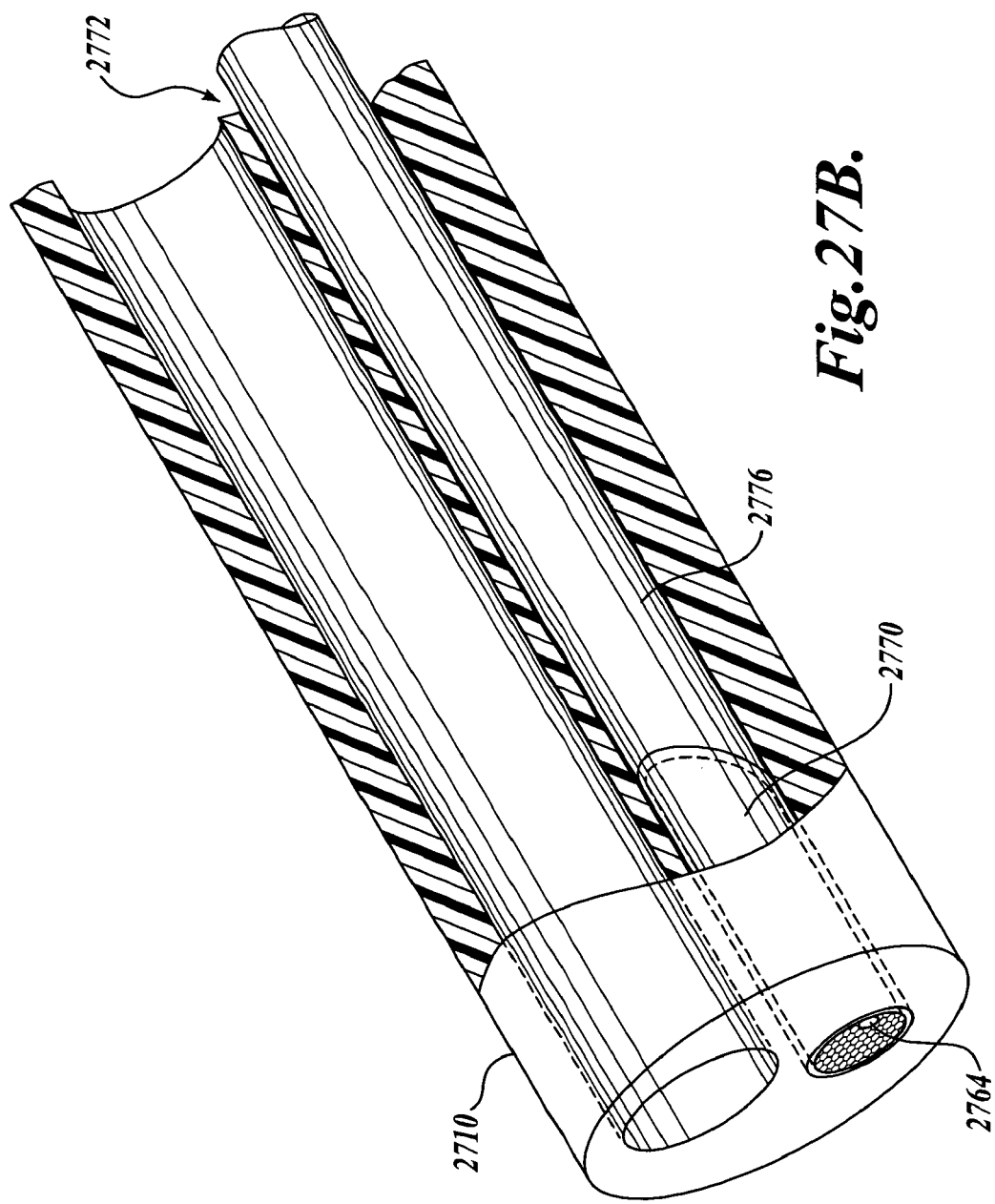

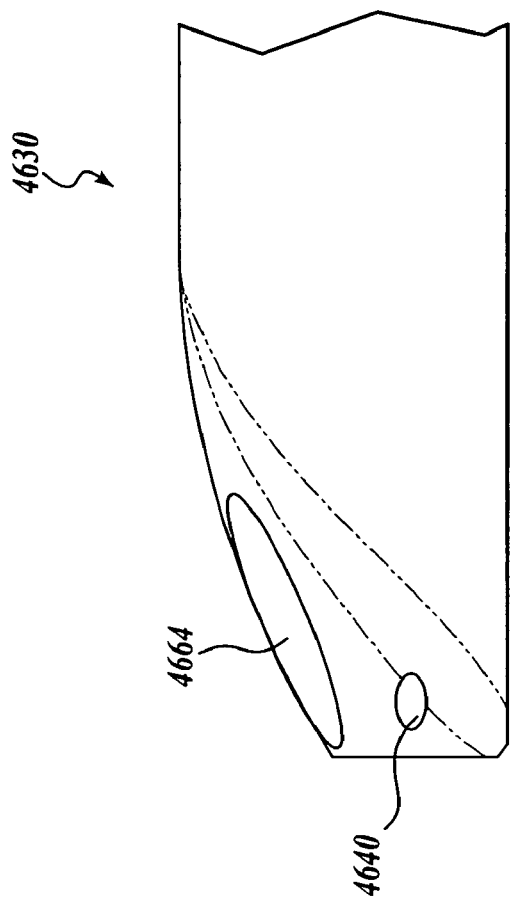
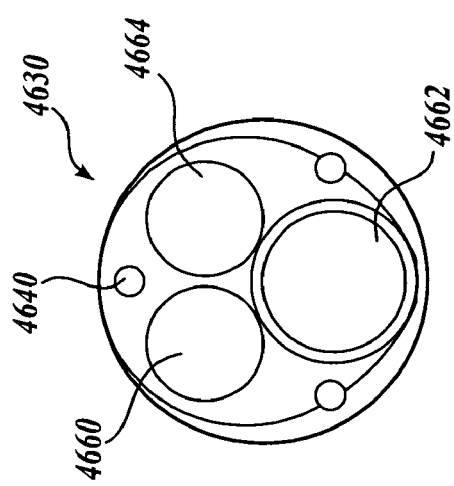
*Fig. 46B.*
*Fig. 46A.*

MEDICAL VISUALIZATION SYSTEM WITH ENDOSCOPE AND MOUNTED CATHETER

CROSS-REFERENCES TO RELATED APPLICATIONS

This application is a continuation-in-part of prior U.S. Application Ser. No. 10/914,411, filed Aug. 9, 2004. This application also claims the benefit of U.S. Provisional Application No. 60/555,356, filed Mar. 23, 2004, and U.S. Provisional Application No. 60/656,801, filed Feb. 25, 2005. All of the aforementioned applications are hereby incorporated by reference.

FIELD OF THE INVENTION

Embodiments of the present invention generally relate to medical devices. Several embodiments are generally directed to medical catheters with steering and/or optical capabilities. Other embodiments are generally related to medical systems, such as in-vivo visualization systems, that are suitable for viewing and/or performing diagnostic and therapeutic modalities within the human body, such as in the biliary tree.

BACKGROUND OF THE INVENTION

A challenge in the exploration and treatment of internal areas of the human anatomy has been adequately visualizing the area of concern. Visualization can be especially troublesome in minimally invasive procedures in which small diameter, elongate instruments, such as catheters or endoscopes, are navigated through natural passageways of a patient to an area of concern either in the passageway or in an organ reachable through the passageway.

Ureteroscopy is one form of procedure that is performed to diagnosis and treat urinary tract diseases and ureteral strictures. In conventional ureterscopy, a ureteroscope is inserted retrograde through the urinary tract such that diagnosis and treatment of urinary tract abnormalities occur under direct visualization. Ureteroscopes are typically 7-10 Fr. in diameter and include a sheath that encapsulates a fiber optic element, an illumination element and a working channel. The working channel allows for the passage of working devices, such as guidewires, stone retrieval baskets and lasers. Some ureteroscopes also incorporate a steering mechanism, which allows the distal tip of the scope to be deflected by the user in one or more planes. Steering is typically achieved via manipulation at the handle end of the scope, ex-vivo.

Problems, however, exist in the use of prior art ureteroscopes. For example, after each successive urological procedure, the scope must be cleaned and sterilized before the next use, which delays successive procedures unless multiple scopes are purchased. Furthermore, current ureteroscopes are non-disposable and require extensive, expensive maintenance. Sterilization delays and costs associated with purchasing and/or repairing scopes have escalated costs for ureteroscopic procedures and other medical procedures that utilize similarly configured scopes.

Detailed information regarding other parts of the anatomy can be discerned from direct viewing of the anatomy provided through one or more of the elongate instruments used in other various medical procedures, such as colonoscopy, upper endoscopy, bronchoscopy, thoracoscopy, laparoscopy, and hysteroscopy. For use in these procedures, various types of endoscopes configured for use in various passageways of the body, such as the esophagus, rectum or bronchus, can be equipped with direct viewing capability through the use of optical fibers extending through the length of the scope, or with digital sensors, such as CCD or CMOS. However, because endoscopes also provide a working channel through which other medical instruments must pass, optional lighting bundles and components to provide steering capability at its distal end, the scope is typically of a relatively large diameter, e.g., 5 mm or greater. This large diameter limits the use of the endoscope to relatively large body lumens and prohibits their use in smaller ducts and organs that branch from a large body lumen, such as the biliary tree.

Typically when examining small passageway such as the bile duct or pancreatic duct, the endoscope is used to get close to a smaller passageway or region of concern and another instrument, such as a catheter, is then extended through the working channel of the endoscope and into the smaller passageway. Although the endoscope provides direct visualization of the large body passageway and entrance to adjoining ducts and lumens, after the smaller catheter has been extended from the endoscope into the smaller duct or lumen, direct visualization has heretofore been limited, and the physician usually relies on radiographical means to visualize the area of concern or probes blindly.

SUMMARY OF THE INVENTION

In accordance with aspects of the present invention, a medical visualization system is provided. The system includes an endoscope having an endoscope insertion tube extending distally from an endoscope handle. The endoscope handle has an access port for accessing an interior lumen of the insertion tube. The endoscope includes an imaging device for viewing objects located at the distal end of the insertion tube. The system also includes a catheter assembly comprising a catheter extending distally from a catheter handle. The catheter handle is selectively mounted to the endoscope and has an access port for accessing an interior lumen of the catheter, wherein the catheter may be inserted into the endoscope access port and routed through a portion of the insertion tube interior lumen. The system further includes an optical assembly comprising an image transmission cable having distal and proximal ends, wherein the image transmission cable is configured for insertion into the catheter access port and routable through a portion of the catheter interior lumen. The optical assembly is capable of obtaining images located at the distal end of the catheter and transmitting the images to the proximal end of the cable.

In accordance with another aspect of the present invention, a medical visualization system is provided. The system includes a disposable catheter having a proximal end and a distal end. The catheter defines one or more interior lumens that extend from the distal end to the proximal end. The system further includes a control handle including an actuation device that effects distal end catheter deflection. The control handle is functionally connected to the proximal end of the catheter. The system further includes a reusable optical assembly that includes an optical handle and an optical cable extending therefrom. The optical cable is routable through a portion of the interior catheter lumen from a position exterior to the catheter.

In accordance with another aspect of the present invention, a catheter handle is provided. The catheter handle is suitable for steering a catheter shaft having a proximal region and a distal region and at least one steering wire having a distal end region secured at or near the distal end region of the catheter shaft and a proximal end. The catheter handle includes a catheter housing having the proximal end of the catheter shaft attached thereto and a steering controller carried by the catheter housing and having the proximal end of the at least one steering wire connected thereto. The steering controller is movable from a first position to a second position. The steering controller is capable of applying tension to the at least one steering wire when the steering controller moves from the first position to the second position. The catheter handle further includes a lock mechanism for retaining the steering controller in the second position to prevent movement thereof. The lock mechanism includes a lever movable between an unlocked position and a locked position. The lever is associated with the steering controller such that movement of the lever to the locked position restricts movement of the steering controller.

In accordance with aspects of the present invention, a method of bifurcating the interior lumens of a catheter for connection to one or more fittings is provided. The method includes obtaining a connector having a central passageway and first and second branch passageway connected thereto, obtaining a catheter having first and second interior lumens extending longitudinally therethrough, and forming first and second openings in the outer surface of the catheter at selected, spaced locations for accessing the first and second interior lumens. The location of the first and second openings correspond to the intersections of the first and second branch passageways with the center passageway of the connector, respectively. The method further includes routing the catheter into the central passageway until the first and second openings communicate with the first and second branch passageways, respectively.

In accordance with another aspect of the present invention, a method of examining a patient in-vivo is provided. The method includes providing an endoscope with an insertion tube having at least one channel. The endoscope has viewing capabilities at the distal end of the insertion tube. The method also includes providing a catheter having at least one channel, providing an imaging device having an image transmission cable, and advancing the insertion tube into a passageway of a patient under direct visualization by the insertion tube. The method further includes advancing the catheter through the insertion tube to a position at or near the distal end of the insertion tube; and advancing the image transmission cable through the catheter channel to a position at of near the distal end of the catheter.

In accordance with another aspect of the present invention, a method is provided for cannulating the papilla of a patient. The method includes providing an optical device having viewing capabilities, providing an endoscope with viewing capabilities and at least one channel, and providing a catheter having at least one channel. The method also includes placing the distal end of the endoscope into the duodenum of a patient and adjacent to the papilla and inserting the catheter into the channel of the endoscope and routing the catheter to the distal end of the endoscope. The method further includes advancing the optical device through the catheter channel to the distal end of the catheter; and advancing the catheter and optical device from the endoscope and through the papilla under visual inspection of the endoscope.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein:

FIG. 20 is a planar view of one suitable embodiment of an optical assembly suitable for use in an optical catheter assembly;

FIG. 23A is a side view of the optical handle of FIG. 20;

FIG. 23B is a side view of the optical handle of FIG. 20 showing the detachable nature of its components;

FIGS. 27A-27B are partial perspective views of a distal portion of one embodiment of a catheter formed in accordance with aspects of the present invention, several portions of FIG. 27 is shown in cross-section;

FIG. 46A is an end view of a distal end of another embodiment of a catheter formed in accordance with the present invention;

FIG. 46B is a partial side elevational view of the distal end of the catheter shown in FIG. 46A;

DETAILED DESCRIPTION OF THE PREFERRED EMBODIMENT

Embodiments of the present invention will now be described with reference to the drawings where like numerals correspond to like elements. Embodiments of the present invention are directed to systems of the type broadly applicable to numerous medical applications in which it is desirable to insert one or more steerable or non-steerable imaging devices, catheters or similar devices into a body lumen or passageway. Specifically, several embodiments of the present invention are generally directed to medical visualization systems that comprise combinations of disposable and reusable components, such as catheters, functional handles, hubs, optical devices, etc.

Other embodiments of the present invention are generally directed to features and aspects of an in-vivo visualization system that comprises a catheter having a working channel through which a catheter having viewing capabilities is routed. As will be described in detail below, the catheter may obtain viewing capabilities by being constructed as a vision catheter or by having a fiberscope or other viewing device selectively routed through one of its channels. The catheter is preferably of the steerable type so that the distal end of the catheter may be steered from its proximal end as it is advanced within the body. A suitable use for the in-vivo visualization system includes but is not limited to diagnosis and/or treatment of the duodenum, and particularly the biliary tree.

Several embodiments of the present invention include medical devices, such as catheters, that incorporate endoscopic features, such as illumination and visualization capabilities, for endoscopically viewing anatomical structures within the body. As such, embodiments of the present invention can be used for a variety of different diagnostic and interventional procedures. Although exemplary embodiments of the present invention will be described hereinafter with reference to duodenoscopes, it will be appreciated that aspects of the present invention have wide application, and may be suitable for use with other endoscopes (e.g., ureteroscopes) or medical devices, such as catheters (e.g., guide catheters, electrode catheters, angioplasty catheters, etc.). Accordingly, the following descriptions and illustrations herein should be considered illustrative in nature, and thus, not limiting the scope of the present invention. Additionally, the catheter with vision capabilities may be utilized alone, as well as in conjunction with a conventional endoscope.

Figure 1:
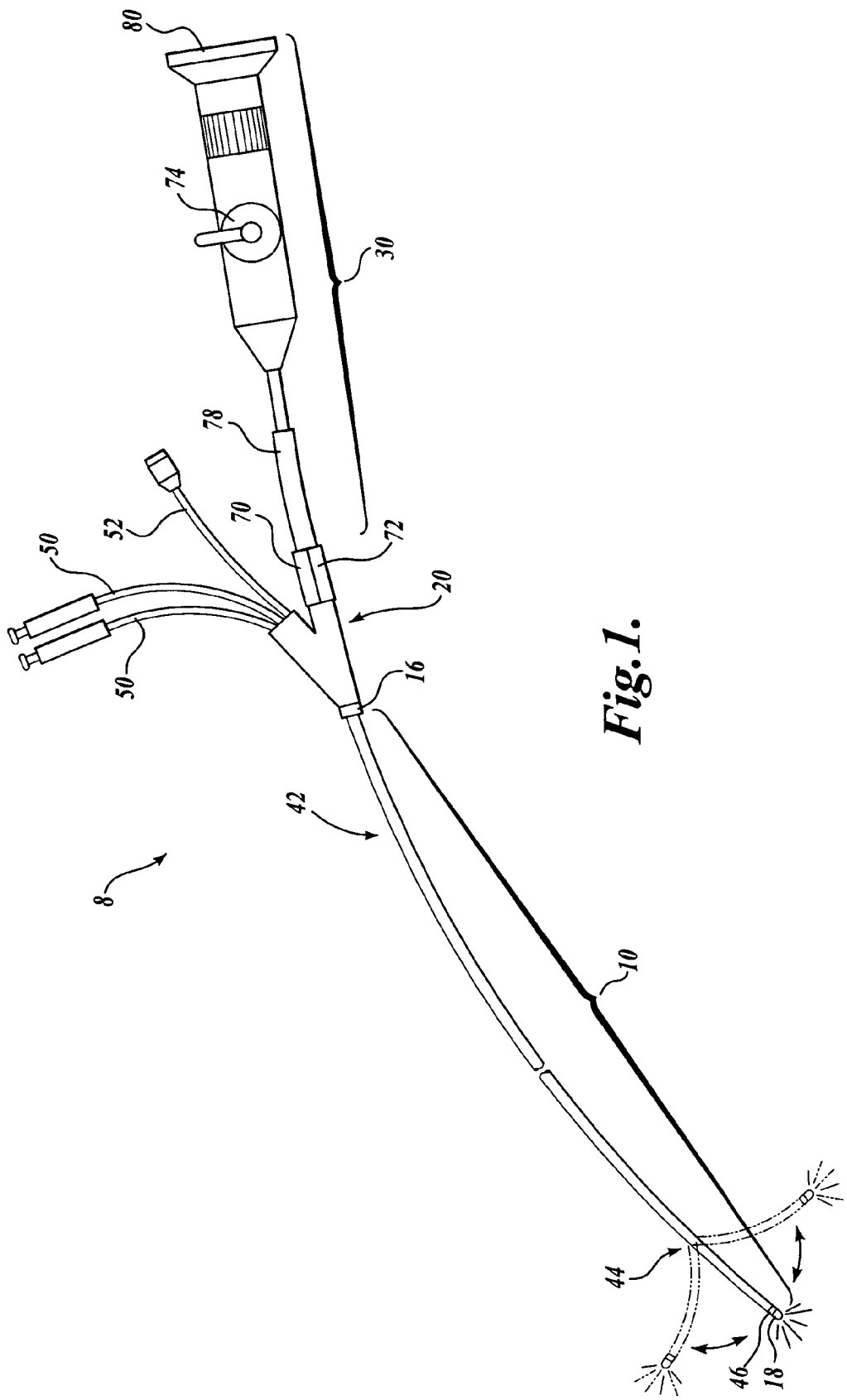
FIG. 1 is an assembly view of an optical catheter system according to one embodiment of the invention.

FIG. 1 illustrates an optical catheter system 8 in accordance with one embodiment of the present invention. The primary components of the system 8 include a sterile, single-use, disposable catheter 10, a sterile, single-use, disposable hub 20, and a reusable handle 30. In the illustrated embodiment, the hub 20 is integral, i.e., permanently part of, the disposable catheter 10 such that they together define a sterile, single-use, disposable catheter assembly. For example, the hub 20 may be joined to the catheter 10 with injection molding or adhesive bonding. The catheter assembly defined by the hub 20 and catheter 10 is preferably packaged in a sterile container or package (not illustrated) prior to use by a physician. In an alternative embodiment, the hub 20 is integral, i.e., permanently part of, the handle 30. In a further embodiment, the hub 20 is not integral with the catheter 10 or the handle 30, but connects to these items with connectors, such as male and female threaded connectors, quick lock connectors, bayonet connectors, snap connectors, or other known connectors.

Figure 2:
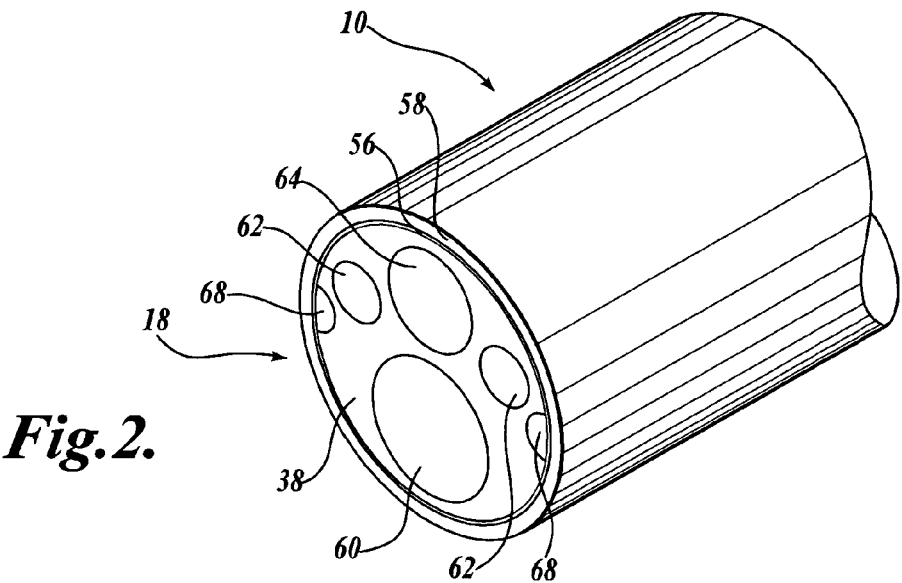
FIG. 2 is a perspective end view of the distal tip of the catheter illustrated in FIG. 1.
Figure 3:
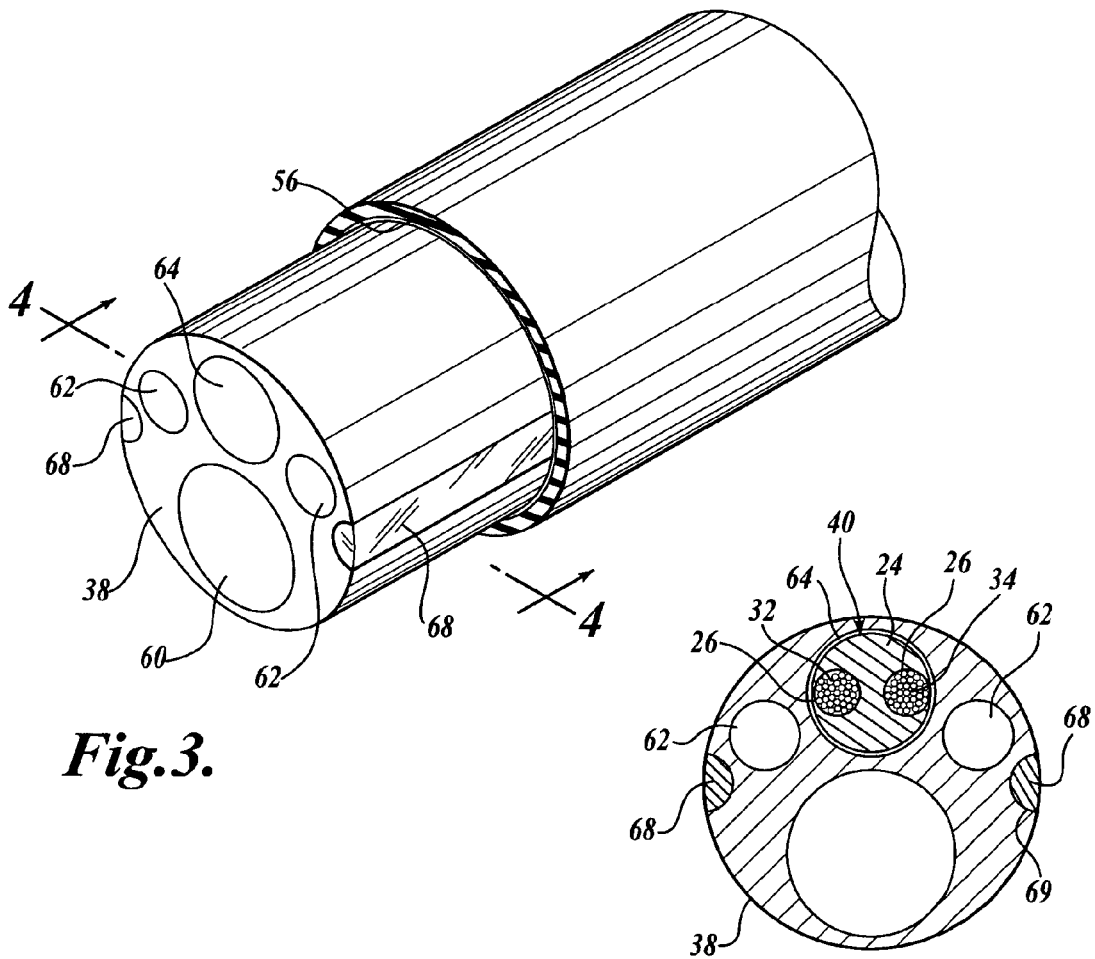
FIG. 3 is perspective end view of the distal tip of the catheter illustrated in FIG. 1, where the sheath of the catheter has been removed to expose the elongated, internal body of the catheter.
Figure 4:
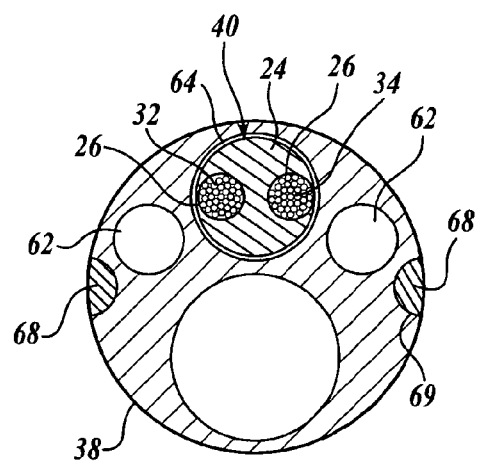
FIG. 4 is a cross-sectional view of the elongated body of the catheter illustrated in FIG. 3, taken along the line 4-4 in FIG. 3.

As is illustrated in FIGS. 2-4, the catheter 10 includes an elongated, preferably cylindrical, body 38 that extends the entire length of the catheter 10. In one embodiment, the catheter body 38 has an outer diameter between approximately 5 and 12 French, and preferably between approximately 7 and 10 French. The catheter body 38 may be constructed from any suitable material, such as Pebax® (polyether block amides), nylon, polytetrafluoroethylene (PTFE), polyethylene, polyurethane, fluorinated ethylene propylene (FEP), thermoplastic elastomers and the like, or combinations thereof. The body 38 may be formed of a single material using known techniques in the art, such as extrusion, or multiple materials by joining multiple extruded sections by heat bonding, adhesive bonding, lamination or other known techniques (e.g., juxtaposed Nitinol tubes wrapped with an adhesive bonding.

In some applications, e.g. urological, it is desirable that the catheter 10 have a varying degree of stiffness from the distal (e.g., renal pelvis) end 18 towards the proximal (e.g., bladder) end 16. The proximal end 16 should be stiff enough for the device to advance in the tract to the desired location (e.g., in the urinary tract to the renal pelvis/kidney area). The distal end 18 should be soft enough to provide a reduction in trauma during insertion but rigid enough to provide adequate support during the procedure and prevent collapse or kinking. According to an embodiment of the present invention for urological application, the distal portion of the catheter (approximately 1-2 inches where the flexing occurs) is made more flexible (i.e., less stiff) than the remainder of the catheter to allow for steerability of the catheter in vivo. Several techniques for constructing a catheter having a more flexible distal portion than the remainder of the catheter will be described in more detail below.

In the embodiment shown in FIG. 1, the catheter 10 includes a proximal portion 42 that extends the majority of the catheter 10 and a distal portion 44. The catheter 10 preferably varies in stiffness between the proximal portion 42 and the distal portion 44. More preferably, the proximal portion 42 is stiffer than the distal portion 44. This allows the catheter 10 to be easily advanced without compressing and with minimal twisting while providing deflection capabilities to the distal portion 42 for deflecting the distal end 18. In one embodiment, the proximal portion 42 has a durometer value between 35 and 85 shore D, preferable 60-80 shore D, and the distal portion 44 has a durometer value between 5 and 55 shore D, preferable 25-40 shore D.

As is illustrated in FIGS. 2 and 3, the catheter 10 may optionally include an inner sheath 56 and/or an outer sleeve 58 that encase the length of the elongated body 38 or portions thereof. In one embodiment, the sheath 56 is a woven or layered structure, such as a braided design of fine wire or polymeric elements woven or coiled together along the longitudinal axis of the catheter with conventional catheter braiding (e.g., 2 wires having a diameter ranging from 0.001 to 0.010 inches wound in a 2-over, 2-under helical fashion from the proximal to distal end of the catheter 10). This allows the catheter 10 to be advanced to the desired anatomical site by increasing the column strength of the assembly while also increasing the torsional rigidity of the catheter. Conventional coiled polymer or braid wire may also be used for this component with coil wire dimensions ranging in width from 0.002 to 0.120 inches and thickness from 0.002 to 0.10 inches. Braided ribbon wire (e.g., 0.002×0.005 inches; 0.003×0.012 inches) may also be used for the sheath 56.

The outer sleeve 58 may comprise of any number of polymer jackets that are laminated over the first sheath 56. Suitable materials for the sleeve 58 include, but without limitation, polyethylene, such as polyethylene having a molecular weight in the range of 50,000 to 100,000; nylon, such as nylon 12, nylon 4-6, and nylon 6-6; Pebax (polyether block amides); polyurethane; polytetrafluoroethylene (PTFE), particularly fluorinated ethylene propylene (FEP) copolymers; and polyethylene impregnated with PTFE. The outer sleeve 58 may be used to vary the stiffness of the catheter, if desired, or to provide improved torque transfer and/or other desirable catheter properties. Additionally, the sleeve 58 may be used as one convenient method for securing a more flexible deflection section to the proximal section, as will be described in detail below. In one embodiment, as will be described in more detail below, the outer sleeve 58 is coextruded, coated, or otherwise attached once the sheath 56 is applied, to lock the sheath 56 in place and secure it to the catheter body 38, thereby forming a composite catheter.

In several embodiments, the external surface of the catheter, for example, the outer sleeve 58, can have a hydrophilic coating or a silicone coating to ease the passage of the device in vivo. Such a hydrophilic coating can be, for example, but without limitation, N-Vinyl Pyrrolidone, Poly Vinyl Alcohol, and Poly Vinyl Pyrrolidone. The hydrophilic coating can be accomplished by coating the device with a primer, such as Bayhydrol 110 (an anionic dispersion of an aliphatic polyester urethane resin in water/n-methyl-2pyrrolidone) and then bonding a primary layer over the primer. The primary layer can be, without limitation, an acrylamide or a polyurethane-based acrylamide. Alliphatic polyether and polyester polyurethanes also can be used as lubricous coatings.

In a further embodiment, the distal portion 44 of the catheter 10 may contain a preset curve detail that allows a physician to easily access various locations (e.g., the renal pelvis) with minimal manipulation via passive deflection (i.e., without ex-vivo steering mechanism actuation). In one embodiment, the durometer of the sleeve 58 varies from 35 Shore D to 85 Shore D (preferably in the region of 70-80 D) at the proximal end 16 to 20 Shore D to 55 Shore D (preferably in the region of 30-43 D) at the distal end 18. Curves of various shapes and geometries may be preset to the distal portion 44 of the catheter 10 as desired. For example, these curves may be pre-baked into the sleeve 58 at an elevated temperature below the melting point of the polymer. This pre-baked curve can vary between 10 and 270 degrees from vertical, depending upon the specific application of the system 8. To insert the catheter 10, the curve should be such that when a dilator or stiff guidewire is inserted into a working channel of the catheter 10 (described below), the curve is straight, while once the dilator or guidewire is removed, the distal portion 44 reverts to the pre-baked curve providing access to a desired location.

In one embodiment, the distal portion 44 of the sleeve 58 has a radiopaque marker band 46 mounted thereon to provide confirmation of the location of the distal end 18 via fluoroscopy.

Referring now to FIGS. 2-4, the elongated body 38 of the catheter 10 defines a working channel 60 that extends the entire length of the catheter and allows for the passage of various treatment or diagnostic devices, such as guide wires, stone retrieval baskets, lasers, biopsy forceps etc. The working channel 60 preferably has a diameter sufficient to accept up to a 4 French working device, such as a retrieval basket device or biopsy forceps. The elongated body 38 of the catheter 10 may also include additional channels 62, for use, e.g., as irrigation/insufflation channels or additional working channels for one or more of the instruments mentioned above. The channels 62 each extend the entire length of the catheter 10 and, like the working channel 60, allow the passage of devices, liquids and/or gases to and from the treatment area. The channels 62 each have a diameter similar to or smaller than main working channel 60. In one embodiment, the channels 62 each have a diameter of about 0.020 inches. The catheter may also include a channel 64 that extends the entire length of the catheter through which a fiberscope, fiber optic cables or other small diameter imaging devices (e.g., 0.25 mm-1.5 mm diameter) can be routed to the distal end of the catheter 10. It will be appreciated that one or more of the channels 62 may be eliminated or dimensioned to accommodate the necessary diameter needed for the working channel 60 and optic lumen.

As is illustrated in FIGS. 2-4, the catheter 10 also includes a pair of control or steering wires 68 that cause a distal portion 44 of the catheter 10 to deflect in one or more directions as indicated by the dashed lines in FIG. 1. The steering wires 68 are located on opposite sides of the catheter 10 and slide within grooves 70 in opposite sides of the elongated body 38. In other embodiments, the steering wires 68 may reside in the sheath 56 or outer sleeve 58. In yet another embodiment, the steering wires 68 may be routed through dedicated steering wire lumens in the catheter. The steering wires 68 extend from the distal end 18 of the catheter 10 to the opposing, proximal end 16 of the catheter 10, and then through the hub 20. The steering wires 68 may be attached to the distal end 18 of the catheter 10 in a conventional manner, such as adhesive bonding, heat bonding, crimping, laser welding, resistance welding, soldering or other known techniques, at anchor points such that movement of the wires causes the distal end to deflect in a controllable manner. In one embodiment, the steering wires 68 are attached via welding or adhesive bonding to a fluoroscopy marker band 46 (see FIG. 1) fixedly attached to the distal end. In one embodiment, the band may be held in place via adhesive and/or an outer sleeve, as will be described in more detail below. The steering wires 68 preferably have sufficient tensile strength and modulus of elasticity that they do not deform (elongate) during curved deflection. In one embodiment, the steering wires are made from 304 stainless steel with an 0.008 inch diameter and have a tensile strength of approximately 325 KPSI. The steering wires 68 can be housed in a PTFE thin-walled extrusion (not shown) to aid in lubricity and prevent the catheter 10 from binding up during deflections, if desired.

In the illustrated embodiment shown in FIG. 1, the steering wires 68 terminate in a wire connector 70, which may also be part of the hub 20. The wire connector 70 is a mechanical device that provides a detachable, preferably quick-fit, connection between the steering wires of the catheter 10 and the controller 74 or handle steering wires (not illustrated) associated with the handle 30. Various types of detachable mechanical connectors, such as joints and linking elements, are capable of forming a connection that allows active deflection of the wires 68 via the controller 74 of the handle 30. In the illustrated embodiment, the catheter 10 includes two steering wires 68 that controllably steer the catheter distal end 18 within one plane. In alternative embodiments, the catheter 10 includes additional wires that allow a user to steer the distal end 18 in multiple planes. In a further embodiment, the catheter 10 only includes one control wire that allows the user to steer the distal end 18 in one direction. In another embodiment, such as described below, the steering wires 68 are not part of the catheter 10. In such an embodiment, the catheter can be advanced over a guidewire (not shown) pre-placed in the region of interest.

Figure 5:
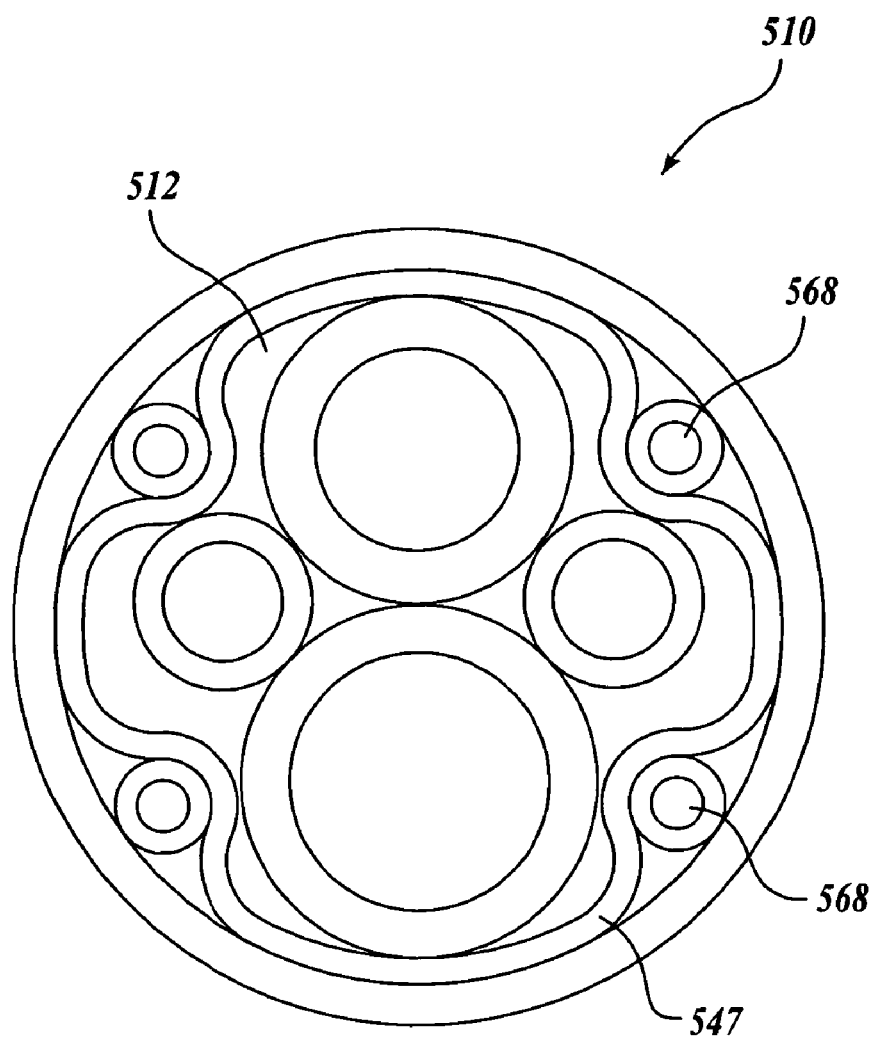
FIG. 5 is a cross-sectional view of an alternative embodiment of a catheter of the system illustrated in FIG. 1, where the cross-section is taken along a longitudinal axis of the catheter.

Referring now to FIG. 5, there is shown a cross-sectional view of an alternative embodiment of a catheter 510 suitable for use with the optical catheter system 8. The catheter 510 illustrated in FIG. 5 also includes additional features and inherent functions, as described further below. Unlike the catheter 10, the catheter 510 has one large lumen 512 as opposed to multiple lumens. This is referred to as a "loose tube" configuration. The steering wires 568 run along the inner diameter of the catheter 510 to the distal end and are located within channels defined by an internal sleeve or liner 547. The liner 547 has a low co-efficient of friction to facilitate the passage of working devices through the catheter during surgery. The liner 547 has a wall thickness from 0.0005 to 0.010 inches and is preferably formed from nitinol tubing, a polymer containing a degree of fluoroethylene such as, but not limited to, FEP, PTFE or PTFE impregnated thermoplastic elastomers like Pebax or is formed from a polymer having fluroethylene combined with thermoplastic materials such as polyamides, polyurethane, polyethylene and block co-polymers thereof. The optical assembly, any working devices, and any irrigation tubes pass through the lumen 512 and connect with the hub as described above and below. In an alternative embodiment, the elongated body 538 of FIGS. 2-4 passes through the lumen 512, where the elongated body 538 routes any working devices, the optical assembly, and any irrigation tubes as described above.

Figure 12A:
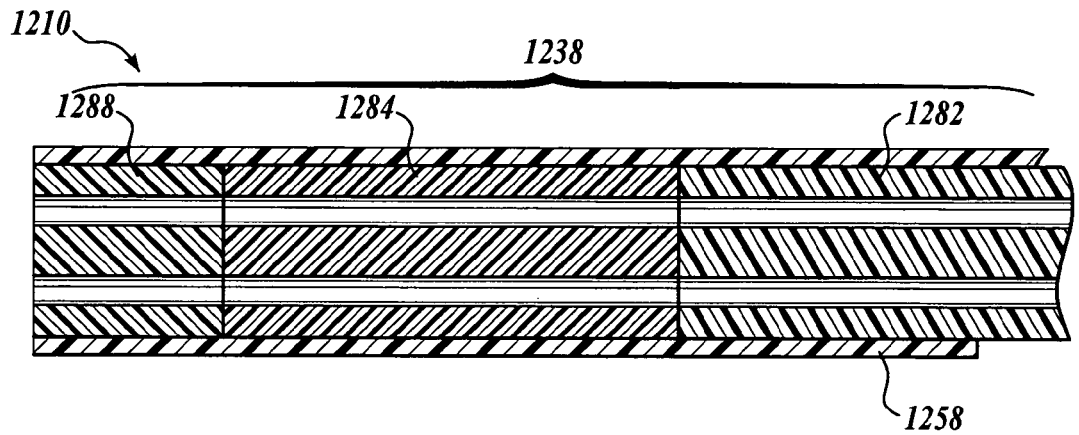
FIG. 12A is a partial longitudinal cross section view of another embodiment of a catheter formed in accordance with aspects of the present invention.

The catheter 10 may be constructed in many different ways to achieve the desired result of a catheter having varying stiffness along its length, a few of which will now be described in more detail. FIG. 12A is a longitudinal cross-section view of one embodiment of a catheter 1210 constructed in accordance with aspects of the present invention. As best shown in FIG. 12A, the catheter 1210 comprises a catheter body 1238 that is constructed with discrete proximal, deflection, and distal tip sections 1282, 1284, 1288. In this embodiment, the proximal section 1282 is stiffer than the deflection section 1284. Each section may be constructed in any suitable manner, such as extrusion or milling, with any suitable materials, such as polyethylene, nylon, Pebax® (polyether block amides), polyurethane, polytetrafluoroethylene (PTFE), thermoplastic elastomers, chosen for the desired application. The sections 1282, 1284, 1288 are then coupled together to form an integral body by encasing the length of the body 1238 or portions thereof with an outer sleeve 1258. The deflection section may contain one or both of section elements 1284 and 1288 to impart the required deflection at the distal end to the system. The outer sleeve 1258 may comprise one of any number of polymer jackets that are laminated, co-extruded, heat shrunk, adhesive bonded, or otherwise attached over the catheter body 1238. Suitable materials for the sleeve 1258 include, but are not limited to, polyethylene, nylon, Pebax® (polyether block amides), polyurethane, polytetrafluoroethylene (PTFE), and thermoplastic elastomers to name a few. It will be appreciated that the sections 1282, 1284, and 1288 may also be heat bonded or adhesive bonded prior to outer sleeve attachment.

Figure 12B:
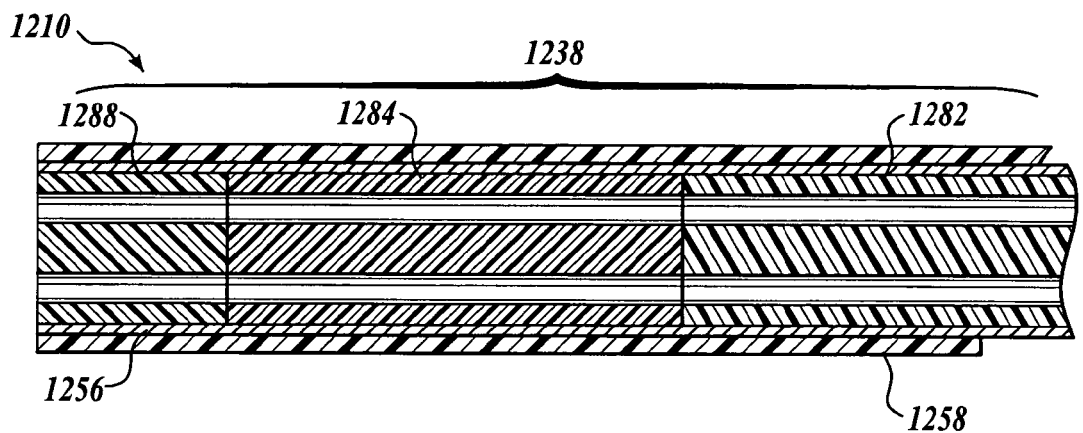
FIG. 12B is a partial longitudinal cross section view of another embodiment of a catheter formed in accordance with aspects of the present invention.

The catheter 1210 may optionally include an inner reinforcement sheath 1256, for example, a metallic braid, disposed between sections 1282, 1284, and 1288 of the elongated body 1238 and the outer sleeve 1258, as best shown in FIG. 12B. The reinforcement sheath 1256 encases the length of the catheter body 1238 or portions thereof. In one embodiment, the reinforcement sheath extends from the proximal end of the catheter body to proximal an optional radio opaque band (not shown) at the distal tip section. The reinforcement sheath increases the kink resistance of the deflecting section 1284 to ensure that internal lumens remain patent during bending.

Figure 13A:
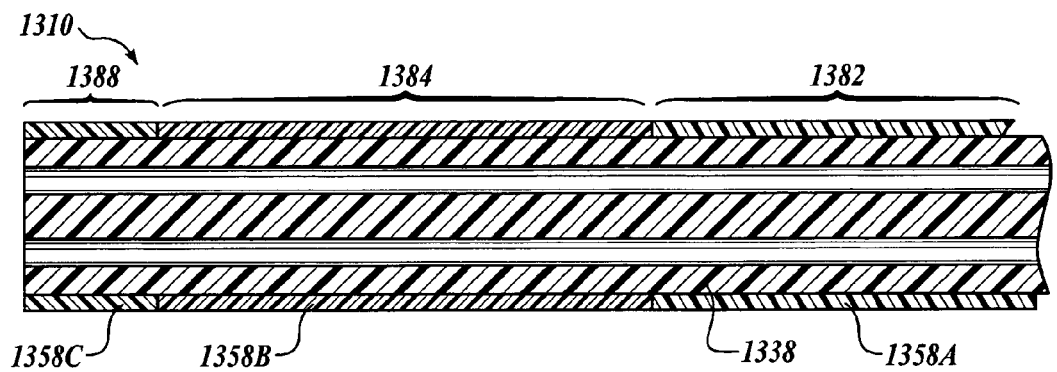
FIG. 13A is a partial longitudinal cross section view of another embodiment of a catheter formed in accordance with aspects of the present invention.

FIG. 13A is a longitudinal cross section view of another embodiment of a catheter 1310 constructed in accordance with aspects of the present invention. As best shown in FIG. 13A, the catheter 1310 defines a proximal section 1382, a deflection section 1384, and a distal tip section 1388. The catheter 1310 comprises a catheter body 1338 and an outer sleeve 1358. The catheter body 1338 is a unitary core that is formed, preferably by extrusion, with one suitable material, such as nylon, Pebax®, PTFE, etc. In one embodiment, the body 1338 is a PTFE extrusion. When assembled, the outer sleeve 1358 encases the length of the elongated body 1338 or portions thereof. The outer sleeve 1358 comprises a number of polymer jackets 1358A, 1358B, and 1358C that are laminated, co-extruded, heat shrunk, adhesive bonded, or otherwise attached over sections 1382, 1384, and 1388 respectively, of the catheter body 1338. The stiffness value of each jacket is specifically selected to achieve the desired results, and may vary upon different catheter applications.

In one embodiment, the jacket 1358A, which corresponds to the proximal section 1382, is constructed of a material having a greater stiffness value than the jacket 1358B, which corresponds to the deflection section 1384. Suitable materials for the sleeve 1358 include, but are not limited to, polyethylene, nylon, Pebax® (polyether block amides), polyurethane, polytetrafluoroethylene (PTFE), to name a few. If PTFE is chosen for the body 1338, it may be necessary to etch or otherwise prepare its outer surface to promote suitable adhesion of the outer sleeve 1358.

Figure 13B:
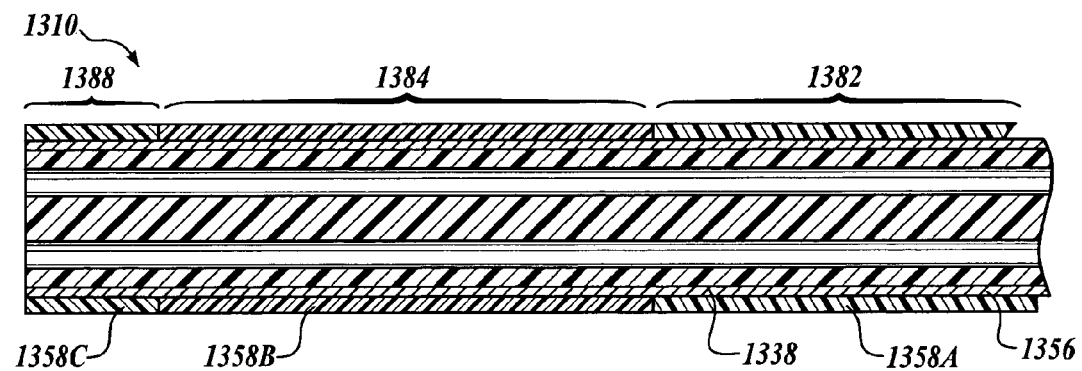
FIG. 13B is a partial longitudinal cross section view of another embodiment of a catheter formed in accordance with aspects of the present invention.

The catheter 1310 may optionally include an inner reinforcement sheath 1356, for example, a metallic braid, disposed between the elongated body 1338 and the outer sleeve 1358, as best shown in FIG. 13B. The reinforcement sheath encases the length of the elongated body 1338 or portions thereof. In one embodiment, the reinforcement sheath extends from the proximal end of the catheter body to proximal an optional radio opaque band (not shown) at the distal tip section. The reinforcement sheath increases the kink resistance of the deflecting section to ensure that internal lumens remain patent during bending.

Figure 14A:
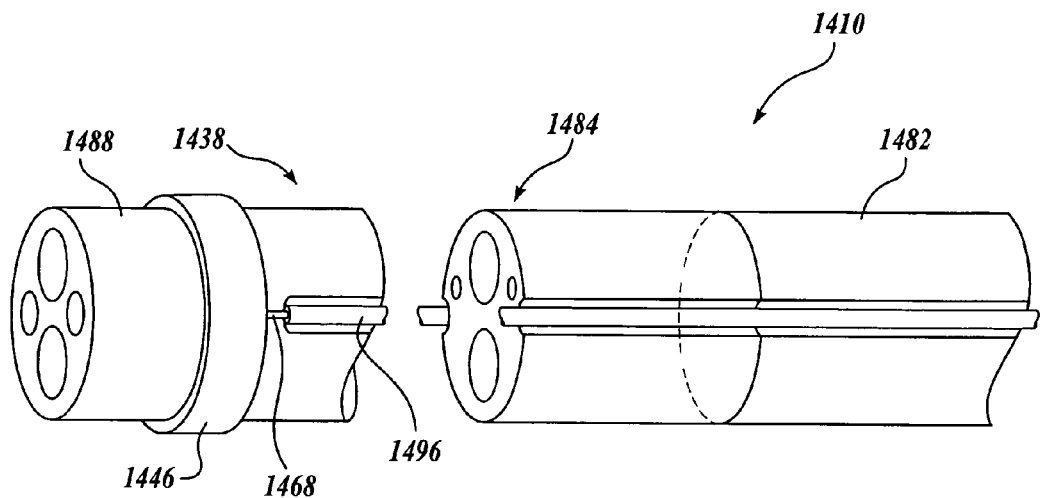
FIG. 14A is a partial view of one suitable embodiment of a catheter body constructed in accordance with aspects of the present invention.

FIGS. 14A-14C and 15 illustrate another embodiment of a catheter 1410 constructed in accordance with aspects of the present invention. As best shown in FIG. 14A, the catheter includes a catheter body 1438 having a proximal section 1482, a deflecting section 1484, and a distal tip section 1488. In one embodiment, the proximal section 1482 is constructed of a material that is stiffer than the deflecting section 1484. The proximal section 1482 and the deflecting section 1484 may be extrusions constructed from any suitable material, such as polyethylene, nylon, Pebax® (polyether block amides), polyurethane, polytetrafluoroethylene (PTFE), and thermoplastic elastomers, to name a few. In one preferred embodiment for urological application, the proximal section is a multi-lumen, PTFE extrusion approximately 200 to 220 cm in length, and the deflecting section 1484 is a multi-lumen, Pebax® extrusion approximately 2 to 10 cm in length. The deflection section 1484 may be coupled to the proximal section 1482 via suitable adhesive or joined by other techniques. The distal tip section 1488 may be coupled to the distal end of the deflection section 1484 via suitable adhesive. The distal tip section 1488 may be constructed of any suitable material, such as stainless steel or engineering plastics, including but not limited to polyethylene, nylon, Pebax® (polyether block amides), polyurethane, polytetrafluoroethylene (PTFE), and thermoplastic elastomers. The catheter body 1438 may also include a radio opaque marker band 1446 that encircles a portion of the distal tip section 1488.

Figure 14B:
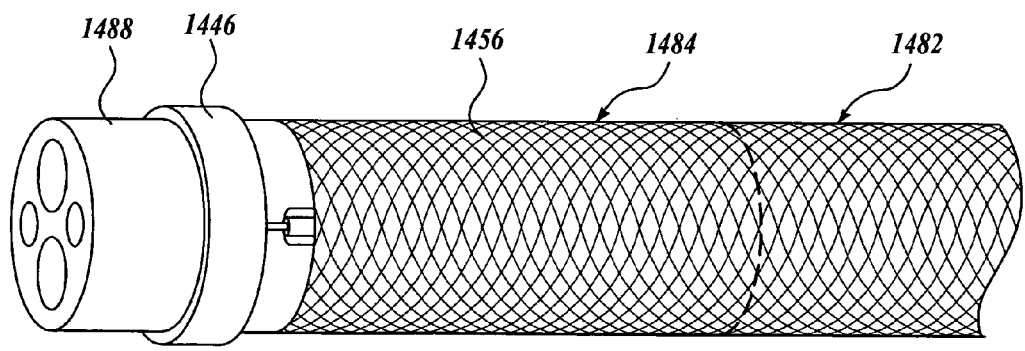
FIG. 14B is a partial view of one suitable embodiment of a catheter formed by taking the catheter body of FIG. 14A and encasing said catheter body with a reinforcement sheath.
Figure 14C:
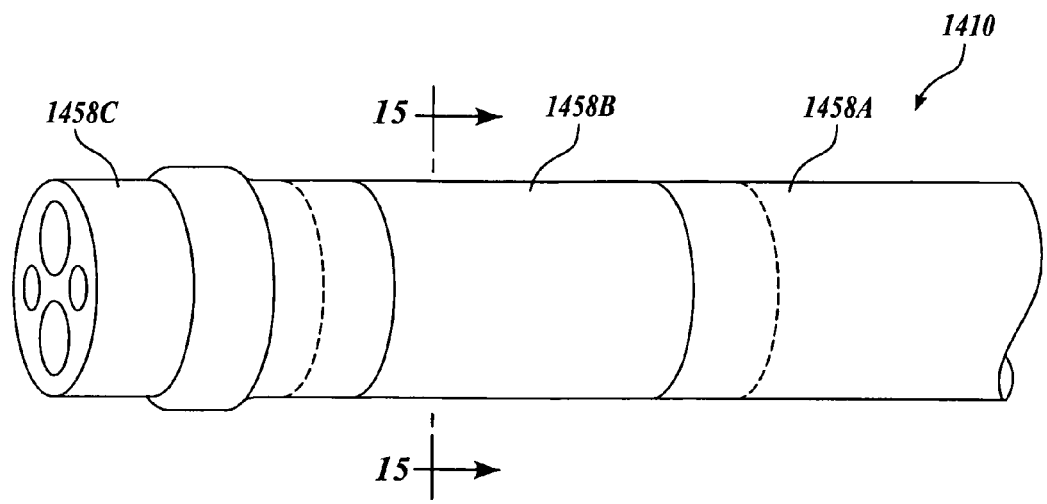
FIG. 14C is a partial view of one suitable embodiment of a catheter formed by taking the catheter of FIG. 14B and encasing said catheter with an outer sleeve.

The catheter 1410 (see FIG. 14B) also includes a reinforcement sheath 1456 that extends from the proximal end of the catheter to or immediately proximal of the radio opaque marker band 1446. The sheath 1456 may be a woven or layered structure, such as a braided design of fine wire or polymeric elements (0.001 inches to 0.010 inches in diameter) woven or coiled together along the longitudinal axis of the catheter with conventional catheter braiding techniques. This allows the catheter to be advanced to the desired anatomical site by increasing the column strength of the assembly while also increasing the torsional rigidity of the catheter. The reinforced catheter body shown in FIG. 14B is then encased by an outer sleeve 1458 comprising of one or more sleeve sections 1458A, 1458B, and 1458C, having the same or different stiffness values, as best shown in FIG. 14C, to form the catheter 1410.

Returning to FIG. 14A, the catheter also includes a plurality of steering wires 1468 that extend through grooves or slots formed in the catheter body from the proximal end of the catheter past the deflecting section 1484. In one embodiment, the steering wires 1468 terminate at the radio opaque marker band 1446 to which the steering wires 1468 are joined by adhesive bonding, laser welding, resistance welding, soldering or other known techniques.

Figure 15:
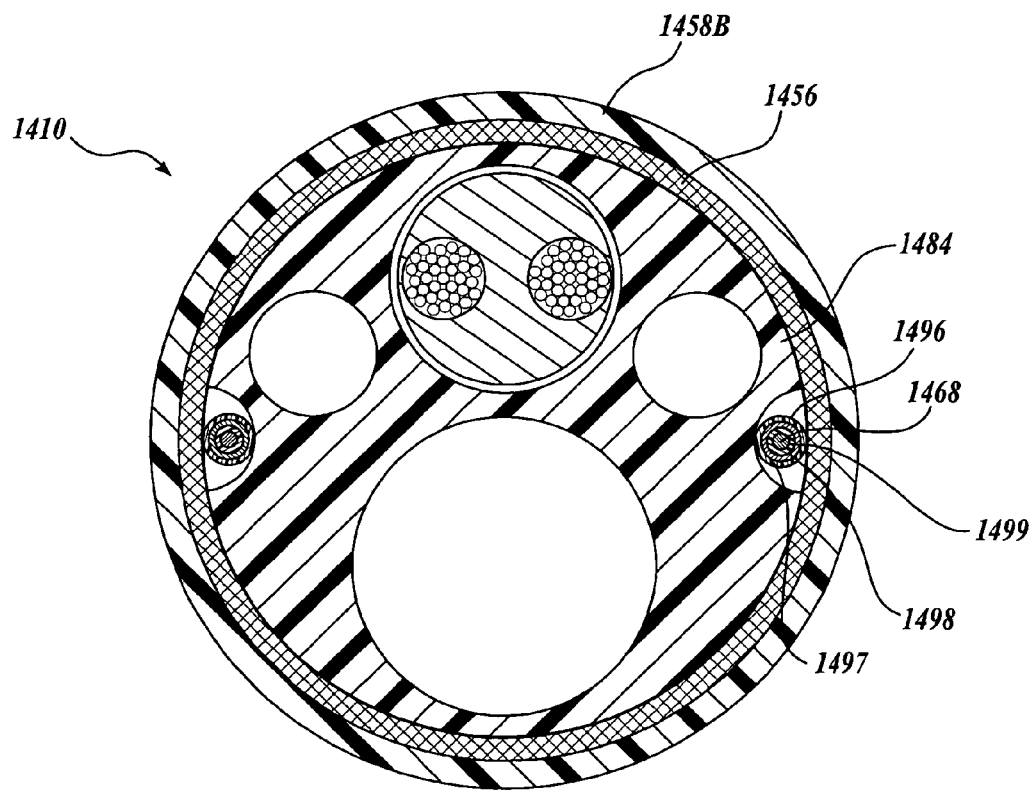
FIG. 15 is a cross sectional view of the catheter taken along lines 9-9 in FIG. 14B.

In several embodiments, it is preferable for the steering wires to be encased with a laminate structure 1496 for allowing the steering wires 1468 to move freely within or along the catheter body, and thus, make the mechanics of actuation as smooth as possible. As best shown in FIG. 15, the laminate structure 1496 is formed by outer jacket 1497 constructed of a thermoplastic polymer, such as polyurethane, Pebax®, thermoplastic elastomer etc. which encases an inner reinforcement member 1498, such as a metallic braid (e.g., stainless steel braid having, for example, a 0.0015"×0.006" helically wound). Inside the reinforcement member 1498, is a layer 1499 of a friction reducing material, such as PTFE or FEP tubing, over which the aforementioned layers are formed. The laminate structure 1496 begins at the proximal section 1482 and extends to just proximate the radio opaque marker band 1446, as best shown in FIG. 14A.

As was described above, in several embodiments of the catheter, it is desirable for the deflection section or distal portion to be configured to deflect more easily than the proximal section or portion. In one embodiment, the deflection section or distal portion has a durometer value less than the proximal section. In other embodiments, the flexibility may be varied gradually (e.g., increasingly) throughout the length of a catheter tube from its proximal end to its distal end. In other embodiments, the deflection section may be an articulating joint. For example, the deflection section may include a plurality of segments that allow the distal section to deflect in one or more directions. For examples of articulation joints that may be practiced with the present invention, please see co-pending U.S. patent application Ser. Nos. 10/406,149, 10/811,781, and 10/956,007, the disclosures of which are hereby incorporated by reference.

Figure 16:
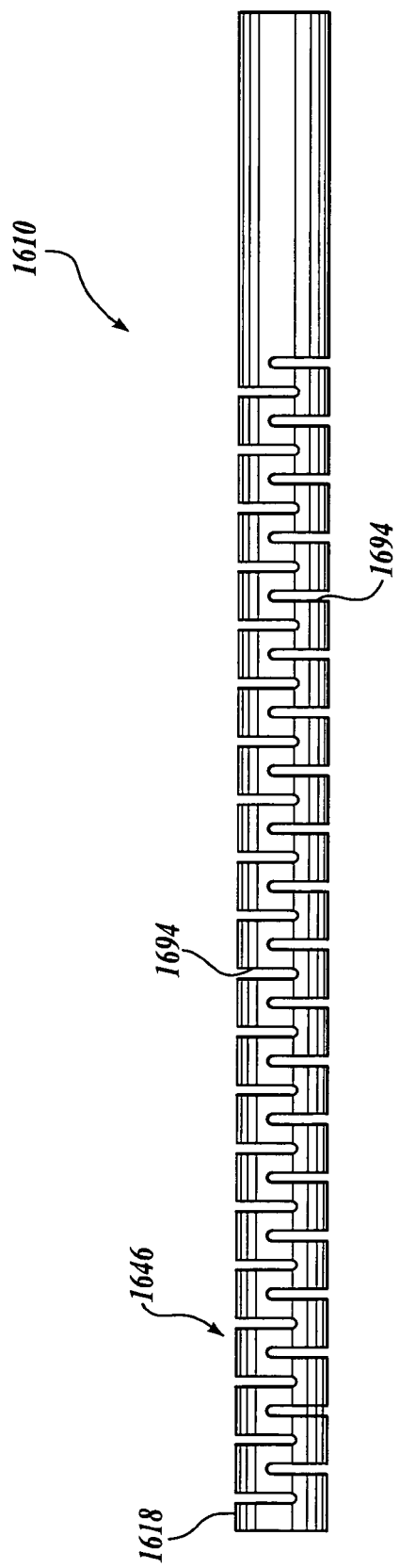
FIG. 16 is a partial view of the distal end of another embodiment of a catheter that is suitable for used in the system illustrated in FIG. 1.

Other mechanical joints or configurations may be utilized that allow the distal portion of the catheter to flex or bend in one or more directions more easily. Turning now to FIG. 16, there is shown one embodiment of a catheter 1610 formed in accordance with aspects of the present invention. FIG. 16 shows a partial view of the distal portion 1646 of a catheter 1610 constructed from a metal or plastic tube with slots 1694 cut 180 degrees and spaced an even distance apart to form a deflecting section. The slots will allow the catheter 1610 to deflect in two directions or in a single plane at the distal end 1618. The proximal section of the tube is not slotted and may be used as the non-deflecting portion of the catheter. If preferred, the slotted section may be used in embodiments discussed above. The slotted section can be useful when the catheter profile is not symmetrical or is irregular. It will be appreciated that the slots 1694 can be V-shaped, semi-circle, wave or any preferred configuration.

Figure 17:
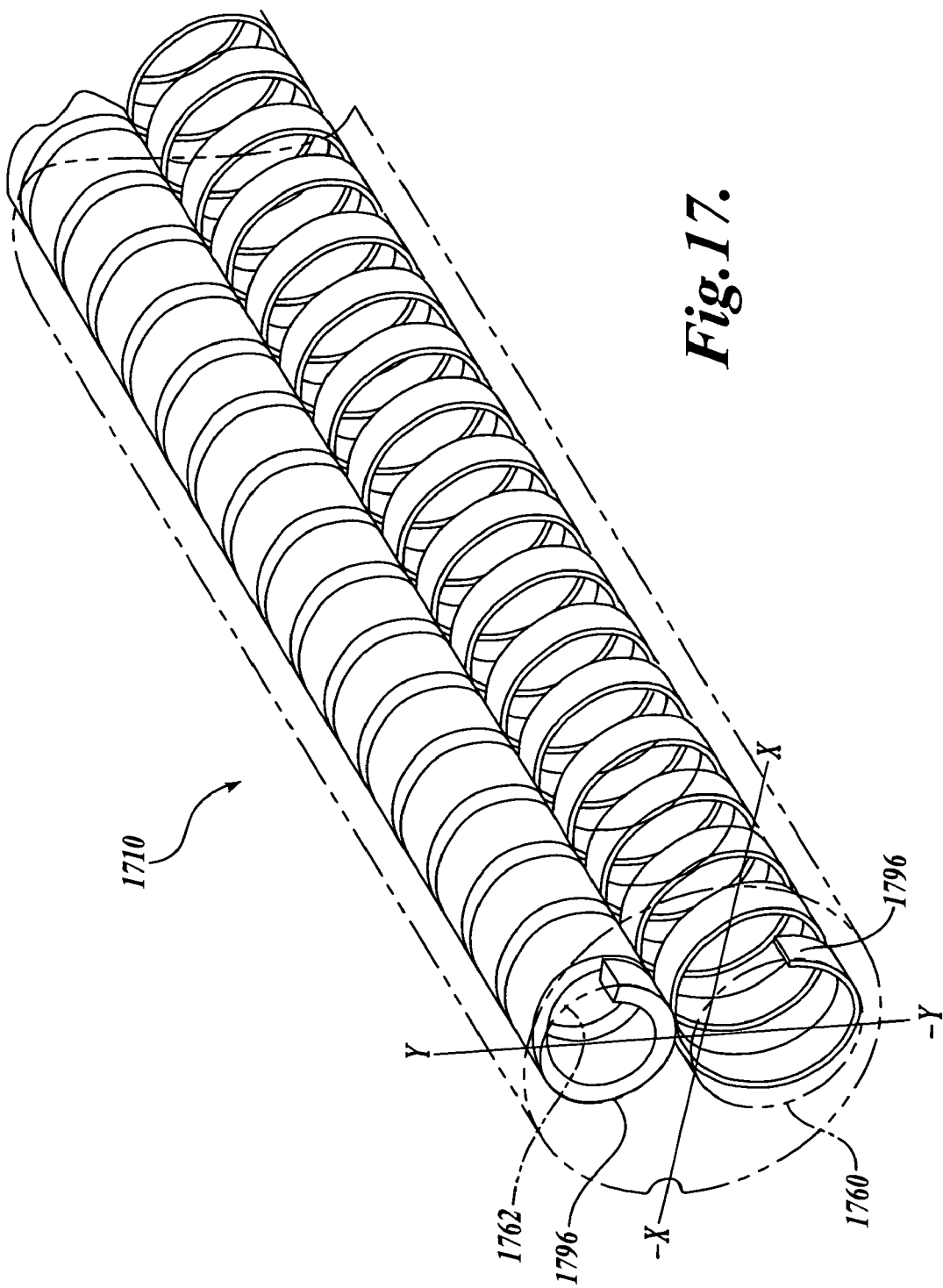
FIG. 17 is a partial view of the distal end of another embodiment of a catheter that is suitable for used in the system illustrated in FIG. 1.

FIG. 17 illustrates another embodiment of a catheter 1710 having a deflectable distal portion. In this embodiment, the catheter is constructed from a very flexible plastic extrusion with multiple lumens. The two main lumens, the working channel 1760 and the optical assembly channel 1762, are reinforced with coils 1796 to minimize out-of plane deflection. As shown in FIG. 17, the center of both lumens and both coils lie on the Y-axis to provide less resistance against deflection in the x-plane. When the steering wires (not shown) are pulled along the direction of the steering wire slots, the catheter will tend to bend about the y-axis or in the x plane. The coils 1796 also prevent the lumen from kinking as the catheter deflection radius becomes tighter. The catheter 1710 may further include an outer braid and outer layer, as described in detail above.

Figure 18:
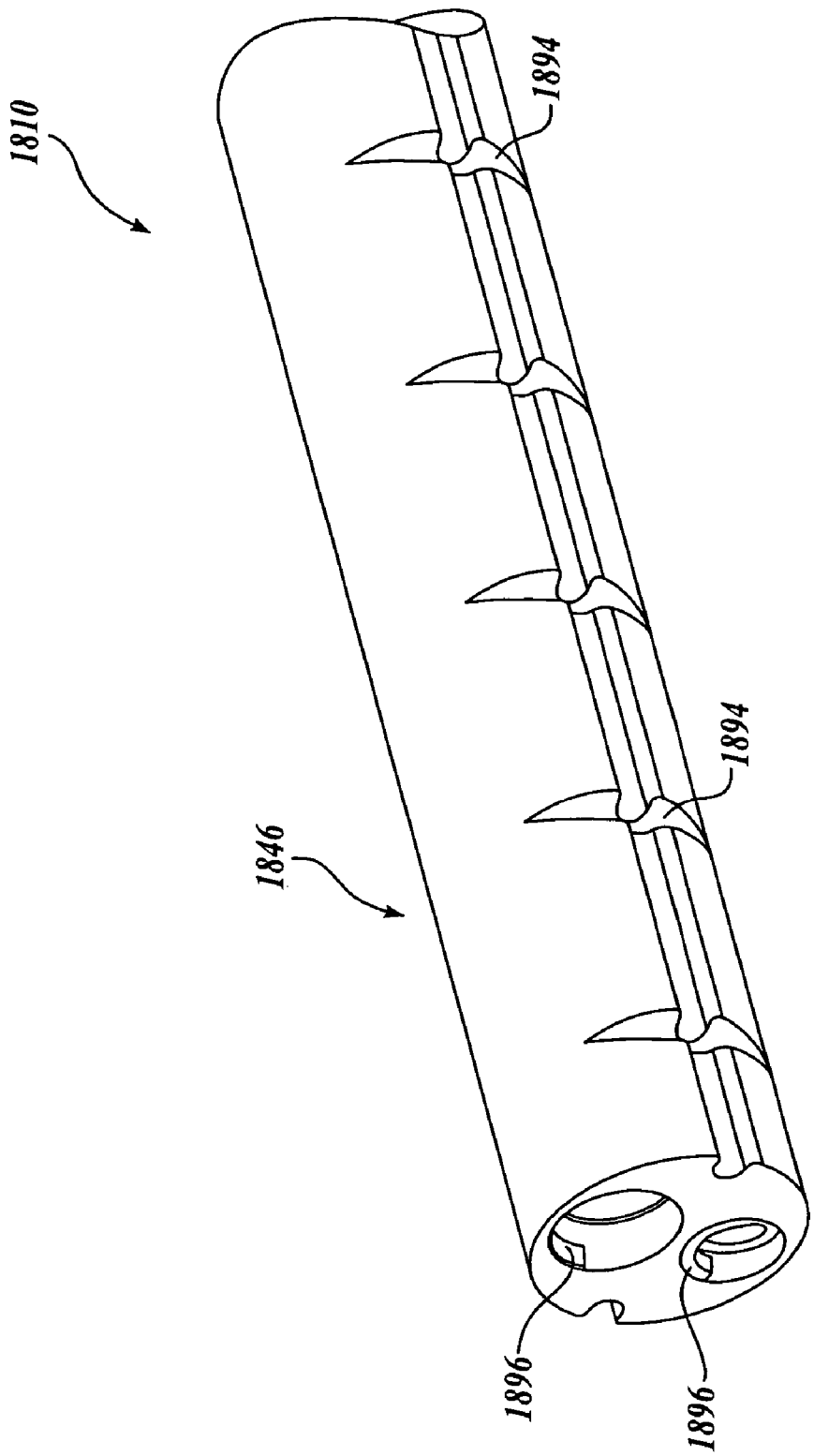
FIG. 18 is a partial view of the distal end of another embodiment of a catheter that is suitable for used in the system illustrated in FIG. 1.

FIG. 18 illustrates yet another embodiment of a catheter 1810 having a flexible distal portion 1846. In this embodiment, the multiple lumen extrusion is preferred to be flexible. Slots 1894 are cut on both sides of the extrusion to assist and bias the catheter 1810 in the preferred direction of deflection. As was described above, coils 1896 may be used to support the main lumens, if preferred, but are not required. The coil or coils can be useful if the slot cuts are deep to penetrate the main lumens. The coils could be used to line the lumens such that the devices do not inadvertently get caught against the slots. The catheter may further include a braided sheath and outer sleeve, as described above.

Returning now to FIGS. 1-4, the elongated body 38 of the catheter 10 includes a lumen 64 that holds an optical assembly 40 or portions thereof, as described briefly above. The optical assembly 40 is defined, e.g., by a cylindrical, elongated tubular member 24 and optic bundles 32, 34. The optical assembly 40 permits a user of the system 8 to view objects at or near the distal end 18 of the catheter 10. In the illustrated embodiment, the distal end 18 of the catheter includes a clear lens or window 22 that sealingly encloses the distal end of the lumen 64 to protect the optic bundles 32, 34 inside the lumen 16. The member 24 defines multiple lumens 26 that each contain one fiber optic bundle 32, 34. The first fiber optic bundle 32 illuminates the area or objects to be viewed, while the second fiber optic bundle 34 communicates the illuminated image to an eyepiece or ocular lens device 36 located at the handle 30 through which a user can view the images communicated via the fiber optic bundle. The handle 30 can also be configured to connect to a camera or imaging system such that users can save images and view them on a display. The fiber optic bundles 32, 34 each comprise one or more fiber optics cables, preferably multiple fiber optical cables, but may also include lenses, rods, mirrors, hollow or solid light guides, etc. The bundles 32, 34 are attached to the lens 22 with a clear adhesive, bond, or other connection, but can also abut the lens or be located adjacent the lens without any attachment. In an alternative embodiment, the lens 22 is not attached to the distal end 18 of the catheter, but is instead attached directly to the elongated member 24 and fiber optic bundles 32, 34.

As will be appreciated, the optical components of the catheter 10 may take many other forms and configurations. For example, the lumen 64 can include one fiber optic bundle for communicating images and one or more single illumination fibers that are not fixed relative to each other by the elongated member 24. That is, the fibers can be freely located in the lumen 64. Additionally, the elongated member 24 can have more or less lumens 26 that contain more or less fibers and/or bundles for illuminating and/or communicating images. For example, in an alternative embodiment, a single fiber replaces one or both of the bundles 32, 34. Furthermore, the elongated body 38 need not include the lumen 64. For example, one or more optical fibers or bundles of fibers can be molded in the elongated body 38. Alternatively, the elongated body 38 may include two lumens 64 for receiving separate fiber optic bundles 32 and 34, respectively. Possible alternative known configurations for the optical assembly 40 are described in U.S. Pat. Nos. 4,782,819; 4,899,732; 5,456,245; 5,569,161; and 5,938,588, the entire disclosures of which are hereby incorporated by reference.

In the illustrated embodiment, the tubular optical assembly 40 is part of the disposable catheter assembly defined by the catheter 10 and hub 20. Hence, the tubular optical assembly 40 and its fiber optic bundles 32, 34 extend from the distal end 18 of the catheter 10 to the opposing, proximal end 16 of the catheter 10, and then through the hub 20. As is illustrated in FIG. 1, the hub 20 includes a fiber optic connector 72 in which the fiber optic bundles 32, 34 terminate. The fiber optic connector 72 is a mechanical device that provides a detachable optical connection between the fiber of the optical assembly 40 and the fiber or lens system of the handle 30. Thus, the optical assembly 40 extends continuously through the disposable catheter 10 and hub 20, without interruption, to the fiber optic connector 72. In one embodiment, the fiber optic connector 72 is a detachable, simple point-to-point connection or splice. In other embodiments, the connector 72 is a more complex design having multi-port or other types of optical connections. For example, the connector 72 can be configured to redistribute (combine or split) optical signals, such as with an active or passive fiber optic couplers, e.g., splitters, optical combiners, X couplers, star couplers, or tree couplers. The fiber optic connecter 72 can also include a micro lens, graded-refractive-index (GRIN) rods, beam splitters, and/or optical mixers, and may twist, fuse, and taper together the fiber optic bundles 32, 34. In other embodiments, such as those described below, the optical assembly 40 is not part of the disposable catheter 10.

Referring again to FIG. 1, the handle 30 is generally an endoscopic handle that connects to the connectors 70, 72 of the hub 20 such that a user of the system can view images communicated by the fibers of the catheter 10 and such that a user can controllably steer or deflect the distal end 18 of the catheter. The handle 30 includes one or more shafts 78 that connect to and interact with the fiber optic connector 72 and the wire connector 70. The handle 30 also includes a controller or actuator 74 by which a user can steer the distal end 18 of the catheter 10. In the illustrated embodiment, the handle 30 generally includes a pair of steering wires (not illustrated), each of which is associated with one of the steering wires 68 of the catheter 10. The wires of the handle 30 are connected to the controller 74 at one end and are connected at the other end to the wires 68 via the connector 70. To steer the catheter 10, a user actuates the controller 74, which causes the wires 68 to deflect, which in turn forces the distal end 18 of the catheter to deflect as illustrated in FIG. 1. In the illustrated embodiment, the controller 74 is a user-operated mechanical slide or rotatable lever that is adapted to pull and release the wires 68 connected to the handle 30 by the connector 70. In an alternative embodiment, the controller 74 may take other forms, such as a rocker arm or rotating knob, adapted to pull and release the wires. In another alternative embodiment in which the catheter 10 has two or more pairs of steering wires, the handle 30 includes additional actuators and corresponding controls to drive the additional pairs of steering wires. In one embodiment, the handle 30 includes a locking mechanism, such that when a curve is activated by the controller 74, the curve may be locked in place. The use of wires to steer a tip of a catheter is well-known. Suitable examples are set forth in U.S. Pat. Nos. 4,899,723; 5,273,535; 5,624,397; 5,938,588, 6,544,215, and International Publication No. WO 01/78825 A2, the entire disclosures of which are hereby incorporated by reference.

As is described above, the handle 30 includes steering wires and fiber optics that connect to the steering wires 68 and fiber optic bundles 32, 34 of the catheter 10 via the connectors 70, 72. As will be appreciated, the handle 30 may be battery powered or connect to a power supply. The handle 30 also includes a light source, or connects to a light source, that illuminates the fiber bundle 32. In addition, the handle 30 has an eyepiece 80 for a user to view an image transmitted by the image bundle 34 from the distal end 18.

Referring again to FIG. 1, the hub 20 also includes connectors or ports 50 that each communicate with one of the lumens 62 of the catheter 10, as well as a connector or port 52 that communicates with the working channel 60. The connectors 50, 52 are preferably integral with the hub 20 and thus are disposable with the hub 20 and catheter 10. In the illustrated embodiment, connector 72 is separate from the connector 70 and connects to two separate portions, shafts, or projections of the handle 30. In an alternative embodiment, the connectors 70 and 72 are combined into a single connector that interfaces with a single portion of the handle 30, such that the optics handle and actuator for steering are disconnectable as a unit and reusable.

Figure 6:
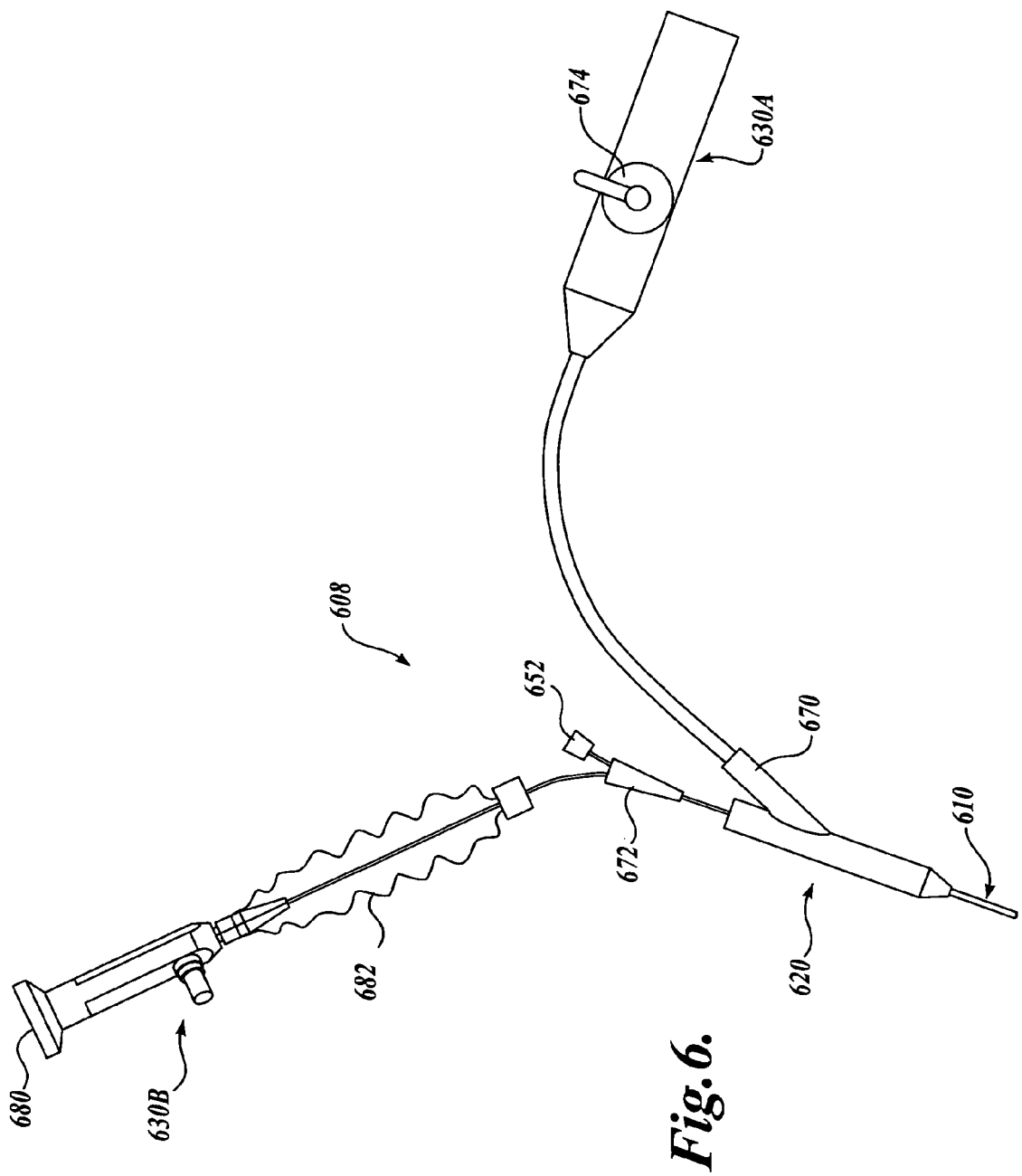
FIG. 6 is an assembly view of an optical catheter system according to another embodiment of the invention.

In a further embodiment of a system 608 in which the connectors 670 and 672 are separate connectors, such as is illustrated in FIG. 6, the optical catheter system 608 includes a first handle 630A that steers the catheter 610 and a second handle or component 630B having the eyepiece 680 through which the user can view images communicated by the catheter optics. In this embodiment, the first handle 630A connects to the connector 670 and the second handle 630B connects to the connector 672 to couple and decouple from the fiber bundle in the catheter 610. The handle 630A may be disposable, while the handle 630B is reusable. The handle 630B includes a sleeve 682, such as an extrusion over the fiber optic/illumination fiber component of the handle, to protect fiber sterility and prevent damage during the procedure due to the miniature nature of the fiber.

As will be appreciated from the foregoing, the optical catheter system 8 (See FIG. 1) in accordance with one embodiment of the present invention includes a sterile, single-use, disposable optical catheter 10, a sterile, single-use, disposable hub 20, and a reusable handle 30 for viewing images and steering the catheter. Because the catheter 10 and hub 20 are disposed of after a procedure, delays and costs associated with cleaning, sterilizing, and maintaining conventional scopes are avoided.

Set forth below is a description of an exemplary clinical application of the optical catheter system 8 according to the invention. The sterile single-use catheter 10 and hub 20 are removed from a factory package and then connected to the reusable handle 30 via the connectors 70 and 72. A guidewire is advanced into the urinary tract and the catheter 10 with or without a dilator is inserted over the guidewire. The guidewire may be withdrawn. The catheter 10 is then steered with the controller 74 to deflect the distal end 18 to the desired location in the kidney. The connectors/ports 50 and 52 are then associated with various working device and irrigation lines, as needed, and the desired treatment and/or diagnosis are performed. The catheter 10 is then withdrawn and discarded.

Figure 7:
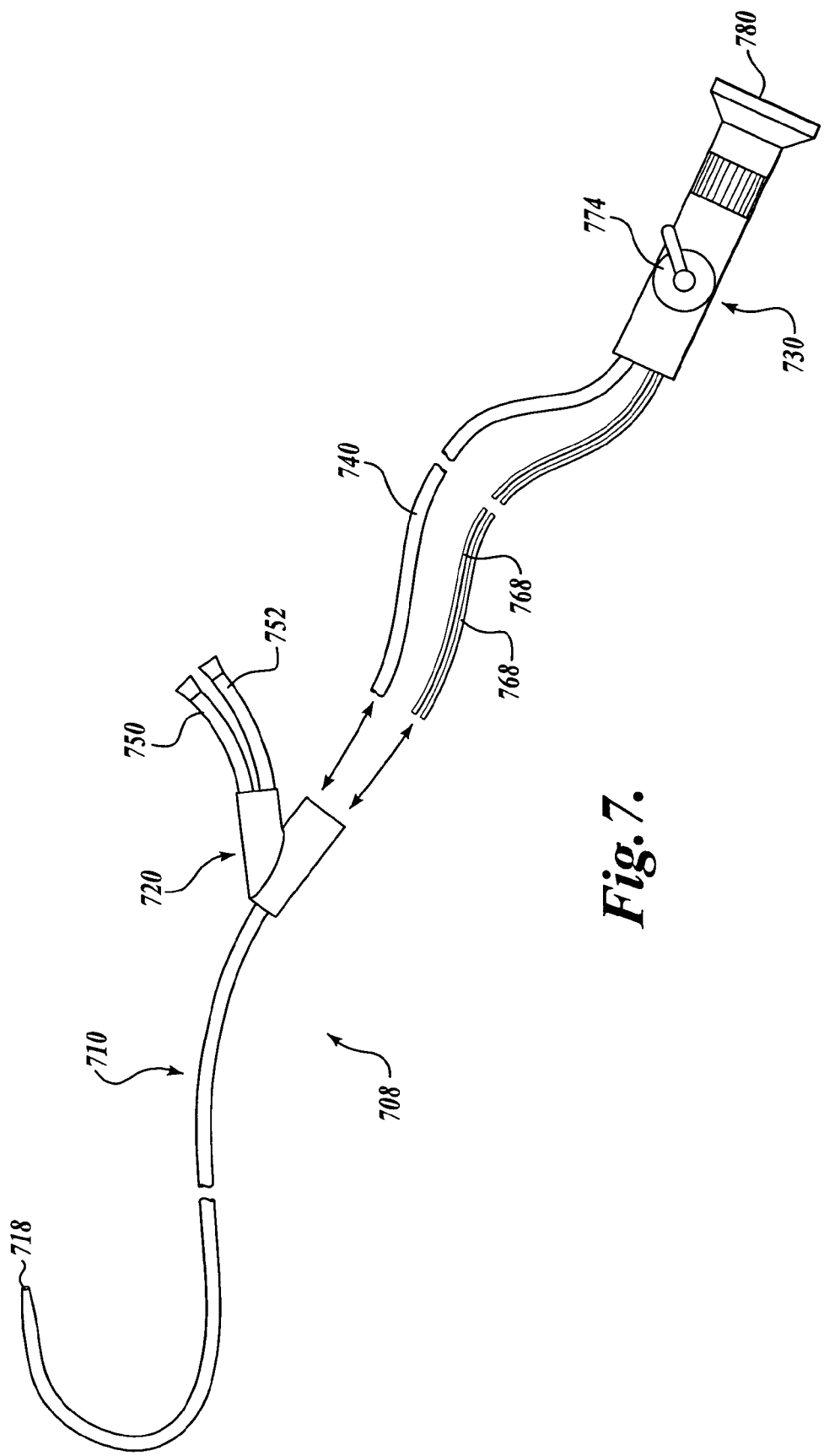
FIG. 7 is an assembly view of an optical catheter system according to a further embodiment of the invention.

In an alternative embodiment of the optical catheter system 708 illustrated in FIG. 7, the optical assembly 740 is not attached to the distal end 718 of the catheter and instead extends from the distal end 718, through the hub 720, and into the handle 730 without interruption. Additionally, the steering wires 768 extend from the distal end 718, through the hub 720, and into the handle 730 without interruption. When fully inserted into the catheter 710, the steering wires 768 each attach to the distal end 718 of the catheter 710 such that movement of the wires causes the distal end 718 to deflect in a controllable manner. The steering wires 768 attach to the distal end 718 of the catheter with a detachable connection (not shown), such as a snap or quick lock connection, that permits the steering wires to be easily detached from the distal end 718 after use of the catheter such that the wires can be withdrawn from the catheter. In this embodiment, the system 708 does not include the optical and wire connectors, and the wires 768 and optical assembly 740 are not disposable. That is, the wires 768 and optical assembly 740 are part of the reusable handle 730. Hence, in this embodiment, the lumens and channels of the elongated body receive the elongated wires 768 and elongated optical assembly 740 of the reusable handle 730b. The catheter 710 and hub 720 are still disposable.

Figure 8:
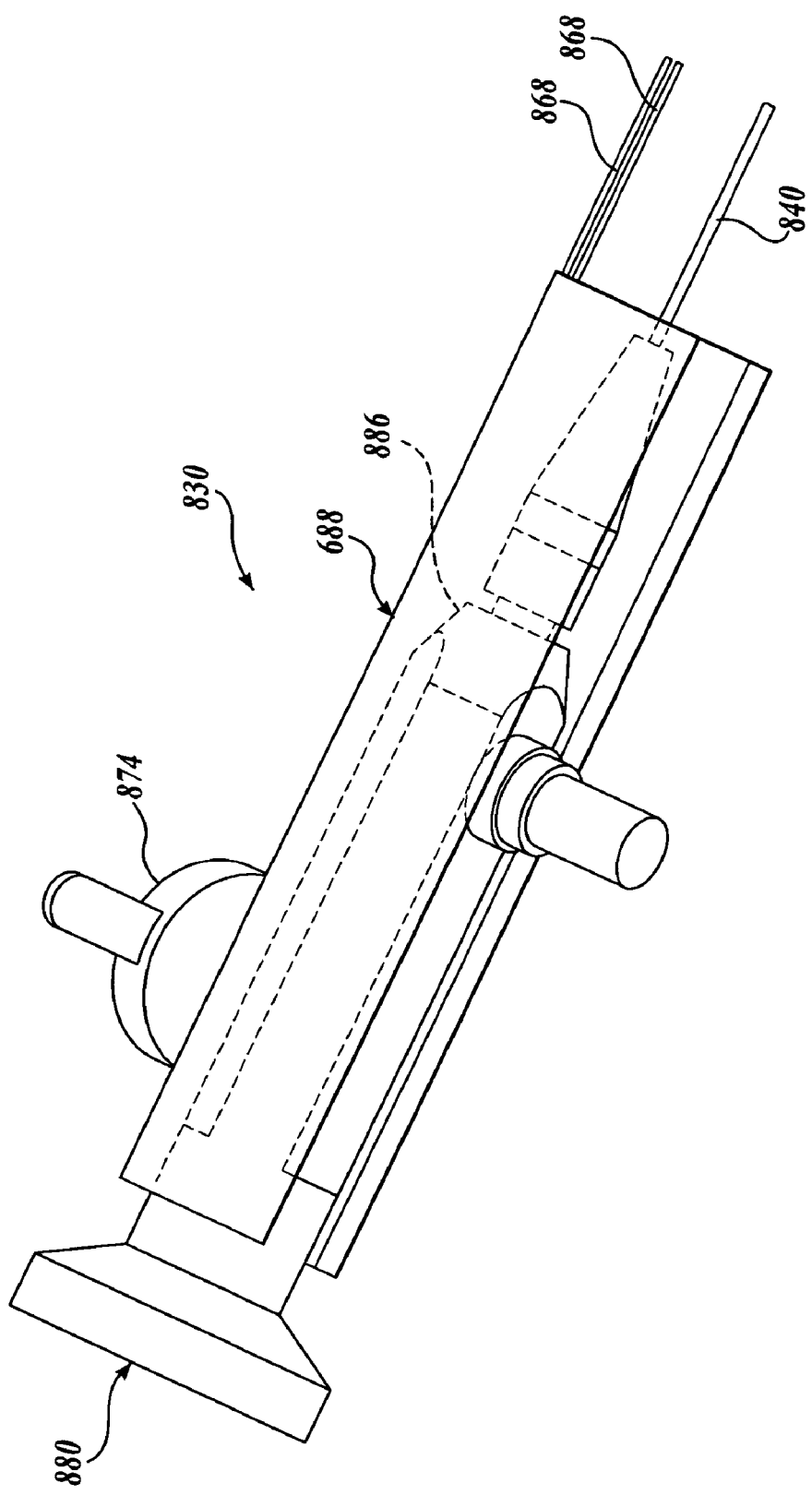
FIG. 8 is a perspective view of one embodiment of a handle of the optical catheter system illustrated in FIG. 7.

FIG. 8 illustrates an alternative embodiment of a handle 830 suitable for use with an optical catheter system 8. The handle 830 includes an optical portion 686 and a snap-on, slide-on, or clip-on steering portion 688. The optical portion 686 is the same as that of the handle 30 (see FIG. 1), but does not include the features for steering the catheter 10. The steering portion 688 is the same as that of the handle 30 (see FIG. 1), but does not include the optical features of the handle 30. The steering portion 688 may be disposable or reusable. The optical portion 680 is reusable.

Figure 9:
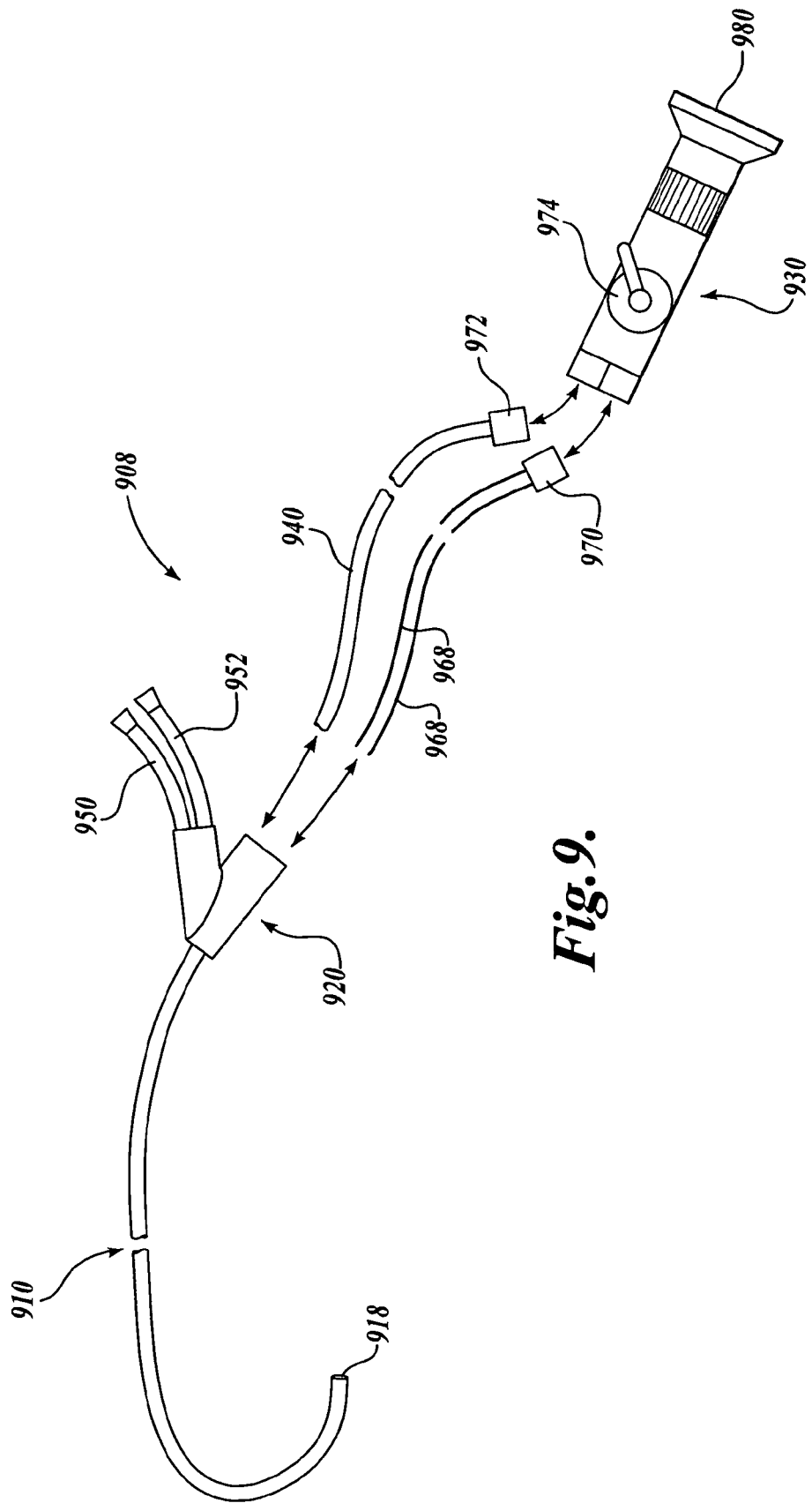
FIG. 9 is an assembly view of an optical catheter system according to another embodiment of the invention.

In a further embodiment of the optical catheter system 908 illustrated in FIG. 9, the connectors 970 and 972 are not part of the hub 920, but are respectively attached to the optical assembly 940 and the steering wires 968. The fibers of the optical assembly 940 are not attached to the distal end 918 of the catheter 910 and, when inserted into catheter, extend from the distal end 918, through the hub 920, and terminate at the connector 972, which is integral with the optical assembly. The reusable handle 930 is configured to connect directly to the connector 972 of the optical assembly and functions as described above. When fully inserted into the catheter 910, the steering wires 968 each attach to the distal end 918 of the catheter 910 such that movement of the wires causes the distal end 918 to deflect in a controllable manner. The steering wires 968 attach to the distal end 918 of the catheter with a detachable connection, such as a snap or quick lock connection, that permits the steering wires to be easily detached from the distal end 918 after use of the catheter such that the wires can be withdrawn from the catheter. When inserted into the catheter 910, the wires 968 extend from the distal end 918, through the hub 920, and terminate at the connector 970, which is integral with the wires. Hence, the wires 968 and the connector 970 form a control wire assembly. The handle 930 is configured to connect directly to the connector 970 of the steering wire assembly and function as described above. In this embodiment, the optical assembly 940 (and its connector 972) and the wires 968 (and their connector 970) are both disposable. The optical assembly 940 and its connector 972, and the wires 968 and their connector 970 may be sterilely packaged separately or in combination with the catheter 910.

Figure 10:
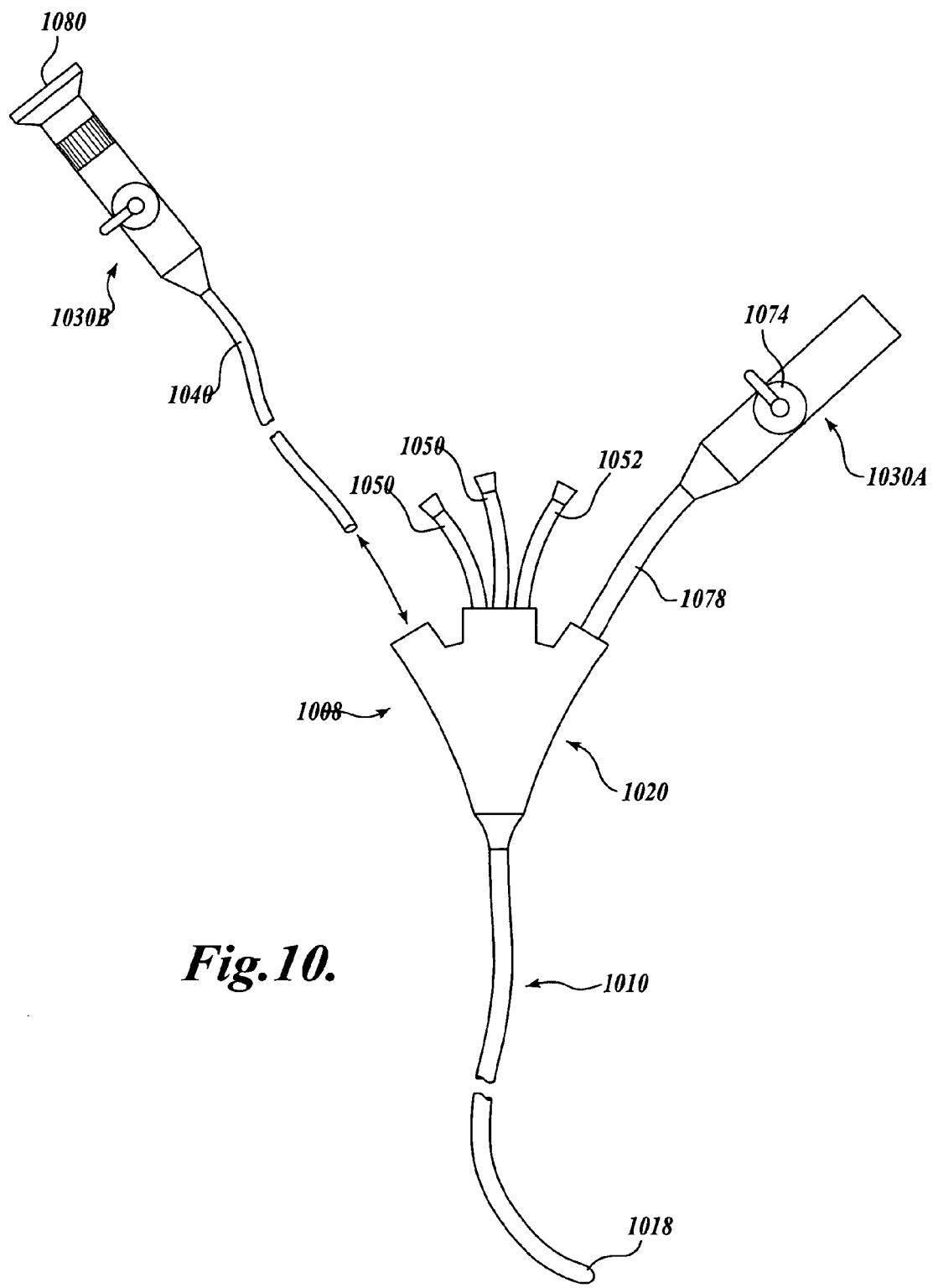
FIG. 10 is an assembly view of an optical catheter system according to a further embodiment of the invention.

FIG. 10 illustrates an additional embodiment of an optical catheter system 1008 of the present invention. In this embodiment, the handle 1030 for steering the catheter 1010 is integral with the hub 1020 and catheter 1010, and are together packaged as a single-use, sterile, disposable assembly. The optical handle 1030B and its optical assembly 1040 are reusable. Hence, the optical assembly 1040 is received by the hub 1020 and catheter 1010 for use, and then removed therefrom after the procedure has been performed. The steering wires of the handle 1030A are attached to the distal end 1018 of the catheter 1010 and extend from the distal end 1018, through the hub 1020, and into the handle 1030A without interruption. In this embodiment, the system 1008 does not include the optical fiber and steering wire connectors, and the optical assembly 1040 is part of, i.e., integral with, the reusable handle 1030B.

Figure 11:
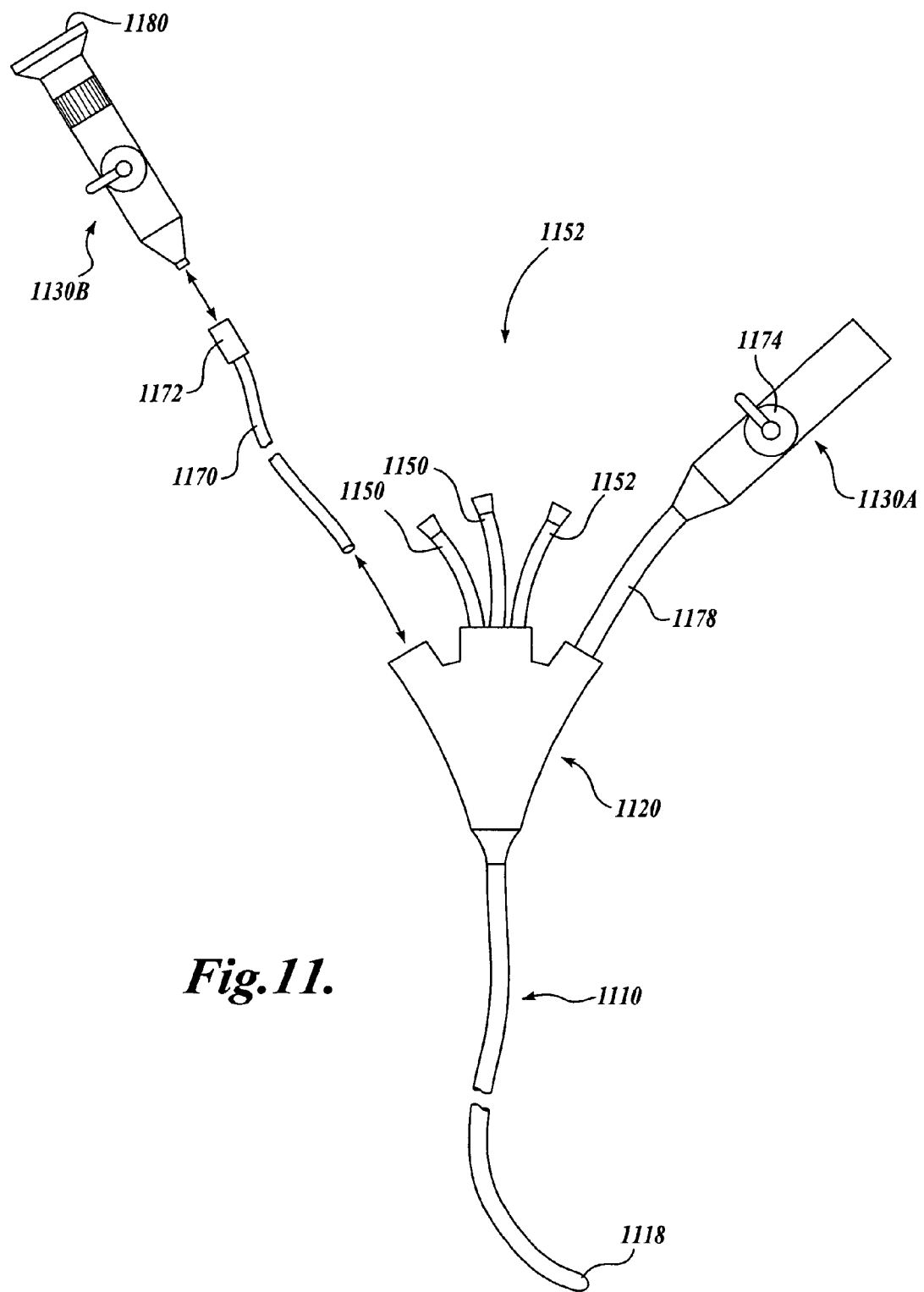
FIG. 11 is an assembly view of an optical catheter system according to an additional embodiment of the invention.

FIG. 11 illustrates an additional embodiment of an optical catheter system 1108 of the present invention. In this embodiment, the handle 1030A for steering the catheter 1110 is integral with the hub 1020 and catheter 1110, and are together packaged as a single-use, sterile, disposable assembly. The optical handle 1030B is reusable and is connectable to the disposable optical assembly 1140 via a connector 1172. Hence, the optical assembly 1140 is disposable with the integral assembly defined by the handle 1130A, the hub 1120, and catheter 1110, and may also be packaged with these items. The optical assembly 1140 is received by the hub 1120 and catheter 1110 for use, removed therefrom after the procedure has been performed, and then discarded with the handle 1130A, the hub 1120, and catheter 1110. The optical handle 1130B is reused. The steering wires of the handle 1130A are attached to the distal end 1118 of the catheter and extend from the distal end 1118, through the hub 1120, and into the handle 1130A without interruption. In this embodiment, the system 1108 does not include the steering wire connector, and the optical assembly 1140 is not integral with the reusable handle 1130B.

FIGS. 19A-19D and 20 illustrate another embodiment of an optical catheter system constructed in accordance with the present invention. As best shown in FIGS. 19 and 20, the optical catheter system includes a sterile, single-use, disposable catheter assembly 1912 (See FIGS. 19A-19D) and a resuable optical system 2040 (See FIG. 20). The catheter assembly 1912 includes a handle 1930A and a catheter 1910. The optical system 2040 includes an optical handle 2030B connected to an optical cable 2042. The optical handle 2030B, in one embodiment, may comprise an image viewing device, such as an ocular 2080, and a coupler 2084.

As best shown in FIG. 19, the catheter 1910 is functionally connected to the catheter handle 1930B. The catheter 1910 may be any suitable catheter for use in vivo, such as any one of the catheters described in detail herein. The handle 1930A includes a handle housing 1932 to which a steering mechanism 1974, optional lock mechanism 1976, and one or more ports 1958, 1960 are operatively connected. In one embodiment, the handle housing 1932 comprises an upper, proximal section 1934 and a lower, distal hub 1936. In the embodiment shown in FIG. 19A, the distal hub 1936 of the handle housing is Y-shaped. The Y-shaped hub 1936 includes a distal stem section 1938 to which the proximal end 1912 of the catheter 1910 is functionally connected. The Y-shaped hub 1936 further includes first and second branch sections 1940 and 1942, the first branch section 1940 is connected to the distal end of the housing upper section 1934 while the second branch section 1942 includes an opening through which an interior channel of the catheter, such as the working channel, may be accessed. The first branch section 1940 may be connected to the upper section 1934 in such a manner as to permit free or limited rotation of the Y-shaped hub 1936 with respect to the housing upper section 1934 about a longitudinal axis of the handle 1930A. In one embodiment, this may be accomplished by a circular flange (not shown) formed at the proximal end of the first branch section and being captured in a cooperating slot (not shown) formed by the distal end of the housing upper section.

Figure 19A:
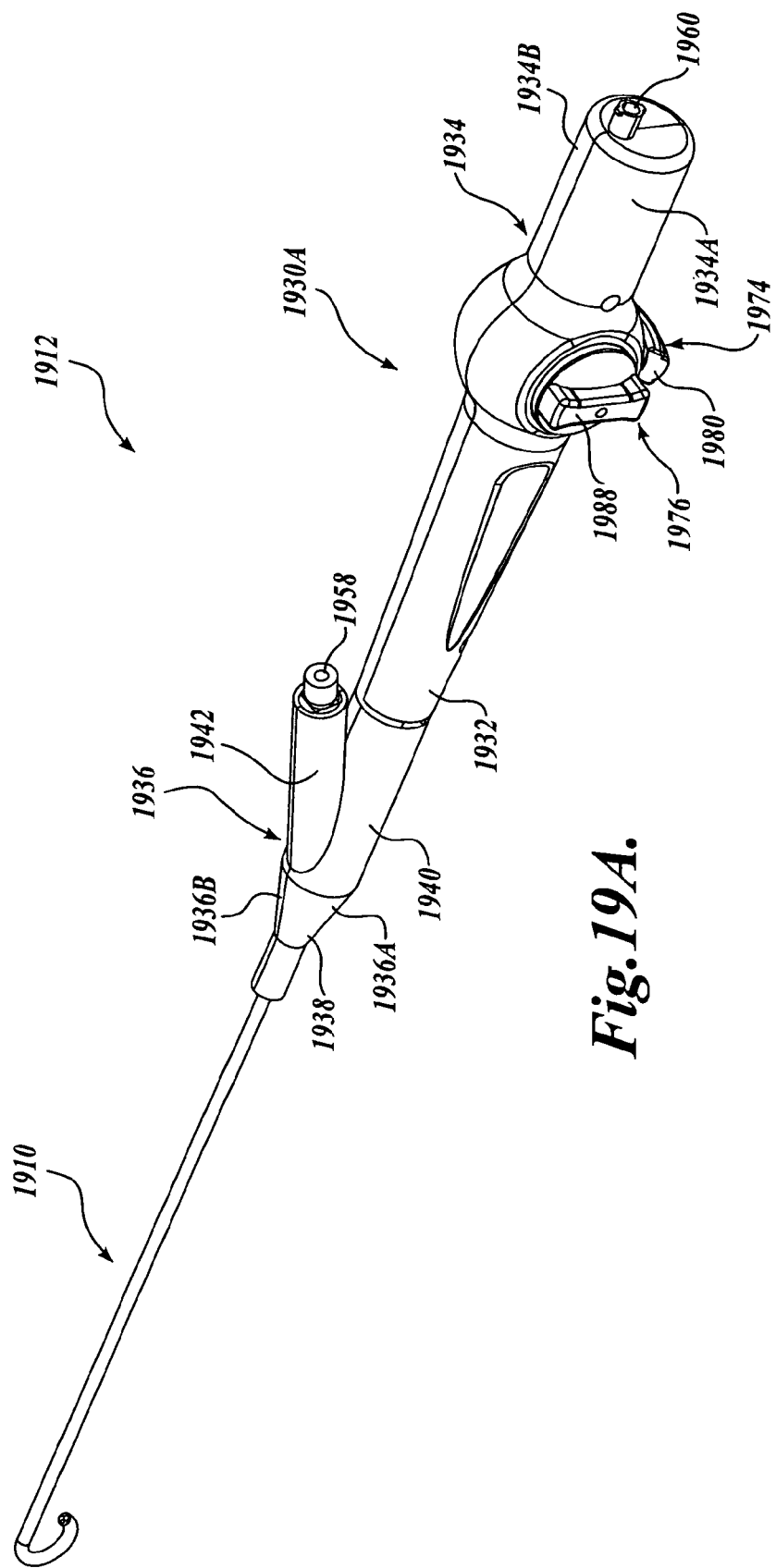
FIG. 19A is a perspective view of one suitable embodiment of a catheter assembly suitable for use in an optical catheter assembly.

In one embodiment, handle housing sections are formed by housing halves 1934A and 1934B and 1936A and 1936B joined by appropriate removable fasteners, such as screws, or non removable fastening techniques, such as heat bonding, ultrasonic welding or adhesive bonding. As best shown in FIG. 19A, the housing halves (only 1936B is shown) of the Y-shaped hub 1936 define respective passageways 1948 and 1950 for communicating with the remainder of the handle housing 1934 and exterior the handle, respectively. The handle 1930A further includes a bifurcation 1954. The bifurcation 1954 is preferably insert molded to connect the proximal end 1916 of the catheter 1910 and its lumens to the working channel port 1958 and optical assembly port 1960. In embodiments where the bifurcation 1954 is insert molded, the catheter steering wires 1968 are sleeved with a PTFE sleeve or a metal sleeve or similar coiled or braided tube such that molten polymer from the bifurcation process will bond to the sleeve and allow the steering wire within the sleeve to move respectively therein.

As was described above, the handle housing 1932 includes one or more ports 1958 and 1960 for providing access to the respective channels of the catheter 1910. In the embodiment shown, the ports include, but are not limited to, a working channel port 1958 and an optical assembly port 1960. The ports may be defined by any suitable structure. For example, the working channel port 1958 and the optical assembly port 1960 may be defined by fittings 1962 and 1964, respectively, such as luer fittings, that may be bonded or otherwise secured to the handle housing 1932 when assembled. In one embodiment, the housing halves may define cooperating structure that securely locks the fittings 1962 and 1964 in place when assembled. The fitting 1962 and 1964 are connected to the appropriate catheter channels via tubing 1966, as best shown in FIG. 19C. In one embodiment, the handle 1930A also includes a loop hub 1970 interconnected between the optical assembly port 1960 and the tubing 1966. The loop hub 1970 has an oversized chamber to allow the optical cable of the optical system to be deflected to account for the change (shortening) in catheter length when the distal end of the catheter is deflected by the steering wires 1968.

Figure 19B:
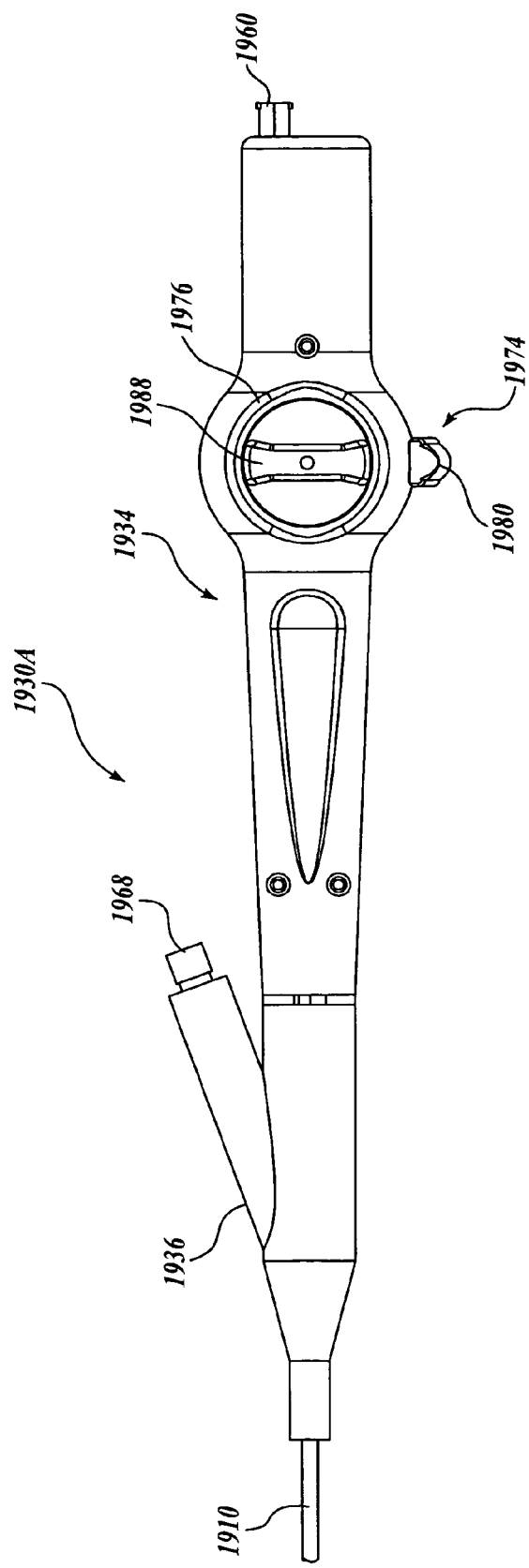
FIG. 19B is a top view of the catheter assembly shown in FIG. 19A.
Figure 19C:
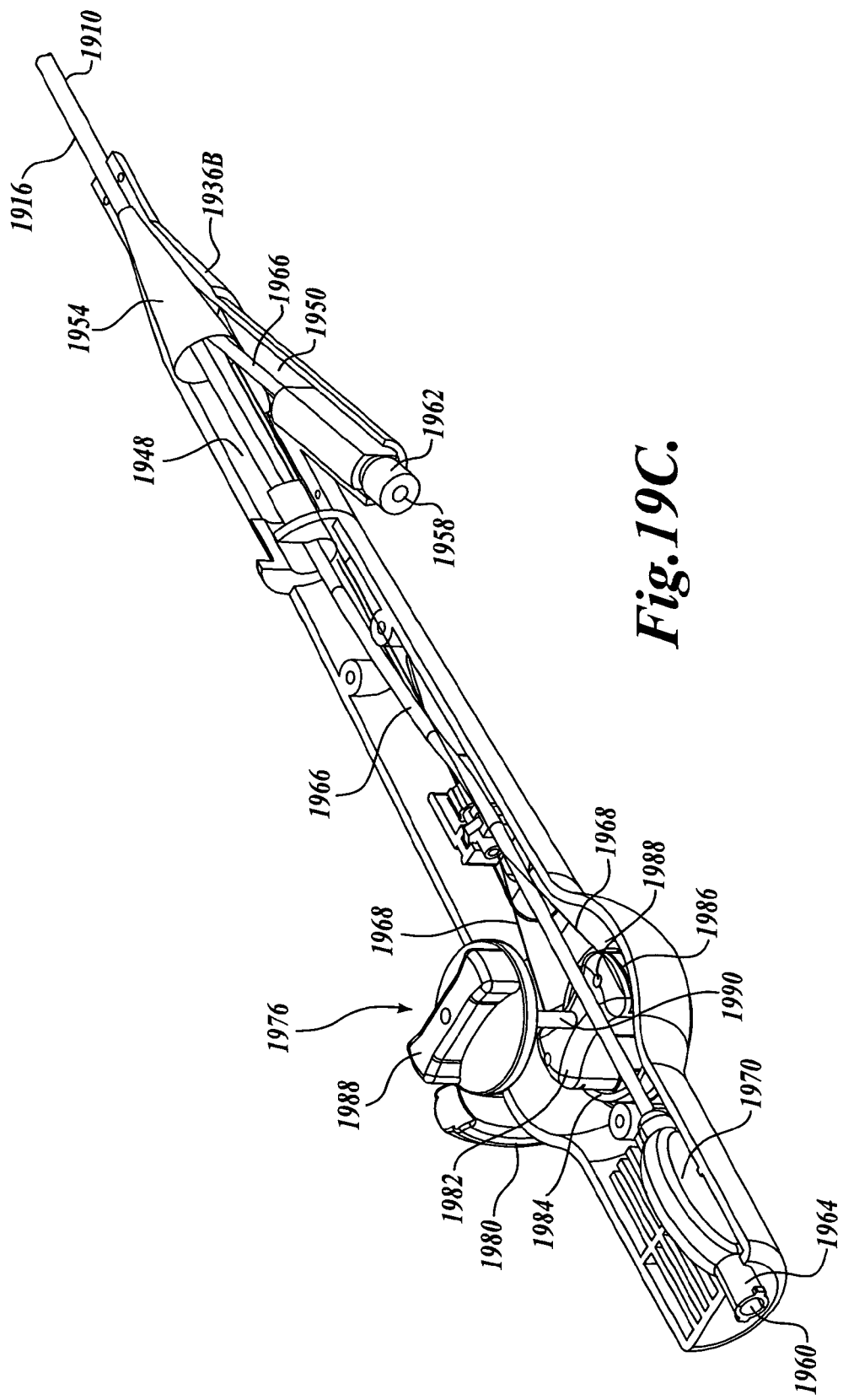
FIG. 19C is a perspective cross section view of the catheter assembly shown in FIG. 19A.

The catheter handle 1930A may also include a steering mechanism 1974, as best shown in FIGS. 19A and 19B. The steering mechanism 1974 of the catheter handle 1930A controls the deflection of the distal end 1918 of the catheter 1910. The steering mechanism 1974 may be any known or future developed mechanism that is capable of deflecting the distal end of the catheter by selectively pulling one or more steering wires 1968. In the embodiment shown in FIGS. 19A and 19B, the steering mechanism 1974 includes an activation lever 1980 for effecting 2-way steering of the catheter distal end in a single plane. By actuating the activation lever 1980 in one direction the distal end will deflect in one direction. Turning the activation lever 1980 in the other direction will deflect the catheter distal end in the opposite direction. It is preferred that the catheter distal end will travel in a single plane when sweeping from one direction to the other. The activation lever 1980 is connected to the distal end 1918 of the catheter 10 via steering wires 1968 (See FIG. 19C), respectively, that extend through the catheter 1910. While a manually actuated steering mechanism for effecting 2-way steering of the distal end is shown, it will be appreciated that a manually actuated steering mechanism that effects 4-way steering may be practiced with and is therefore considered to be within the scope of the present invention.

Referring now to FIGS. 19A-19D, there is shown one embodiment of the steering mechanism 1974 that may be practiced with the present invention. The steering mechanism 1974 includes the activation lever 1980 secured for rotation with a pulley 1982. The pulley 1982 is rotatably supported by a boss 1984 integrally formed or otherwise positioned to extend into the interior of the handle housing 1932 in a fixed manner from the housing half 1934B. The pulley 1982 is either integrally formed or keyed for rotation with the activation lever 1980. The proximal ends of one pair of steering wires 1968 are connected to opposite sides of the pulley 1982 in a conventional manner. In the embodiment shown, the steering wires 1968 are placed into respective slots 1986 and secured thereto by suitable fasteners, such as set-screws 1988. Each set-screw pinches the steering wires 1968 against the pulley 1982 to secure it in place. When assembled, the pulley 1982 provides control of the distal end 1918 of the catheter 1910 in two directions. In these embodiments, the catheter 1910 is straight in the neutral position.

Figure 19D:
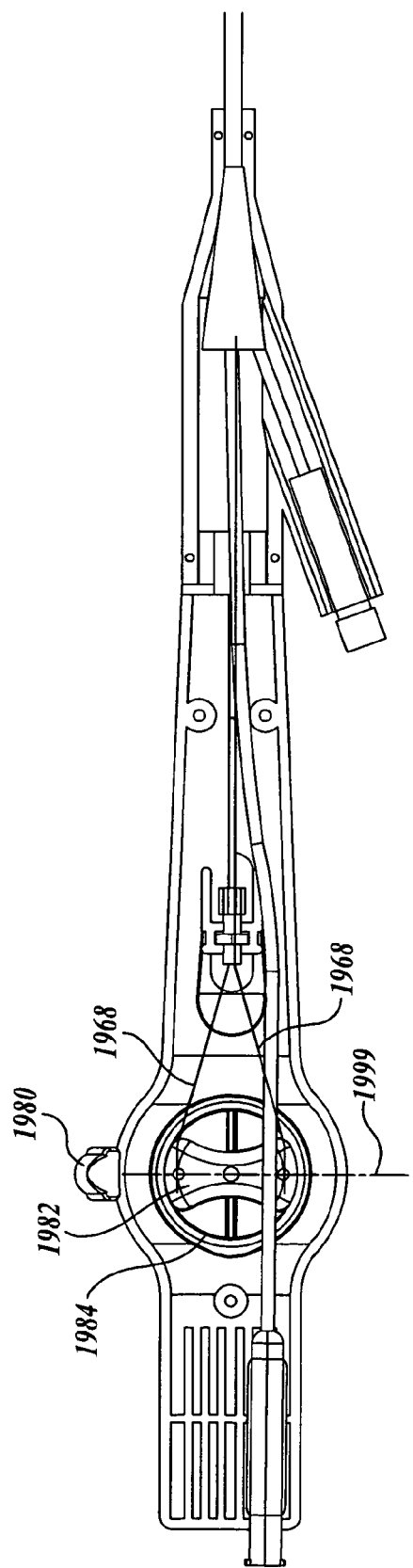
FIG. 19D is a top cross section view of the catheter assembly shown in FIG. 19A.

It will be appreciated that the steering mechanism may be configured such that the direction of catheter deflection in both directions is either equal or such that preferential one side deflection is realized (e.g., 180 degree deflection in one direction vs. 90 degree deflection in the other, etc.). For equal directional deflection, the steering wires 1968 are of equal length when the catheter is in the neutral (i.e., straight or unbent) position and are attached to the pulley 1982 at positions located along an axis of the pulley that is perpendicular to the longitudinal axis of the catheter, as best shown in FIG. 19D. For unequal angles of deflection, the steering wires are not equivalent in length and the steering wires are attached to the pulley in other positions around the circumference thereof. As will be appreciated, the catheter side related to the side with the greater steering wire displacement will deflect to the greater angle. In embodiments where there is only a single deflection of the shaft required, a single pull wire system may be used. The steering wire maybe attached to the pulley at a position proximal the perpendicular axis of the pulley to maximize the full swing of the pulley.

In other embodiments, it is also understood that changes could be made to the design to achieve a mechanical advantage such as to increase the diameter of the pulley for a longer steering wire displacement length. Other configurations that achieve a mechanical advantage may also be used. For example, instead of the steering wires terminating at the pulley, the steering wires may be wrapped around pins positioned on the pulley and then anchored on the handle at points distal the pulley. In this case, the steering wires will displace up to twice its normal distance when compared to the device shown in FIG. 19D. This feature may be used for larger diameter catheter deflection where longer steering wire displacement is utilized.

As best shown in FIGS. 19A-19D, the handle 1930A may further include a lock mechanism 1976 that functions to lock the catheter 1910 in a desired deflection position or apply tension on the pulley 1982 during use. The lock mechanism 1976 includes a tension knob 1988 that is actuatable between a locked position, selectively tensioned positions, and an unlocked position. As best shown in FIG. 19C, the tension knob 1988 is threaded onto a thread post 1990 extending from the activation lever 1980. The thread post 1990 extends through the handle housing to allow the tension knob 1990 to be externally mounted. In use, by tightening the tension knob 1990 on the thread post 1990 against the handle housing 1932 will also bring the activation lever 1980 into contact with the other handle housing half The user can adjust the tension of the activation lever 1980, as desired, by rotation of the tension knob 1990. Further tightening of the tension knob 1990 will prevent rotation of the activation lever 1980, thereby locking the steering wires 1968 in place, and in turn, locking the deflected position of the catheter 1910.

Figure 21:
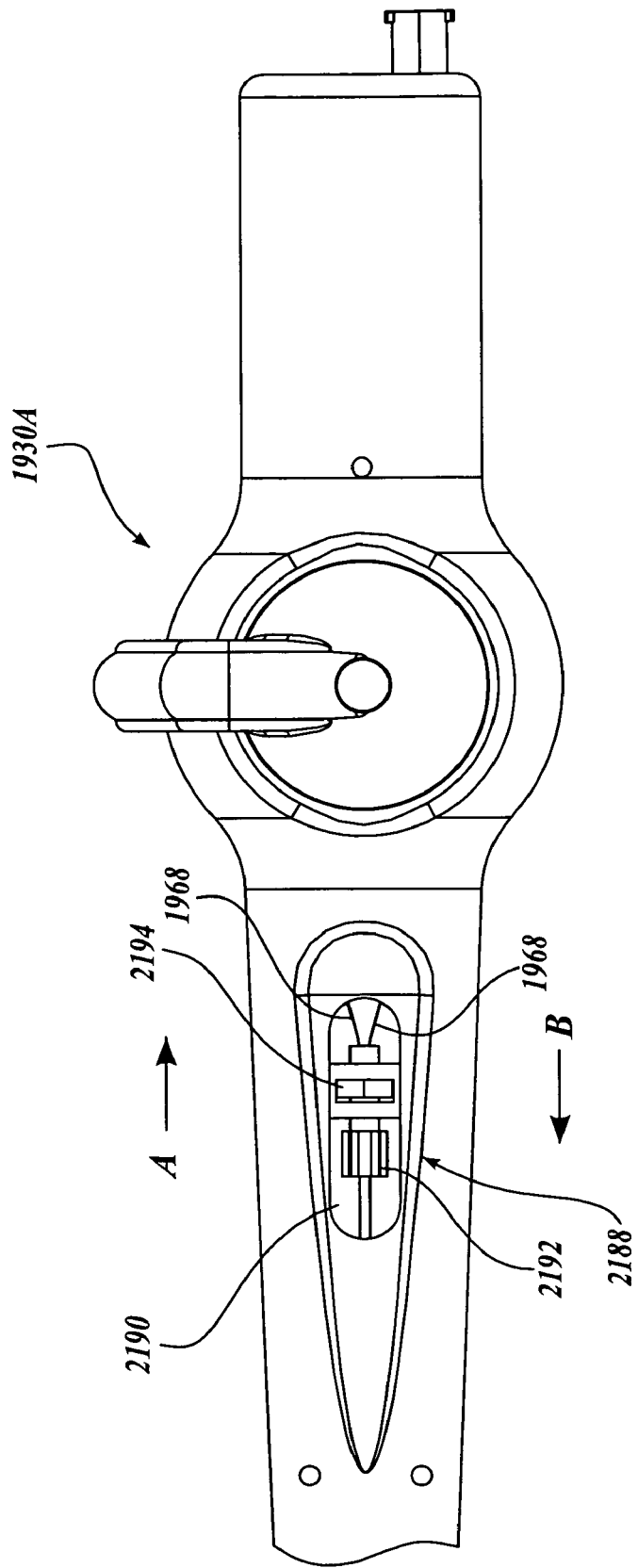
FIG. 21 is a partial bottom view of the catheter assembly shown in FIG. 19A

In accordance with another aspect of the present invention, it may be desirable to adjust the tensioning of the steering wires after the handle 1930A has been assembled. Turning now to FIG. 21, there is shown a handle having a tension adjustment assembly 2188 accessible from exterior the housing through a window 2190. The tension adjustment assembly includes an adjustment screw 2192 cooperatingly engaged with a stationary nut 2194. The nut 2194 may be held stationary and non-rotatable, for example, via molded structure in the handle housing. When assembled, the steering wires 1968 are threaded through the longitudinal lumen of the adjustment screw 2192. The adjustment screw 2192 is designed with teeth on the side of its head portion to allow a user to rotate the screw. Rotation of the screw to advance the adjustment screw 2192 in the direction of arrow A will increase steering wire tension while rotation of the screw for advancing the screw 2192 in the direction of arrow B will decrease tension on the steering wires 1968. Proper tension will allow quicker response of the steering wire to actuation of the activation lever.

Figure 22:
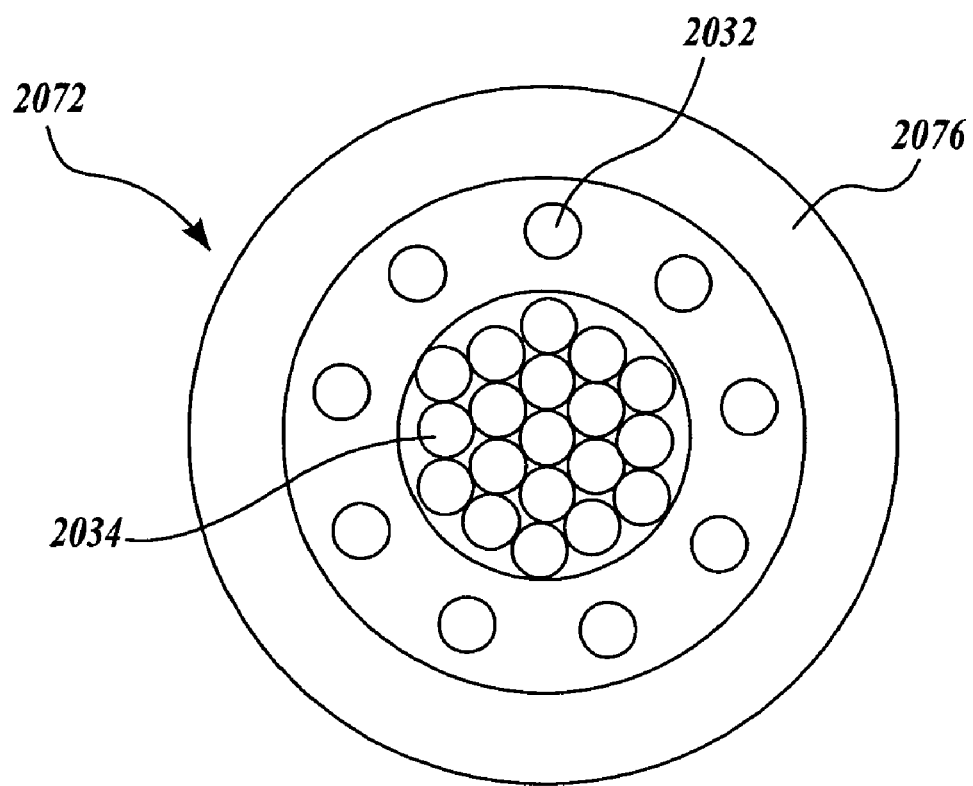
FIG. 22 is a cross sectional view of the imaging device cable of FIG. 20

As was discussed briefly above, a small diameter viewing device, such as a fiberscope or other imaging device, may be slidably routed through one channel (e.g., optical assembly channel) of the catheter 1910 to the distal end thereof. The viewing device permits the user of the optical catheter assembly to view objects at or near the distal end or tip of the catheter 1910. Turning now to FIG. 20, there is shown one suitable embodiment of a viewing device or optical assembly 2040 formed in accordance with aspects of the present invention. The optical assembly 2040 includes a fiber optic cable 2072 connected to an optical handle 2030B comprising a coupler 2084 and an ocular or eyepiece 2080. The fiber optic cable 2072 is defined, for example, by one or more optical fibers or bundles 2032 and 2034 encased by a cylindrical, elongated tubular sleeve 2076, as best shown in FIG. 22. The outer diameter of the fiber optic cable 2072 is preferably between 0.4 mm and 1.2 mm, although other sizes may be used depending on its application and the lumen size of the catheter. The tubular sleeve 2076 of the fiber optic cable 2072 may be constructed of any suitable material, such as nylon, polyurethane, polyether block amides, just to name a few. Additionally, a metallic hyptotube may be used.

In the illustrated embodiment, as best shown in FIGS. 20 and 22, the fiber optic cable 2072 includes one or more centrally extending coherent imaging fibers or fiber bundles 2034 and one or more circumferentially extending illumination fibers or fiber bundles 2032 (which may not be coherent) that generally surround the one or more imaging fibers of fiber bundles 2034. The fibers or fiber bundles 2032 and 2034 may be attached to the tubular sleeve 2076 via suitable adhesive. The distal end of the fiber optic cable 2072 includes a distal lens and/or window (not shown) that encloses the distal end to protect the fiber bundles. Alternatively, the optical assembly lumen of the catheter 1910 (See FIG. 19) may include a lens or window positioned at its distal end, as was described in detail above. The distal lens (not shown) also projects the image from the field of view onto the distal end of the image bundle 2034. The image bundle 2034 then transmits the image from the distal end of cable 2072 to the handle 2030B.

The optical assembly 2040 may have a stop collar or sleeve (not shown) to limit movement of the cable 2072 through the optical assembly channel of the catheter and limit the length by which the cable 2072 can extend beyond the distal end of the catheter 1910. The inner surface of the imaging channel of the catheter may have color markings or other calibration means to indicate to the user when inserting the cable 2072 that the end of the catheter is approaching or has been reached.

The proximal end of the fiber optic cable 2072 is functionally connected to the coupler 2084 of the handle 2030B. In use, the illumination fibers or fiber bundles 2032 illuminate the area or objects to be viewed, while the imaging fibers or fiber bundles 2034 communicates the illuminated image to an image viewing device, such as an eyepiece or ocular lens device 2080, connected to the coupler 2084 through which a user can view the images communicated via the imaging fibers or fiber bundles 2034. The eyepiece 2080 may either be permanently or detachably connected to the coupler 2084 as shown in FIGS. 23A and 23B. In one embodiment, the eyepiece 2080 is detachably connected via a snap fit connector 2098; however, other selectively detachable connectors may be used, such as male and female threaded connectors, quick lock connectors, bayonet connectors, to name a few. In this embodiment, the coupler 2084 and cable 2072 can be detached from the eyepiece 2080 after a procedure and discarded, while the eyepiece 2080 may be sterilized and reused. The optical handle 2030B can also be configured to connect to a camera or imaging system such that users can save images and view them on display. It will be appreciated that the handle 2030B may include other known components, such as adjustment knobs (not shown), that adjust the relative positioning of the lenses and, thus, adjusts the focus of the image transmitted through them. The coupler 2084 may also includes a light post 2086 that is connected to the proximal end of the illumination fibers or fiber bundle 2032. The light post 2086 is configured to be releasably connected to a light cable for supplying light from a light source external the optical assembly 2040 to the illumination fibers or fiber bundle 2032.

In one embodiment, the optical assembly may optionally include a contamination sleeve 2090 for protecting fiber sterility and preventing damage during the procedure due to the miniature nature of the fiber, as best shown in FIG. 20. The contamination sleeve 2090 when attached to the handle extends from the coupler 2084 distally to a section of the optical cable 2072. The end of the contamination sleeve 2090 terminates in a distal connector 2092. The distal connector 2092 is configured to connect to the optical assembly port of the steering handle 1930A, preferably in a sealable manner.

Figure 24:
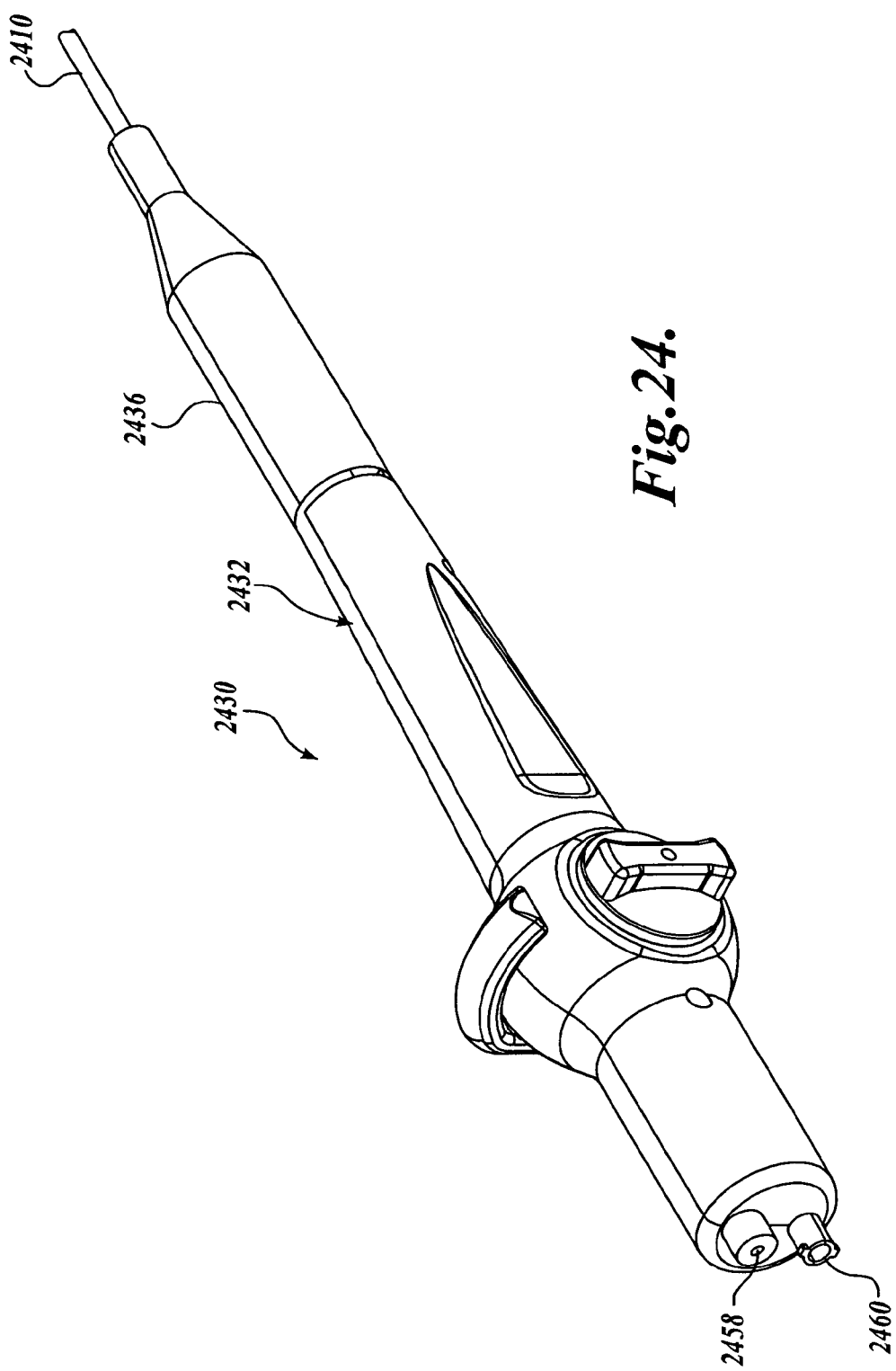
FIG. 24 is a perspective view of another catheter handle formed in accordance with aspects of the present invention.

FIG. 24 illustrates another embodiment of a catheter handle 2430 constructed in accordance with aspects of the present invention that is suitable for use with the catheter 1910 described above and shown in FIG. 19A. The catheter handle 2430 is substantially similar in construction, materials, and operation as the catheter handle 1930A described above and shown in FIGS. 19A-19D, except for the differences that will now be described. As best shown in FIG. 24, the distal hub section 2436 of the handle housing 2432 is not formed as a Y-shaped distal hub but instead is formed as a tapering cylindrical body. In this embodiment, both working channel and optical channel ports/luer connectors 2458-2460 are located at the proximal end of the handle housing 2432. The connectors 2458 and 2460 are connected in communication with the respective catheter channels via tubes (not shown). Since the Y-shaped distal hub is not required in this embodiment, the entire handle housing can be formed by two molded housing halves.

Figure 25:
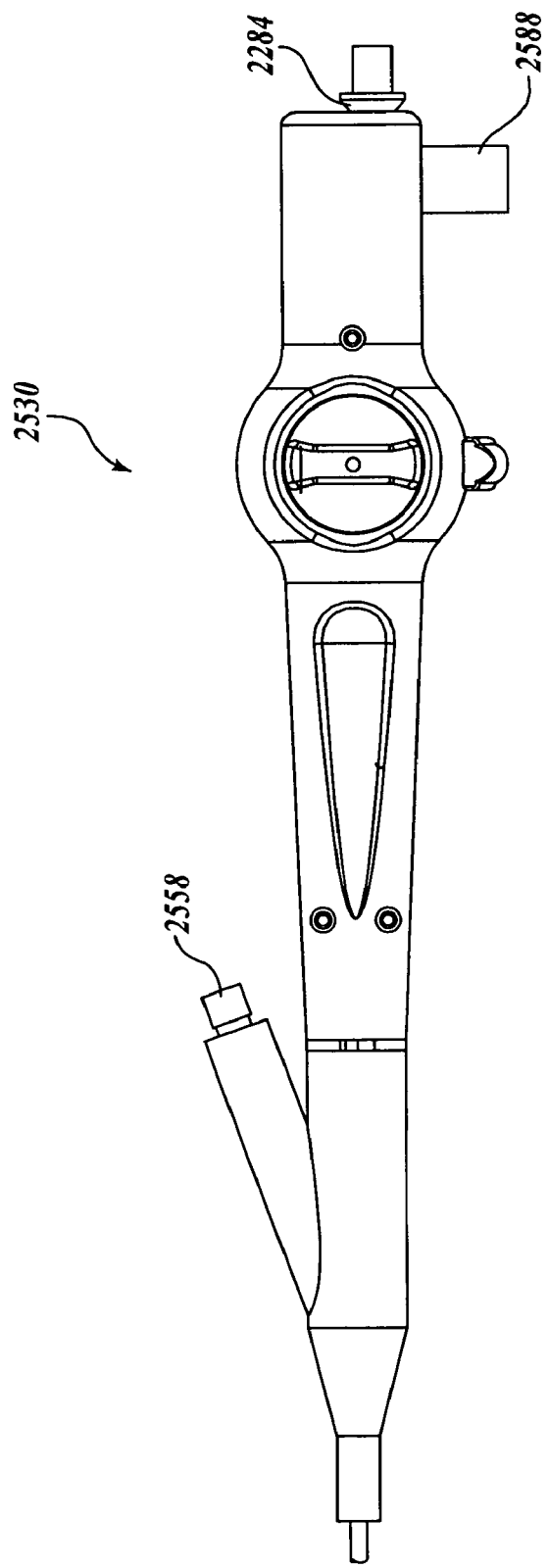
FIG. 25 is a top view of another catheter handle formed in accordance with aspects of the present invention.

FIG. 25 illustrates another embodiment of a catheter handle 2530 constructed in accordance with aspects of the present invention that is suitable for use with the catheter 1910 of FIG. 19A. The catheter handle 2530 is substantially similar in construction, materials, and operation as the catheter handle described above and shown in FIGS. 19A-19D, except for the differences that will now be described. The catheter handle 2530 shown in FIG. 25 includes the coupler 2584 and optical cable (not shown) of the optical assembly 2540, the coupler 2584 being slid, snapped into, molded, or otherwise mounted onto or within the handle 2530. The components of the optical assembly 2540 are substantially similar in construction, materials, and operation as the components of the optical assembly described in FIGS. 20 and 23A, 23B. The light post 2588 may be included with the coupler 2584 and may be located in a recessed fitting at the rear of the handle. The working channel port 2558 is shown to be side mounted and distal to the activation lever 2580. In this embodiment, an ocular (not shown) can be removably attached to the coupler 2584 for direct viewing if a monitor is not available or connected to a monitor if preferred.

Figure 26:
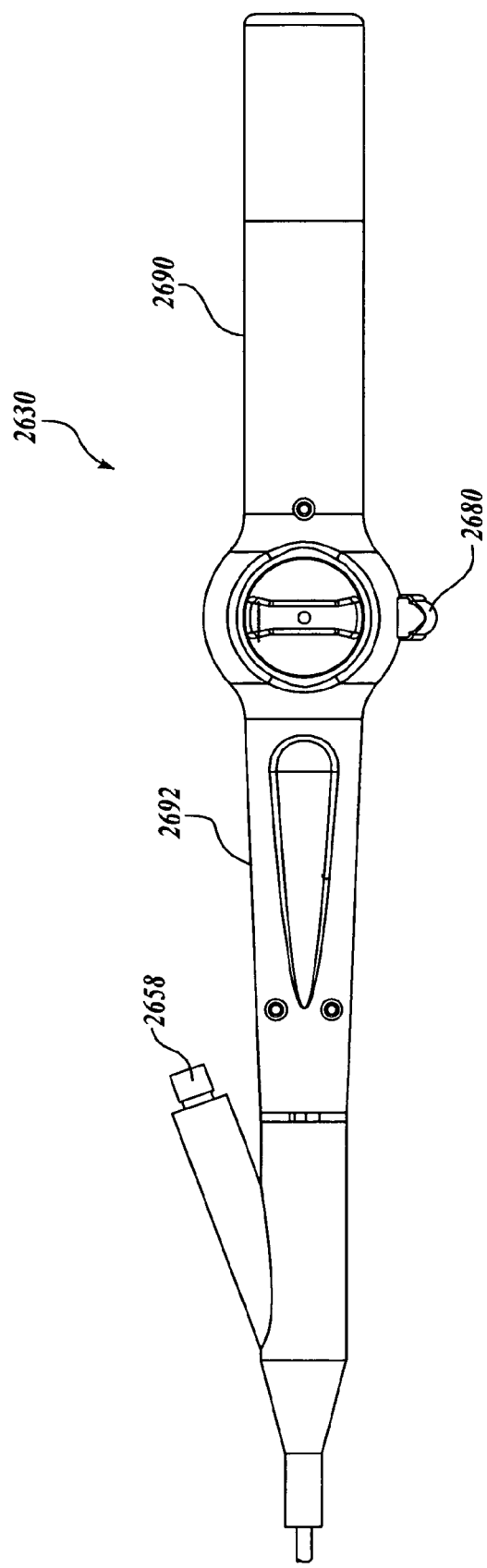
FIG. 26 is a top view of another catheter handle formed in accordance with aspects of the present invention.

FIG. 26 illustrates another embodiment of a catheter handle 2630 constructed in accordance with aspects of the present invention that is suitable for use with the catheter 1910 described above and shown in FIG. 19A. The catheter handle 2630 is substantially similar in construction, materials, and operation as the catheter handle 1930 described above and shown in FIGS. 19A-19D, except for the differences that will now be described. As best shown in FIG. 26, the proximal portion 2690 of the handle 2630 has been lengthened such that the handle can be gripped at either the distal and proximal portions to manipulate the activation lever 2680 with the thumb or other finger of the user. It is desirable that sufficient distance exist between the working channel port 2658 and the handle activation lever 2680, so that the user can comfortable hold the handle without blocking access to the working channel port for device feed. The optic assembly hub 2660 is not shown but can be positioned at the proximal handle end or exiting another side port at the Y-connector. It will be appreciated that the distal portion 2692 can be shortened such that the user uses and holds the proximal end only. Further, it will be appreciated that additional ports and hubs can be added, removed or repositioned as desired.

Figure 27A:
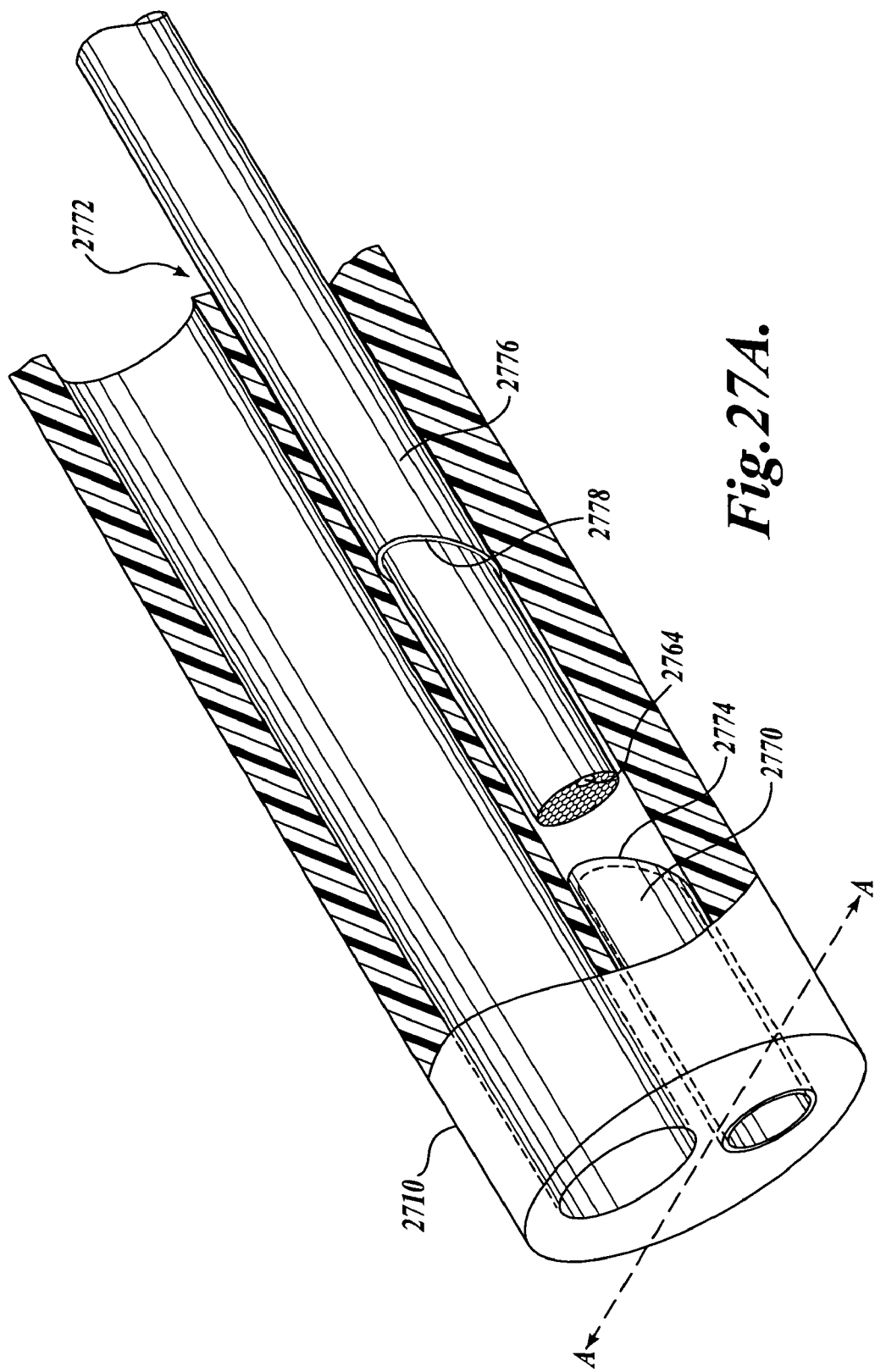

In accordance with another aspect of the present invention, it may be desirable to the user to provide a way to detect the orientation of the optical catheter assembly once in vivo. To that end, FIGS. 27A and 27B illustrate one suitable technique for indicating the orientation of optical catheter assembly when routed to a site within the patient. As best shown in FIG. 27A, an indicator, such as a marker 2764, is placed on the optical cable 2772 of optical assembly 2740 to indicate a relative position, e.g., left side of the optical catheter assembly, when assembled with the catheter to aid the user in orientation and manipulation of the system. For illustration proposes only, the selected marking is shown in FIG. 27A at the distal end of the optic fiber cable 2772 and oriented coplanar with the deflection of the catheter distal end as indicated by arrows A-A. In this embodiment, an insert 2770, such as a metallic insert, is positioned at the distal end of the catheter optical assembly lumen and may be locked into place when the distal end of the catheter is formed. The insert 2770 is formed with the back end angle cut 2774 oriented to the plane of deflection. The cable sleeve 2776 is also configured to have a matching front end angle cut 2778 so that when meshed, the marker 2764 is oriented to indicate the desired position on the image transmitted to the handle. The meshed cuts 2774, 2778 also perform an anti-rotation function, that is, the cable 2772 is not allowed to rotate with respect to the catheter 2710 once meshed, as shown in FIG. 27B. The cable 2772 in this embodiment is made slightly longer than the catheter 2710 such that the cable deflects slightly in the loop hub chamber (see FIG. 19C) when mated to create a constant force against the insert 2770. It will be appreciated that other angles, geometries, keyways, etc. may be used to inhibit rotation of the cable with respect to the catheter and to orient the indicator in the specified location.

In operation, when the distal end of the catheter is deflected, the lumen length of the catheter becomes shorter due to the radius of the deflection curve. The insert 2770 prevents the cable 2772 from extending any further beyond the catheter distal end. The cable length is displaced by means of the fiber deflecting in the loop hub. As the catheter is straightened, the viscoelastic properties of the cable 2772 allows it to relax to the center of the loop hub, while still maintaining its position and contact with the insert 2770 at the distal end.

Figure 28:
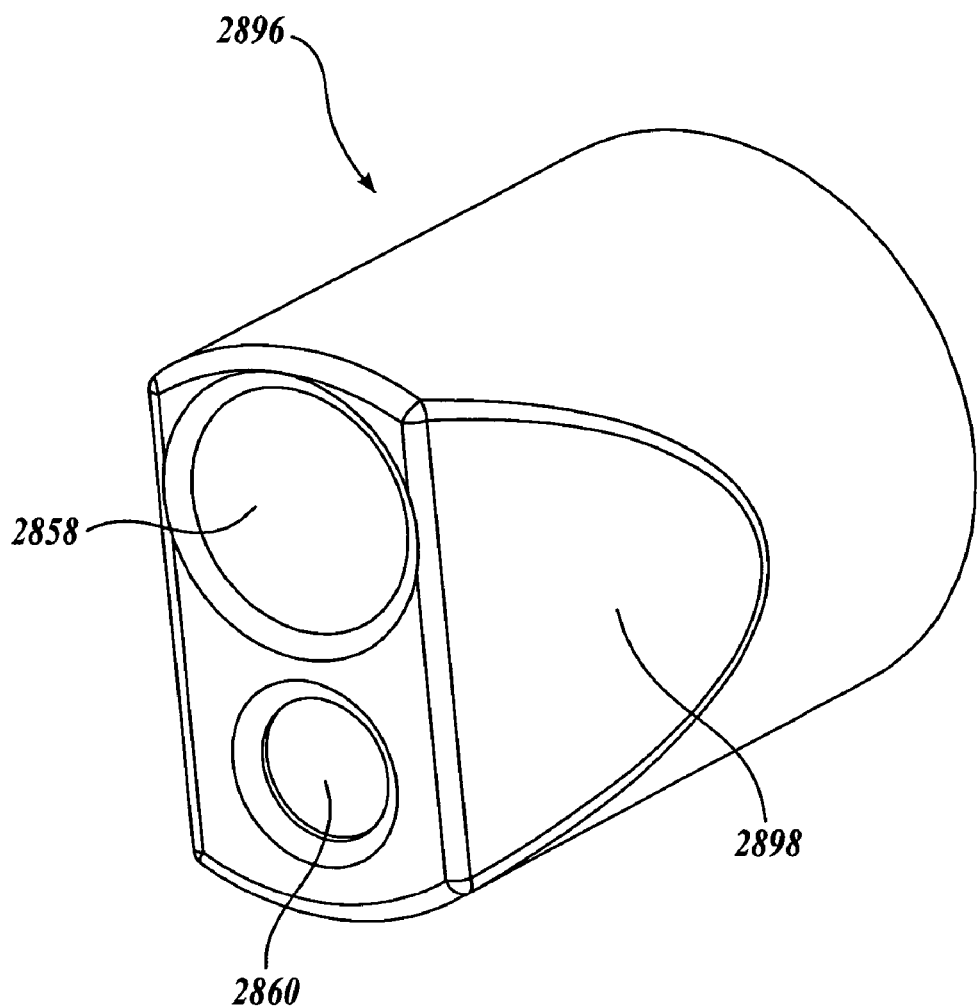
FIG. 28 is a perspective view of one embodiment of a catheter distal end cap formed in accordance with aspects of the present invention.

FIG. 28 illustrates a distal end cap 2896 that may be practiced with one of the catheters described above. A hole 2858 through the cap for the working channel is the same or larger than the working lumen of the catheter body. The distal hole 2560 in the cap for the optic fiber is size slightly smaller than the optical cable, establishing a stop mechanism for preventing the cable from exiting the cap yet providing a ledge for the cable to constantly abut against. The cable in this embodiment is made slightly longer than the catheter. The distal cap 2876 includes tapered sides 2898 to minimize the cross sectional area of the catheter distal end for reducing trauma when advanced in-vivo.

Figure 29:
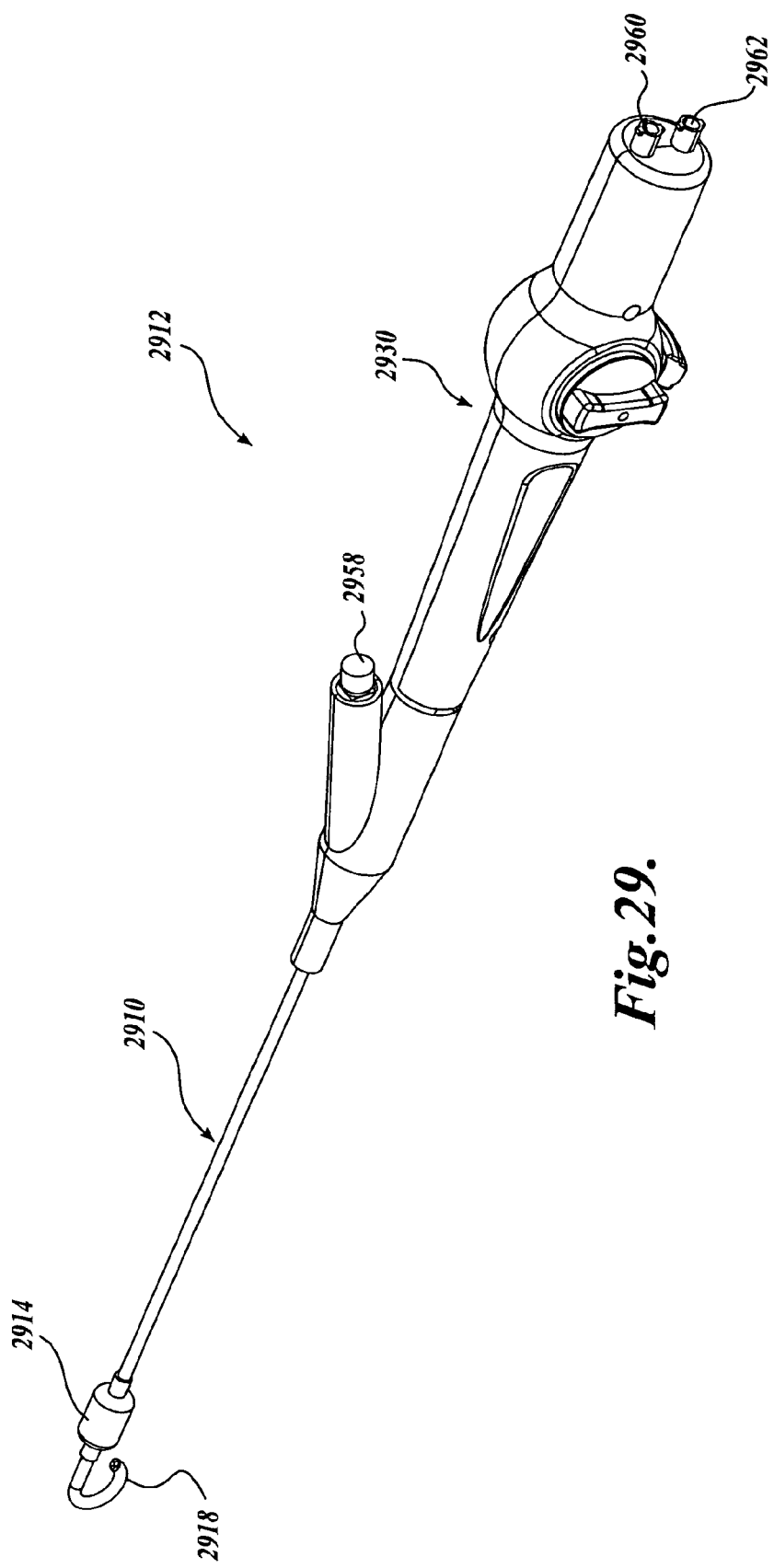
FIG. 29 is a perspective view of another suitable embodiment of a catheter assembly suitable for use in an optical catheter assembly.

FIG. 29 illustrates another embodiment of a catheter assembly 2912 where a balloon 2914 is mounted on the catheter 2910 at or near the distal end 2918 with an accompanying inflation/deflation port 2962 at the proximal end of the handle. It will be appreciated that different types of balloons can be used for occlusion, dilatation, anchoring, or stabilizing yet still allow the working channel to remain patent for other uses. Other embodiments may include side ports for injections or suction. Other features may also be included, including an additional working channel as well as elevators, etc. Complex curve deflection can also be achieved as well as four or multiple way deflections.

Figure 30:
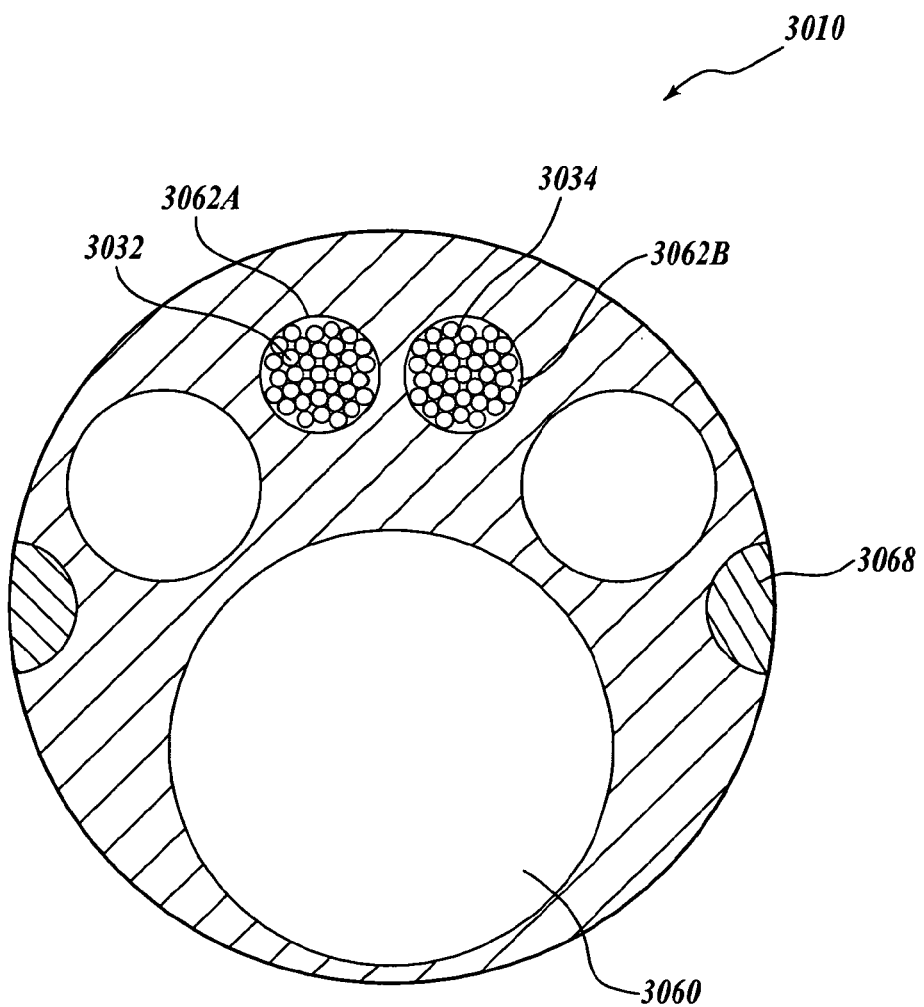
FIG. 30 is a cross-sectional view of another embodiment of a catheter that is suitable for use with the catheter assembly shown in FIG. 19A.

FIG. 30 illustrates a cross section of another embodiment of a catheter 3010. In this embodiment, it may be desired due to economies of manufacture and in the interests of reducing the overall outer diameter of the catheter to split the elements of the optical cable. As best shown in FIG. 30, there is shown a multi-lumen catheter having separate lumens 3062A and 3062B to house the illumination and image fiber bundles 3032 and 3034, respectively. By separating both optic cable components in this way, a reduced catheter outer diameter may be realized.

It will be appreciated that the optical catheter system in the various embodiments described above could be used in other applications, such as a colonoscope, bronchoscope, gastroscope or similar visual device. Additionally, various modifications to the configurations, such as the number and dimension of working/optic channels, the length of the catheter, the materials used in construction, etc., may be made to accommodate the specific application without departing from the spirit of the invention.

Figure 31:
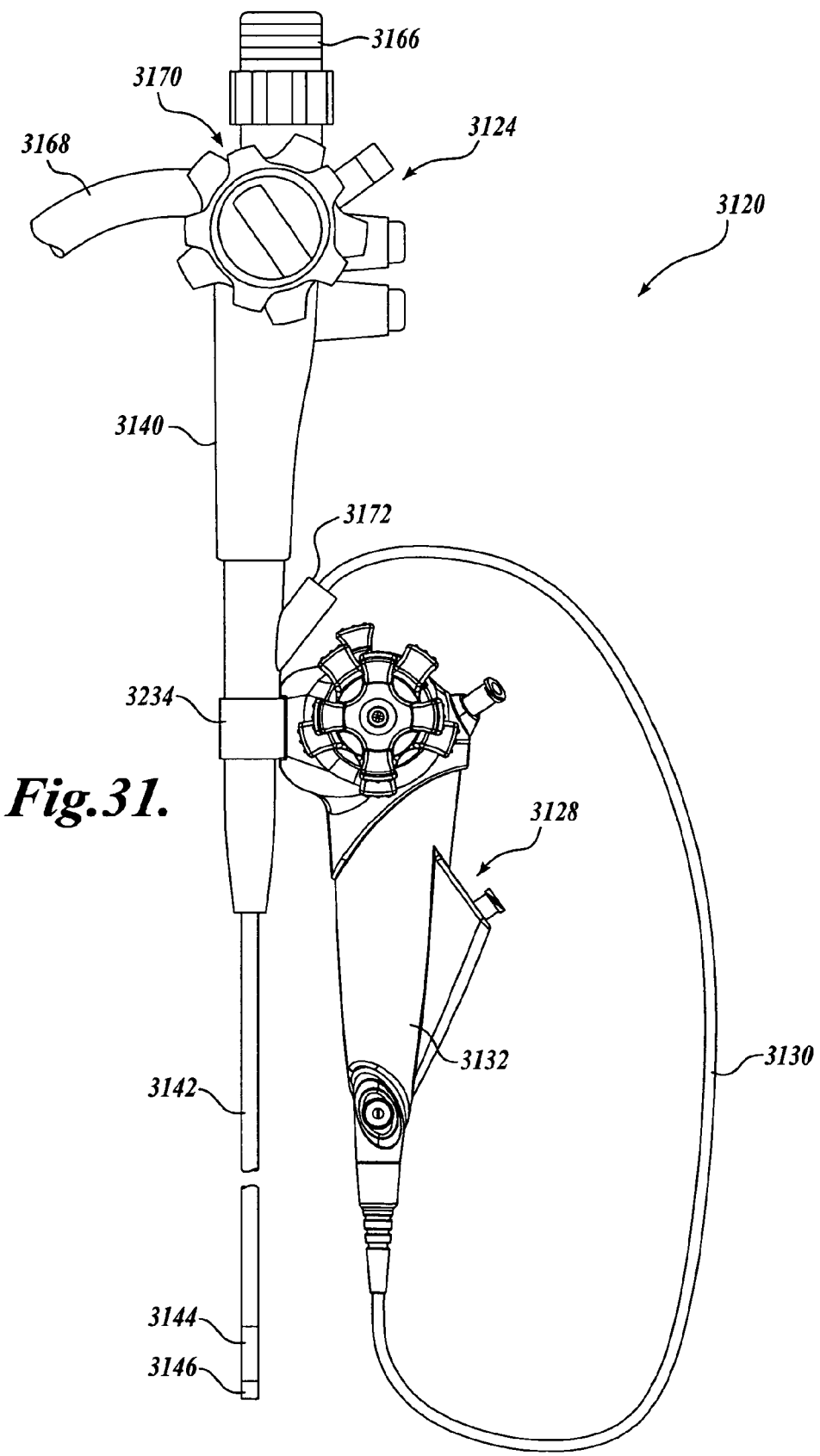
FIG. 31 is a front elevational view of one representative embodiment of an in-vivo visualization system constructed in accordance with aspects of the present invention.

FIG. 31 illustrates one exemplary embodiment of an in-vivo visualization system 3120 constructed in accordance with the present invention. The visualization system 3120 includes an endoscope 3124, such as a duodenoscope, to which a steerable catheter assembly 3128 is operatively connected. As will be described in more detail below, the steerable catheter assembly 3128 includes a catheter 3130 and a catheter handle 3132. The assembly 3128 may further include a viewing device 2040, such as a fiberscope (See FIGS. 20 and 23A-23B), or other small imaging device that is routed through a channel of the catheter 3130 for viewing objects at the distal end thereof. While the illustrative embodiments described below will reference the catheter 3130 and the handle 3132, other suitable catheters, catheter handles, and combinations thereof may be utilized in the visualization system 3120, such as those catheters and catheter/optical handles described above with regard to FIGS. 1-30.

In one suitable use, the endoscope 3124 is first navigated down the esophagus of a patient and advanced through the stomach and into the duodenum to the approximate location of the entrance to the common bile duct (also known as the papilla). After positioning the endoscope 3124 adjacent the common bile duct entrance, the catheter 3130 of the catheter assembly 3128 is advanced past the distal end of the endoscope 3124 and into the common bile duct entrance. Alternatively, the catheter 3130 may be routed prior to endoscope insertion. Once inside the common bile duct, the fiberscope allows a physician to view tissue in the bile duct, pancreatic duct and/or intrahepatics for diagnosis and/or treatment.

As best shown in FIG. 31, one suitable embodiment of an endoscope 3124 includes an endoscope handle 3140 and an insertion tube 3142. The insertion tube 3142 is an elongated flexible body that extends from the distal end of the endoscope handle 3140. In one embodiment, the insertion tube 3142 includes an articulation section 3144 disposed at its distal region, and a distal tip 3146. The insertion tube 3142 is constructed of well known materials, such as polyether block amides (e.g., Pebax®), polyurethane, polytetrafluoroethylene (PTFE), nylon, to name a few.

Figure 32:
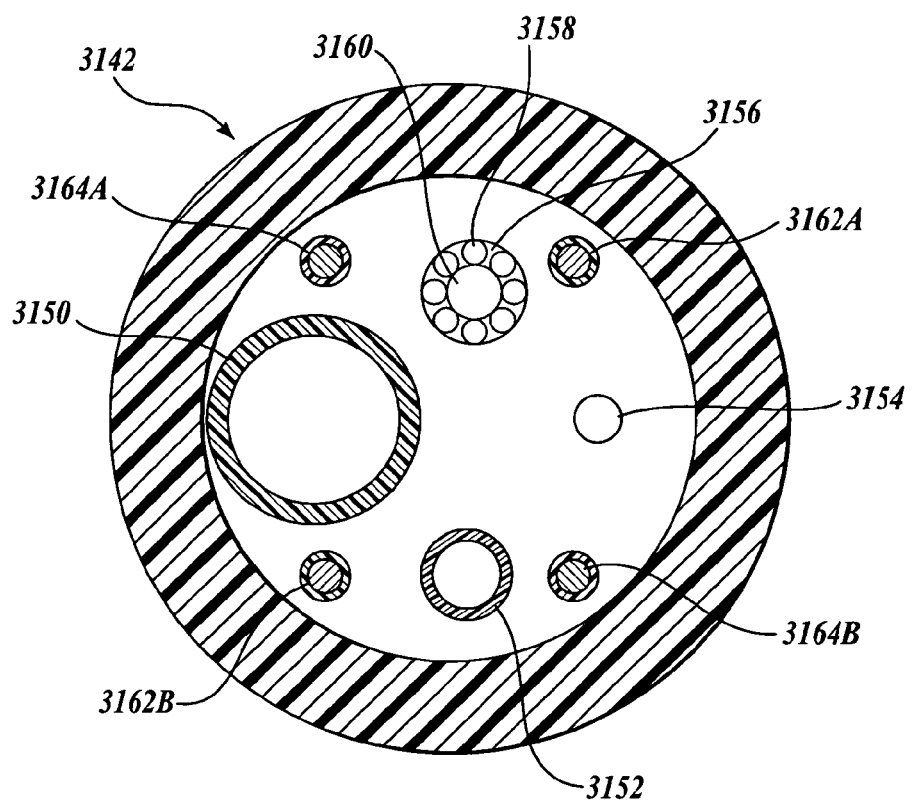
FIG. 32 is a lateral cross sectional view of an insertion tube of an endoscope shown in FIG. 31.

As best shown in the cross sectional view of FIG. 32, the insertion tube 3142 defines a working channel 3150 that extends the entire length thereof and allows for the passage of various treatment or diagnostic devices, such as guide wires, biopsy forceps, and the steerable catheter 3130 (FIG. 31). The insertion tube 3142 also includes one or more lumens for the purpose of facilitating the insertion and extraction of fluids, gases, and/or additional medical devices into and out of the body. For example, the insertion tube 3142 may include an irrigation and/or insufflation lumen 3152 and an optional suction lumen 3154. The insertion tube 3142 further includes one or more lumens for the purpose of providing endoscopic viewing procedures. For example, the insertion tube 3142 includes one or more lumens 3156 that extend the entire length of the catheter and allows for light and optical fiber bundles 3158 and 3160 to be routed to the distal end thereof.

Alternatively, the insertion tube 3142 may include one or more LED's and an image sensor, such as a CCD or CMOS, for capturing images at the distal tip and transmitting them to the endoscope handle 3140. Finally, the insertion tube 3142 includes at least one pair of steering wires 3162A and 3162B, and preferably two pairs of steering wires 3162A, 3162B and 3164A, 3164B that are connected at the insertion tube's distal tip and terminate through the proximal end of the insertion tube 3142. It will be appreciated that the insertion tube 3142 may include other features not shown but well known in the art.

Returning to FIG. 31, the proximal end of the insertion tube 3142 is functionally connected to the distal end of the endoscope handle 3140. At the proximal end of the endoscope handle 3140, there is provided an ocular 3166 through which a user can view the images communicated by the optical fiber bundle 3160 (See FIG. 32), and a light cable 3168 for connecting to an external source of light. While the endoscope shown in FIG. 31 includes an ocular, the endoscope may be of the electronic type, in which the ocular may be omitted and the images obtained from the distal end of the endoscope are transmitted to a video processor via the light cable 3168 or other suitable transmission means, and displayed by a suitable display device, such as a LED monitor. Light from the light source can be transmitted to the distal end of the insertion tube 3142 via the light fiber bundle 3158. The endoscope handle 3140 also includes a steering mechanism 3170, as shown in the form of control knobs, that are connected to the steering wires 3162A, 3162B, and 3164A, 3164B (see FIG. 32) in a conventional manner for deflecting the distal end of the insertion tube 3142 in one or more directions. The endoscope handle 3140 further includes a biopsy port 3172 connected in communication with the working channel of the insertion tube 3142 for providing access to the working channel of the insertion tube 3142 from a position exterior the endoscope handle 3140.

Figure 33:
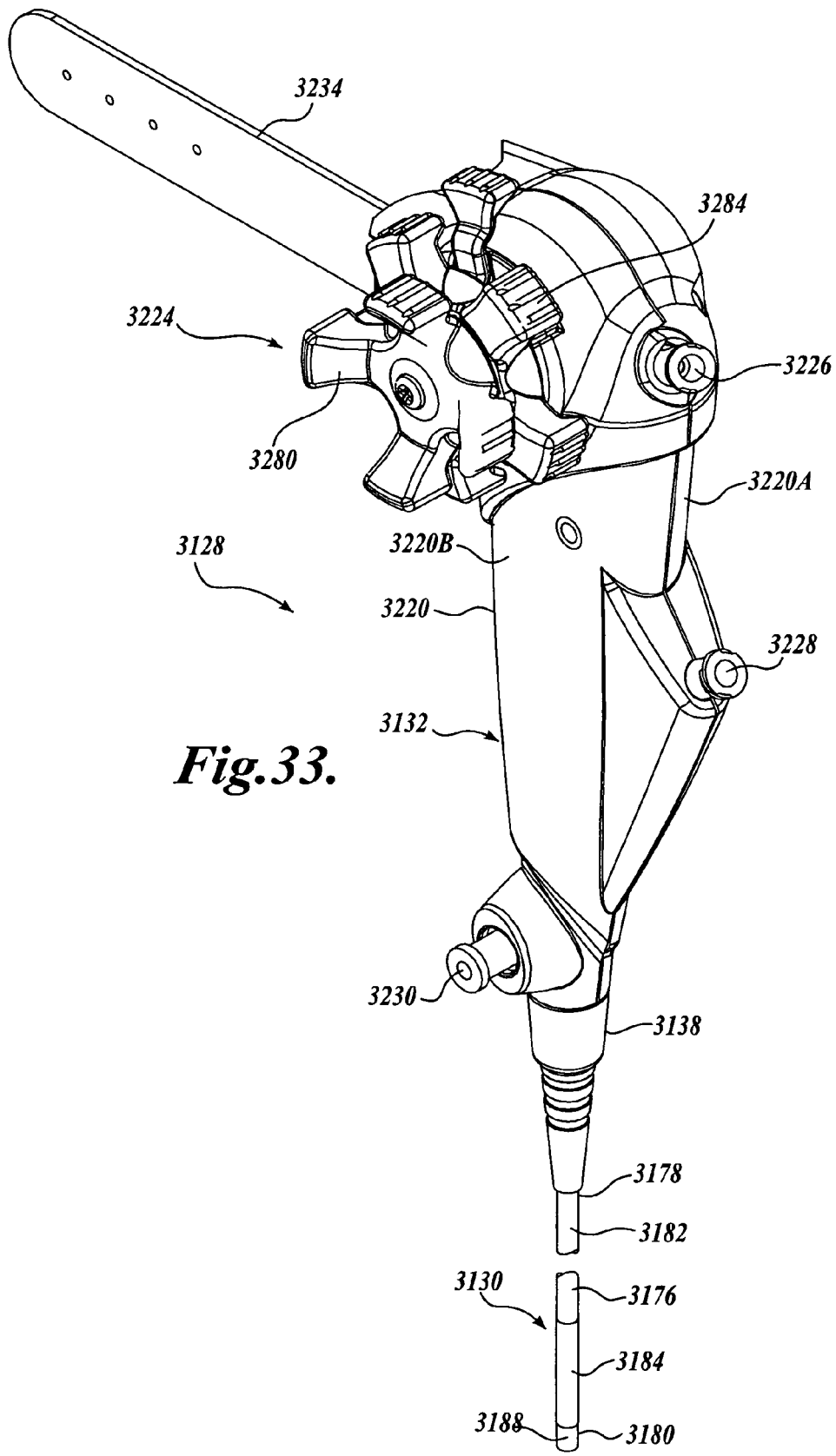
FIG. 33 is a perspective view of one embodiment of a catheter assembly constructed in accordance with aspects of the present invention.
Figure 34:
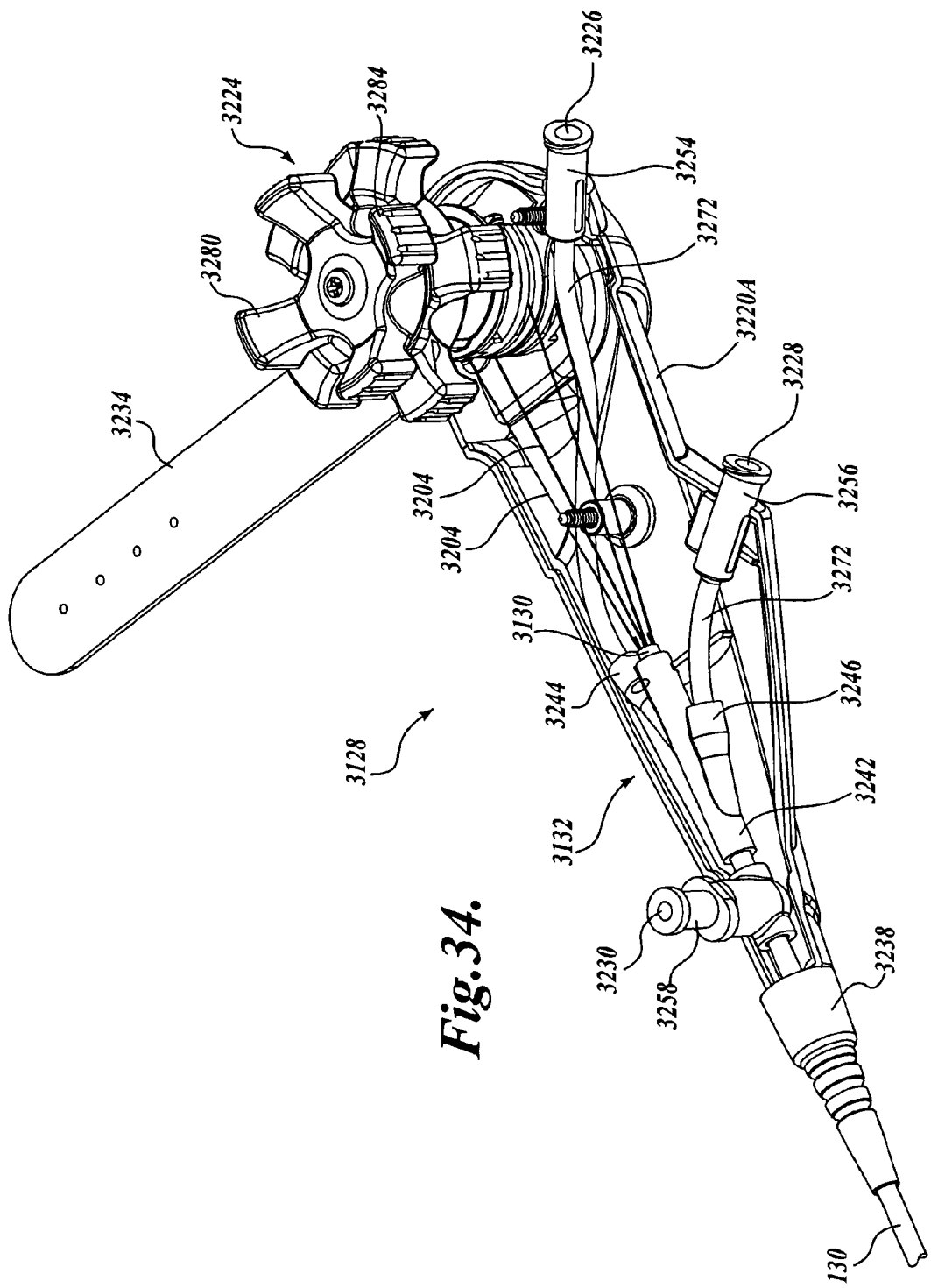
FIG. 34 is a perspective view of the catheter assembly shown in FIG. 33 with one housing half removed.

The in-vivo visualization system 3120 further includes the steerable catheter assembly 3128 which will now be described in more detail. As best shown in FIGS. 33 and 34, one suitable embodiment of the catheter assembly 3128 includes a catheter handle 3132 from which the catheter 3130 extends. The catheter 3130 includes an elongated, preferably cylindrical, catheter body 3176 that extends the entire length of the catheter 3130 from the catheter proximal end 3178 to the catheter distal end 3180. In one embodiment, the catheter body 3176 has an outer diameter between approximately 5 and 12 French, and preferably between approximately 7 and 10 French. The catheter body 3176 may be constructed from any suitable material, such as Pebax® (polyether block amides), nylon, polytetrafluoroethylene (PTFE), polyethylene, polyurethane, fluorinated ethylene propylene (FEP), thermoplastic elastomers and the like, or combinations thereof. The body 3176 may be formed of a single material using known techniques in the art, such as extrusion, or multiple materials by joining multiple extruded sections by heat bonding, adhesive bonding, lamination or other known techniques. According to a preferred embodiment of the present invention, the distal portion of the catheter (approximately 1-2 inches where the flexing occurs) is made more flexible (i.e., less stiff) than the remainder of the catheter.

In the embodiment shown in FIG. 33, the catheter body 3176 includes a proximal section 3182 that extends the majority of the catheter 3130, a deflection section 3184, and a distal tip section 3188. The catheter 3130 preferably varies in stiffness between the proximal section and the distal tip section. More preferably, the proximal section 3182 is stiffer than the deflection section 3184. This allows the catheter to be easily advanced without compressing and with minimal twisting while providing deflection capabilities to the deflection section 3184 for deflecting the distal end 3180. In one embodiment, the proximal section 3182 has a durometer value between 35 and 85 shore D, preferable 60-80 shore D, and the deflection section 3184 has a durometer value between 5 and 55 shore D, preferable 25-40 shore D.

Figure 35A:
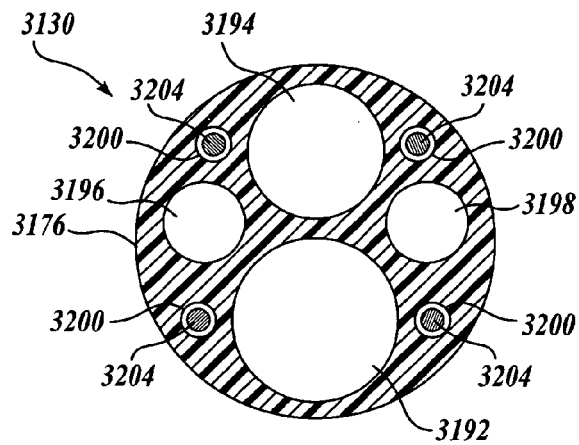
FIGS. 35A-35C are cross sectional views of suitable embodiments of a catheter constructed in accordance with aspects of the present invention.

FIG. 35A is a cross sectional view of one embodiment of the catheter body 3176. The catheter body 3176 defines a working channel 3192 that extends the length of the catheter and allows for the passage of various treatment or diagnostic devices, such as guide wires, stone retrieval baskets, lasers, biopsy forceps etc. In one embodiment, the working channel 3192 preferably has a diameter sufficient to accept up to a 4-French working device, such as biopsy forceps. The catheter body 3176 may also include a channel 3194 that extends the entire length of the catheter through which a fiberscope, fiber optic cable, optical assembly or other small diameter viewing device (e.g., 0.25 mm-1.5 mm diameter) can be routed to the distal end of the catheter 3130. The catheter body 3176 may further include additional channels 3196, 3198 for use, e.g., as irrigation channels or additional working channels. The channels 3196, 3198 each extend the entire length of the catheter and, like the working channel 3192, allow the passage of devices, liquids and/or gases to and from the treatment area. These channels 3196, 3198 each have a diameter similar to or smaller than the main working channel, and may be symmetrically positioned to balance the remaining channels during extrusion. Such positioning of the channels balances out the wall thickness and stiffness in two transverse directions. Finally, the catheter body 3176 may include one or more steering wire lumens 3200 that extend the entire length of the catheter.

Referring to FIGS. 33 and 35A, the catheter 3130 further includes one or more steering wires 3204 that cause the distal end 3180 of the catheter 3130 to deflect in one or more directions. The steering wires 3204 are routed through a corresponding number of steering wire lumens 3200, extend from the distal end 3180 of the catheter 3130 to the opposing, proximal end 3182 of the catheter 3130, and terminate in a suitable manner with the steering mechanism, as will be described in detail below. The steering wires 3204 may be attached to the distal tip section 3188 of the catheter 3130 in a conventional manner, such as adhesive bonding, heat bonding, crimping, laser welding, resistance welding, soldering or other known techniques, at anchor points such that movement of the wires causes the distal end 3180 to deflect in a controllable manner. In one embodiment, the steering wires 3204 are attached via welding or adhesive bonding to a fluoroscopy marker band (not shown) fixedly attached to the distal tip section. In one embodiment, the band may be held in place via adhesive and/or an outer sleeve, as will be described in more detail below. The steering wires 3204 preferably have sufficient tensile strength and modulus of elasticity that they do not deform (elongate) during curved deflection. In one embodiment, the steering wires are made from 304 stainless steel with an 0.008 inch diameter and have a tensile strength of approximately 325 KPSI. The steering wires 3204 can be housed in a PTFE thin-walled extrusion (not shown) to aid in lubricity and prevent the catheter 3130 from binding up during deflections, if desired.

In the illustrated embodiment shown in FIG. 35A, the catheter 3130 includes two pairs of steering wires 3204 that controllably steer the catheter 3130 in two perpendicular planes. In alternative embodiments, the catheter 3130 includes one pair of steering wires 3204 that allow the user to steer the distal tip in one plane. In one embodiment, two steering wires may be provided and are located on opposite sides of the catheter 3130 and slide within grooves, as opposed to steering wire lumens 3200, formed in the elongated body 3176 or either the sheath or outer sleeve, if included, as will be described in more detail below. In a further embodiment, the catheter 3130 only includes one steering wire 3204 that allows the user to steer the distal tip in one direction. In another embodiment, the steering wires may be omitted, and thus, the catheter 3130 can be of a non-steerable type. In such an embodiment, the catheter can be advanced over a guidewire (not shown) pre-placed in the bile or pancreatic duct.

Figure 35B:
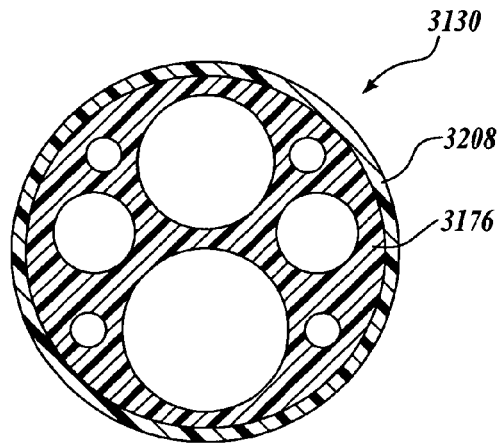

In one embodiment, the catheter 3130 may also include an outer sleeve 3208 that encases the length of the elongated body 3176, as shown in cross section in FIG. 35B, or sections thereof. The outer sleeve 3208 may comprise one of any number of polymer jackets that are laminated, co-extruded, heat shrunk, adhesive bonded, or otherwise attached over the catheter body 3176. Suitable materials for the sleeve 3208 include, but are not limited to, polyethylene, nylon, Pebax® (polyether block amides), polyurethane, polytetrafluoroethylene (PTFE), thermoplastic elastomers to name a few. The outer sleeve 3208 may be used to vary the stiffness of the catheter, if desired, or to provide improved torque transfer and/or other desirable catheter properties. Additionally, the sleeve 3208 may be used as one convenient method for securing a more flexible deflection section to the proximal section, as will be described in detail below. In several embodiments, the external surface of the sleeve 3208 may have a hydrophilic coating or a silicon coating to ease the passage of the device in-vivo, as was described in detail above with reference to FIGS. 2-4.

Figure 35C:
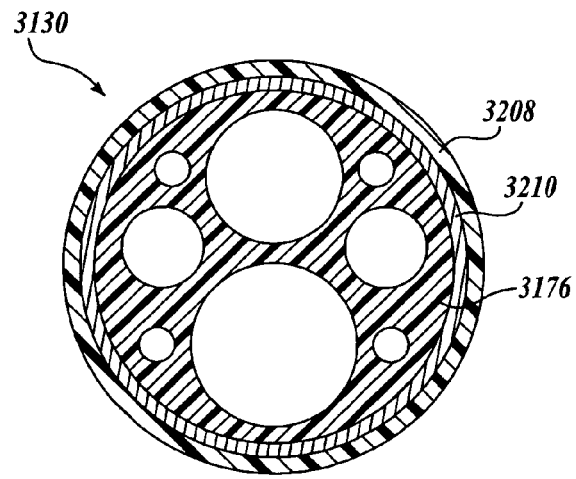

In other embodiments, the catheter 3130 may optionally include an inner reinforcement sheath 3210 disposed between the elongated body 3176 and the outer sleeve 3208. The reinforcement sheath encases the length of the elongated body 3176 or portions thereof, as shown in FIG. 35C. The sheath 3210 may be a woven or layered structure, such as a braided design of fine wire or polymeric elements (0.001 inches to 0.010 inches in diameter) woven or coiled together along the longitudinal axis of the catheter with conventional catheter braiding techniques. This allows the catheter to be advanced to the desired anatomical site by increasing the column strength of the assembly while also increasing the torsional rigidity of the catheter. Conventional coiled polymer or braid wire may also be used for this component with coil wire dimensioning ranging in width from 0.002 to 0.120 inches and thicknesses from 0.002 to 0.10 inches. Braided ribbon wire may also be used for the sheath. In one embodiment, as will be described in more detail below, the outer sleeve 3208 is coextruded, coated, or otherwise attached once the reinforcement layer 3210 is applied, to lock the reinforcement layer in place and secure it to the catheter body 3176, thereby forming a composite catheter.

The catheter may be constructed in many different ways to achieve the desired result of a catheter having varying stiffness along its length. For example, the catheter may be constructed in a substantially similar manner to the catheters described above with reference to FIGS. 12A-18.

Figure 36A:
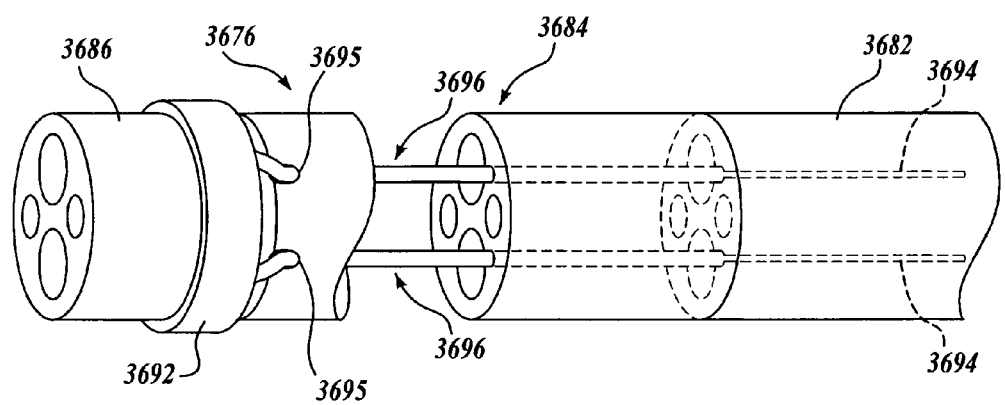
FIG. 36A is a partial view of one suitable embodiment of a catheter body constructed in accordance with aspects of the present invention.

FIGS. 36A-36C, and 37 illustrates one suitable embodiment of a catheter 3630 constructed in accordance with aspects of the present invention that may be used with the visualization system described above. As best shown in FIG. 36A, the catheter includes a catheter body 3676 having a proximal section 3682, a deflecting section 3684, and a distal tip section 3686. In one embodiment, the proximal section 3682 is constructed of a material that is stiffer than the deflecting section 3684. The proximal section 3682 and the deflecting section 3684 may be extrusions constructed from any suitable material, such as polyethylene, nylon, Pebax® (polyether block amides), polyurethane, polytetrafluoroethylene (PTFE), and thermoplastic elastomers, to name a few. In one preferred embodiment, the proximal section is a multi-lumen, PTFE extrusion approximately 200 to 220 cm in length, and the deflecting section 3684 is a multi-lumen, Pebax® extrusion approximately 2 to 10 cm in length. The deflection section 3684 may be coupled to the proximal section 3682 via suitable adhesive or joined by other techniques. The distal tip section 3686 may be coupled to the distal end of the deflection section 3684 via suitable adhesive. The distal tip section 3686 may be constructed of any suitable material, such as stainless steel or engineering plastics, including but not limited to polyethylene, nylon, Pebax® (polyether block amides), polyurethane, polytetrafluoroethylene (PTFE), and thermoplastic elastomers. The catheter body 3676 may also include a radio opaque marker band 3692 that encircles a portion of the distal tip section 3686.

Figure 36B:
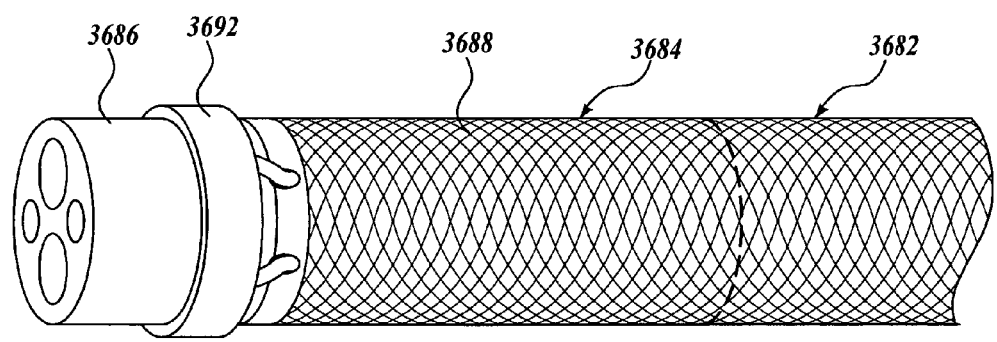
FIG. 36B is a partial view of one suitable embodiment of a catheter formed by taking the catheter body of FIG. 36A and encasing said catheter body with a reinforcement sheath.
Figure 36C:
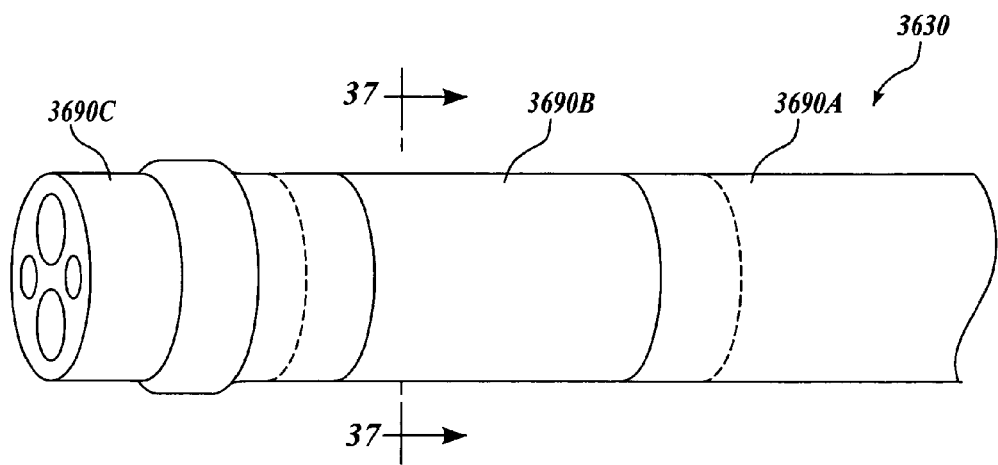
FIG. 36C is a partial view of one suitable embodiment of a catheter formed by taking the catheter of FIG. 36B and encasing said catheter with an outer sleeve.

The catheter 3630 (see FIG. 36B) also includes a reinforcement sheath 3688 that extends from the proximal end of the catheter to or immediately proximal of the radio opaque marker band 3692. The sheath 3688 may be a woven or layered structure, such as a braided design of fine wire or polymeric elements (0.001 inches to 0.010 inches in diameter) woven or coiled together along the longitudinal axis of the catheter with conventional catheter braiding techniques. This allows the catheter to be advanced to the desired anatomical site by increasing the column strength of the assembly while also increasing the torsional rigidity of the catheter. The reinforced catheter body shown in FIG. 36B is then encased by an outer sleeve 3690 comprising of one or more sleeve sections 3690A, 3690B, and 3690C, having the same or different stiffness values, as best shown in FIG. 36C, to form the catheter 3630.

Returning to FIG. 36A, the catheter also includes a plurality of steering wires 3694 that extend through channels of the catheter body from the proximal end of the catheter past the deflecting section 3684. In one embodiment, the steering wires 3694 terminate at the radio opaque marker band 3694 to which the steering wires 3694 are joined by adhesive bonding, laser welding, resistance welding, soldering or other known techniques. In this embodiment, the catheter body includes openings 3695 formed in the outer surface thereof just proximal the radio opaque marker band 3694 via any suitable method, such as skiving. These openings 3695 communicate with the steering wire channels so that the steering wires 3694 may exit the extruded catheter body and connect to the radio opaque marker band 3694, as shown.

Figure 37:
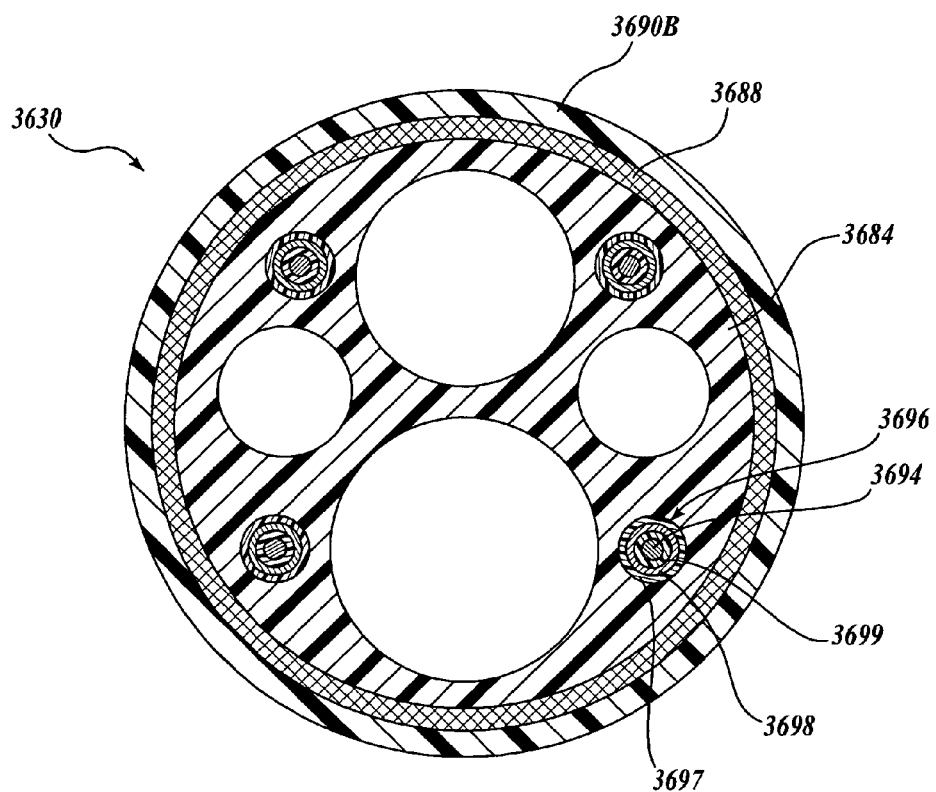
FIG. 37 is a cross sectional view of the catheter taken along lines 39-39 in FIG. 38B.

In some instances where the catheter body is not extruded or otherwise constructed of PTFE or other friction reducing materials, it may be desirable to encase the steering wires 3694 with a laminate structure 3696 for allowing the steering wires 3694 to move freely within the catheter body, and in particular, the deflecting section 3684, and thus, make the mechanics of actuation as smooth as possible. As best shown in FIG. 37, the laminate structure 3696 is formed by outer jacket 3697 constructed of a thermoplastic polymer, such as polyurethane, Pebax®, thermoplastic elastomer etc. which encases an inner reinforcement member 3698, such as a metallic braid (e.g., stainless steel braid having, for example, a 0.0015"×0.006" helically wound). Inside the reinforcement member 3698, is a layer 3699 of a friction reducing material, such as PTFE or FEP tubing, over which the aforementioned layers are formed. In embodiments where the proximal section 3682 is extruded or otherwise formed with a friction reducing material, the laminate structure 3696 begins at the intersection of the proximal section 3682 and the deflecting section 3684 and extends to just proximate the radio opaque marker band 3694, as best shown in FIG. 36A.

In accordance with one embodiment of the present invention, the multi-lumen catheters described herein may be extruded using known materials, such as PTFE, Nylon, Pebax®, to name a few. The catheters may be extruded using mandrels. In several embodiments of the present invention, the mandrels may be constructed from suitable materials, such as stainless steel, stainless steel with PTFE coating, or a phenol plastic, such as Cellcore®. In the embodiment shown in FIG. 35A, the multi-lumen catheter 3130 has eight lumens that include a working channel 3192, a fiberscope or viewing device channel 3194, and four smaller steering wire lumens 3200 spaced 90 degrees apart. To balance out the wall thicknesses and stiffnesses in the traverse directions during extrusion, left and right lumens 3196, 3198 may also be formed using separate mandrels. These lumens 3196, 3198 may be used for air/gas irrigation and insufflation.

The catheter 3130 shown in FIG. 35B may optionally include an outer sleeve 3208. The sleeve may be constructed of suitable materials by coextrusion, heatshrinking processes, such as reflow, or spray coating. The outer sleeve 3208 may provide additional rigidity, improved torque transfer, etc. In one embodiment, the outer sleeve may be applied for facilitating the attachment of a flexible distal section, such as a deflection section, that has a lower durometer value than the remaining catheter body. In such an embodiment, one suitable material that may be used includes, but is not limited to, Pebax® (polyether block amide). In other embodiments, the catheter 3130 may include a reinforcement layer 3210 or sheath between the catheter body 3176 and the outer sleeve 3208, as best shown in FIG. 35C. The reinforcement may be any known catheter reinforcement structure, such as wire coil or braid. In such as embodiment, the outer sleeve 3208 is coextruded, coated, or otherwise attached once the reinforcement layer 3210 is applied, to lock the reinforcement layer in place. It will be appreciated that the reinforcement layer 3210 may extend the entire length of the catheter or portions thereof. In one embodiment, the reinforcement layer 3210 extends over the deflection section. It will be appreciated that if the body is extruded from PTFE, its outer surface should be etched or otherwise prepared for appropriate bonding with the outer layer.

Figure 38A:
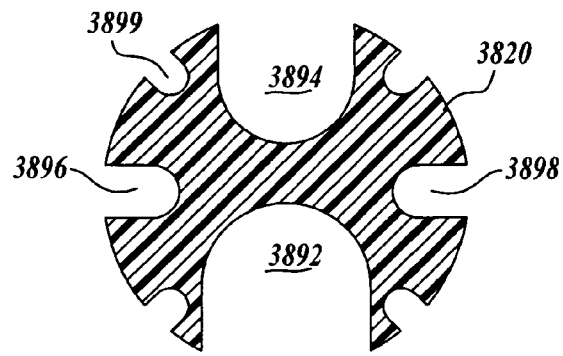
FIGS. 38A-38C are cross sectional views of suitable embodiments of a catheter constructed in accordance with aspects of the present invention.
Figure 38B:
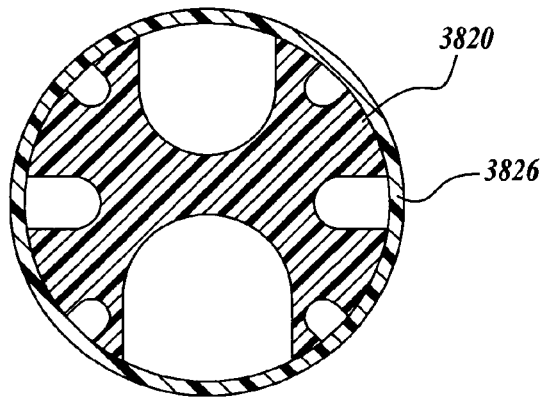
Figure 38C:
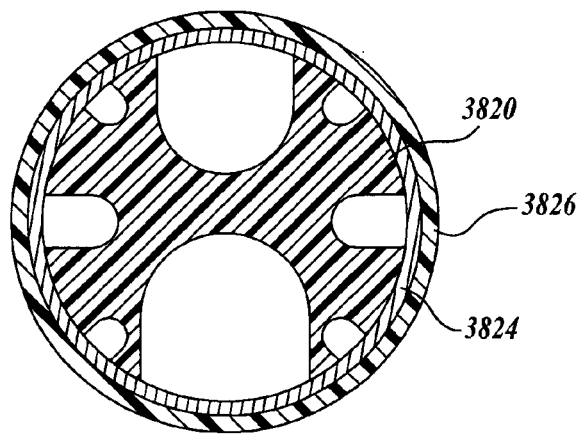

In accordance with another embodiment, the catheter may be built up using a catheter core 3820, an optional reinforcement layer 3824, and an outer sheath or jacket 3826, as best shown in FIGS. 38A-38C. The catheter core 3820 is an open-lumen core that is extruded from suitable materials, such as nylon, PTFE, Pebax®, etc., with the use of mandrels. In this embodiment, the mandrels (not shown) are placed and configured to produced a plurality of open-lumens 3892, 3894, 3896, 3898, and 3899 when extruded. The mandrels may be constructed from metal, Cellcore®, or PTFE. Once the open-lumen core has been extruded, the mandrels are kept in place and the core is either coextruded to add the outer sleeve 3826, as shown in FIG. 38B, or braided and coextruded to add a reinforcement layer 3824 and an outer sleeve 3826, as shown best in FIG. 38C. As was discussed above, the outer sleeve 3826 may function to lock the braid in place and/or to facilitate attachment of a distal section, such as a deflection section, having, for example, a lower stiffness value, if desired.

The mandrels (not shown) can then be removed after coextrusion. In one embodiment, the mandrels are constructed of a phenol plastic, such as Cellcore®. To remove these mandrels, the mandrels are pulled from one or both ends. Due to the "necking down" effect inherent to the Cellcore® material, the cross sectional areas of the mandrels decrease when pulled in tension, thereby allowing the mandrels to be removed from the built-up catheter. In one embodiment, this property of Cellcore® may be used to the manufacture's advantage by using such a material for the steering wire lumen mandrels. However, instead of completely removing the mandrels from the steering wire lumens, tension forces may be applied to the steering wire mandrels, and the mandrels may be drawn to a decreased diameter that will be sufficient to function as the steering wires. Thus, to be used as steering wires, the drawn mandrels are then connected to the distal end of the catheter in a conventional manner. While the latter embodiment was described as being coextruded to form the outer sheath, the outer sheath may be formed on the catheter core by a heat shrink process or spraycoating.

Figure 39A:
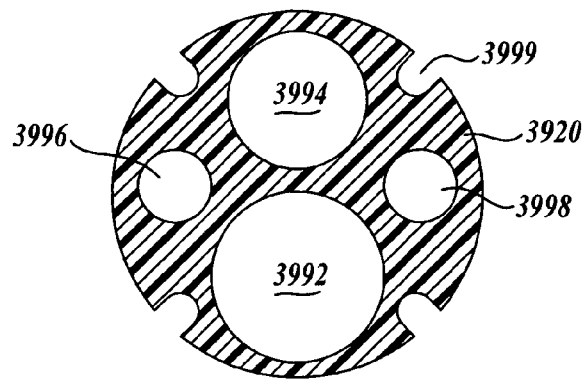
FIGS. 39A-39C are cross sectional views of suitable embodiments of a catheter constructed in accordance with aspects of the present invention.
Figure 39B:
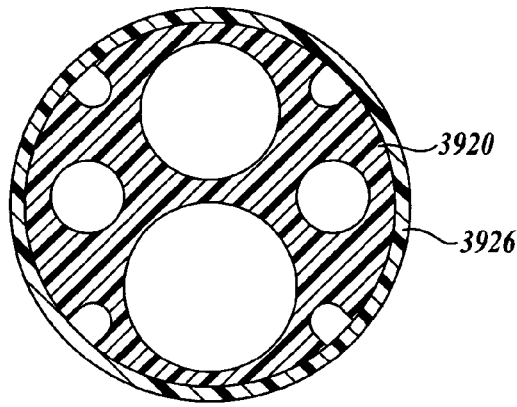
Figure 39C:
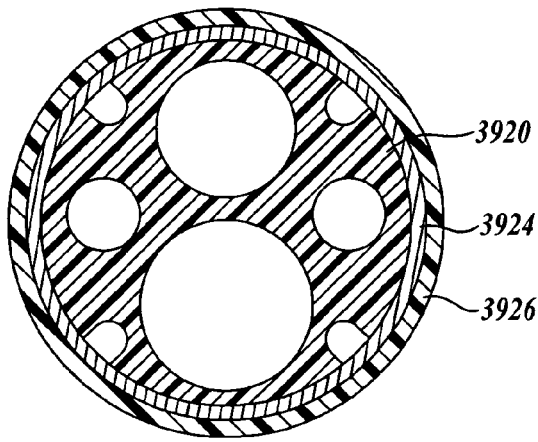

It will be appreciated that not all of the lumens in the latter embodiments need to be formed as open-lumens. Thus, as best shown in FIG. 39A-39C, only the steering wire lumens 3999 are formed as open-lumens. This will create over sized lumens for the steering wires and provided the largest possible lumen diameters for the lumens 3992, 3994, 3996, and 3998.

As was described above, in several embodiments of the catheter, it is desirable for the deflection section to be configured to deflect more easily than the proximal section. In one embodiment, the deflection section has a durometer value less than the proximal section. In other embodiments, the flexibility may be varied gradually (e.g., increasingly) throughout the length of a catheter tube from its proximal end to its distal end. In other embodiments, the deflection section may be an articulating joint. For example, the deflection section may include a plurality of segments that allow the distal section to deflect in one or more directions. For examples of articulation joints that may be practiced with the present invention, please see co-pending U.S. patent application Ser. Nos. 10/406,149, 10/811,781, and 10/956,007, the disclosures of which are hereby incorporated by reference. Other methods that my be used were described above with reference to FIGS. 16-18.

Figure 45:
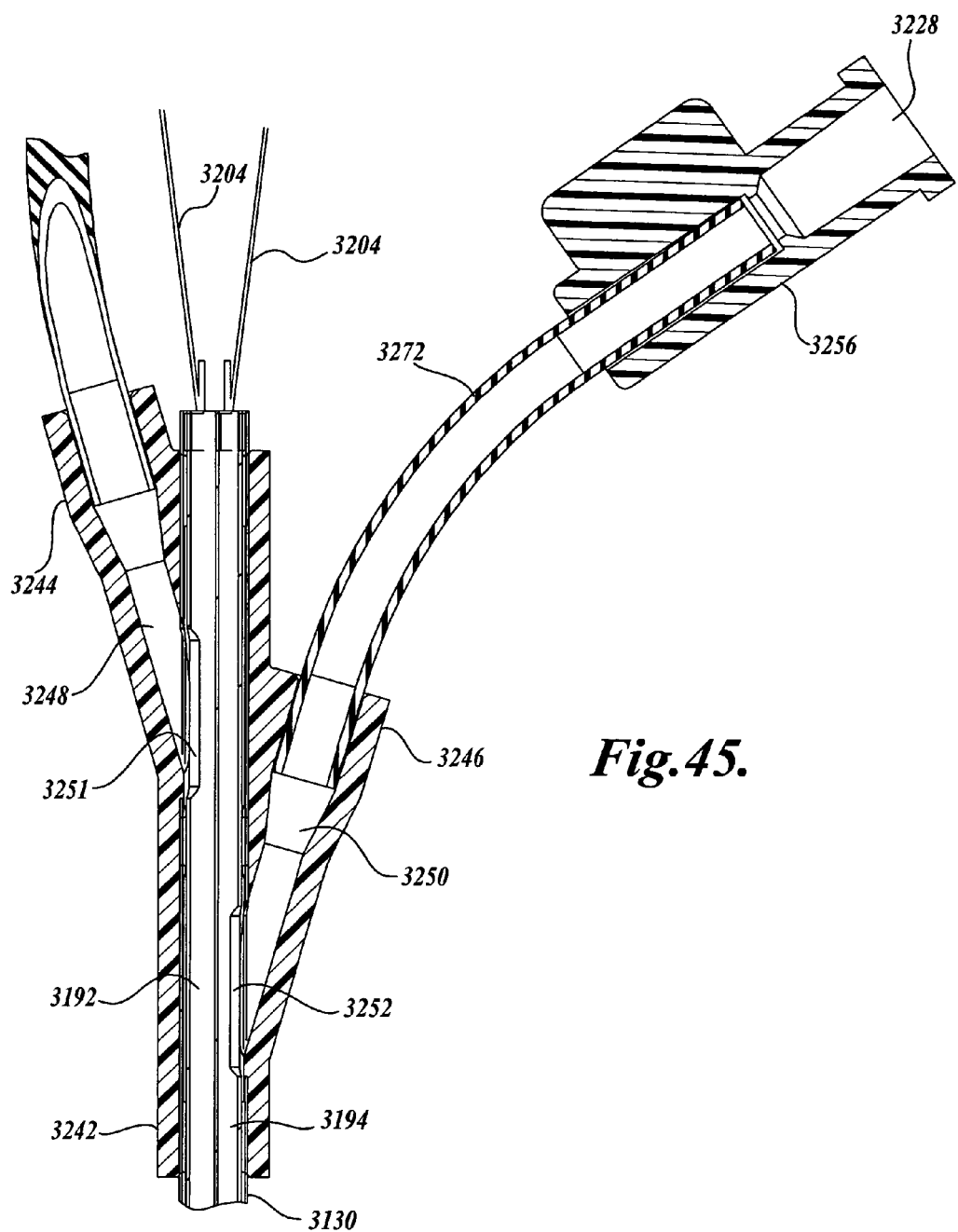
FIG. 45 is a cross sectional view of one embodiment of a Y connector formed in accordance with the present invention when assembled with a catheter.

Returning to FIGS. 33 and 34, the catheter 3130 is functionally connected to the catheter handle 3132. The handle 3132 includes a handle housing 3220 to which a steering mechanism 3224, one or more ports 3226, 3228, 3230, and an endoscope attachment device 3234 is operatively connected. In one embodiment, the handle housing 3220 is formed by two housing halves 3220A and 3220B joined by appropriate removable fasteners, such as screws, or non removable fasteners, such as riveting, snaps, heat bonding or adhesive bonding. In the embodiment shown, the proximal end of the catheter 3130 is routed through a strain relief fitting 3238 secured at the distal end of the handle housing 3220 and terminates at a Y connector 3242, as best shown in FIGS. 34 and 45. The Y connector 3242 may be secured to the handle housing 3220 via any suitable means, such as adhesive bonding. Similarly, the proximal end of the catheter 3130 is securely coupled to the Y connector 3242 via suitable means known in the art, such as adhesive bonding. The Y connector 3242 includes first and second branch fittings 3244 and 3246 that define respective passageways 3248 and 3250 for communicating with the catheter working channel and the catheter imaging device channel, respectively, through openings 3251 and 3252 located on the outer surface of the catheter, as best shown in FIG. 45.

In embodiments of the present invention, the openings 3251 and 3252 may be formed by skiving the outer surface of the catheter. This process may be done manually using known mechanical techniques, or may be accomplished by laser micro-machining that removes a localized area of material from the outer surface of the catheter to expose one or more catheter channels. When assembled, the proximal ends of the catheter channels are plugged by adhesive or the proximal end of the catheter is capped to prohibit access to the channels.

Figure 41:
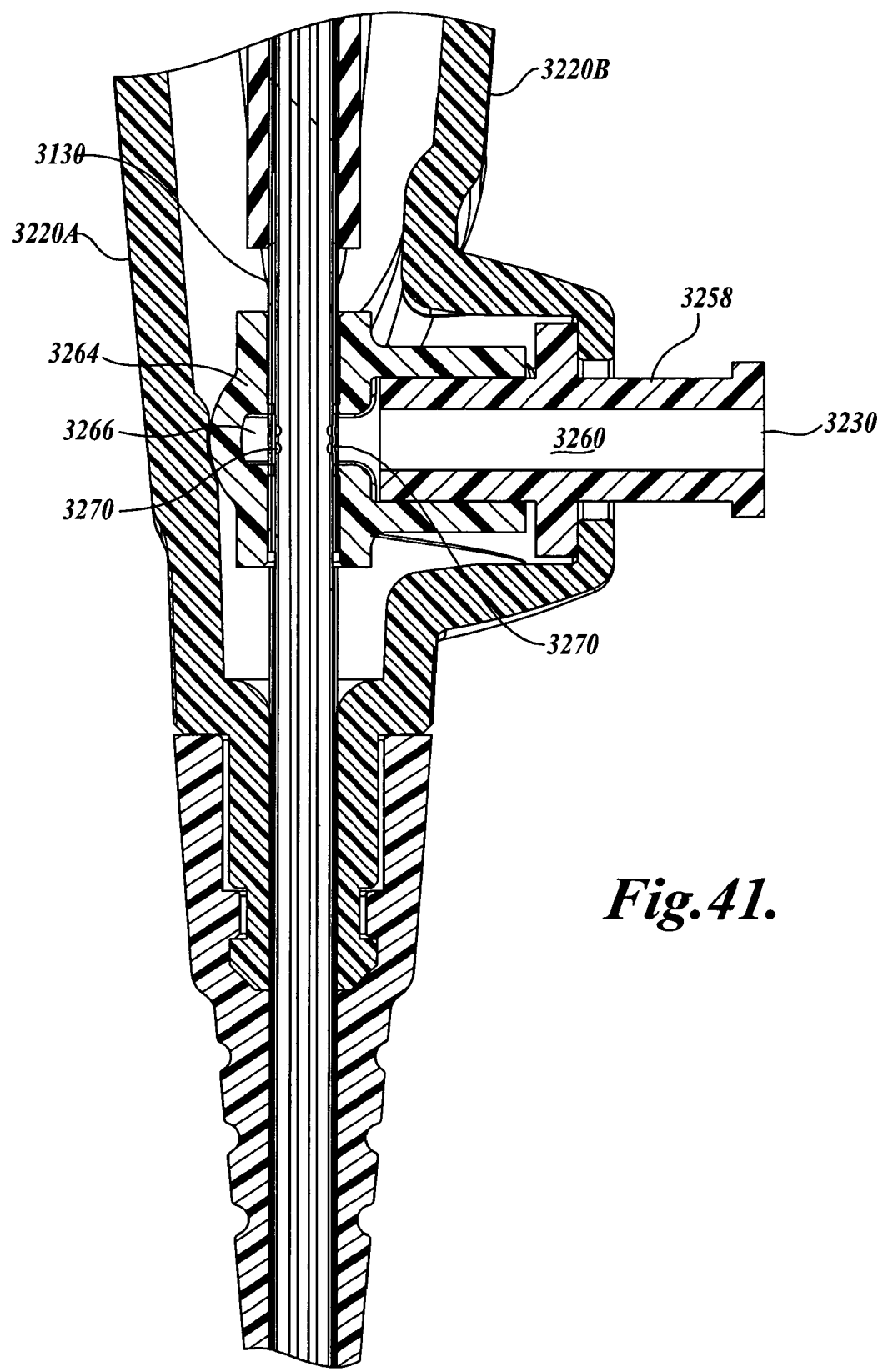
FIG. 41 is a partial cross sectional view of a catheter handle showing a suitable embodiment of an irrigation port connected to irrigation lumens of the catheter.

As was described above, the handle housing 3220 includes one or more ports 3226, 3228, 3230 for providing access the respective channels of the catheter 3130. In the embodiment shown, the ports include, but are not limited to, a working channel port 3226, an imaging device port 3228, and an irrigation/suction port 3230. The ports may be defined by any suitable structure. For example, the working channel port 3226 and the imaging device port 3228 may be defined by fittings 3254 and 3256, respectively, that may be bonded or otherwise secured to the handle housing 3220 when assembled. In one embodiment, the housing halves may define cooperating structure that securely locks the fittings 3254 and 3256 in place when assembled. With regard to the irrigation/suction port 3230, a luer style fitting 3258 is preferably used for defining the port 3230. The fitting 3258 defines a passageway 3260 for fluidly connecting the port 3230 with the appropriate catheter channels, as best shown in FIG. 41. The fitting 3258 works in conjunction with a barrel connector 3264 that ensconces the catheter 3130. The barrel connector 3264 defines a cavity 3266 that surrounds the perimeter of the catheter 3130 and is fluidly connected to the appropriate catheter channels (irrigation channels) via inlets 3270. As such, the port 3230 is connected in fluid communication with the irrigation channel via passageway 3260 and cavity 3266. In one embodiment, the inlets 3270 are formed by skiving the outer surface of the catheter. This process may be done manually using known mechanical techniques, or may be accomplished by laser micro-machining that removes a localized area of material from the outer surface of the catheter to expose one or more catheter channels. The working channel port 3226 and the imaging device port 3228 are connected in communication with the branch fittings 3254 3256 of the Y connector, respectively, via appropriate tubing 3272, and best shown in FIG. 34.

The catheter handle 3132 also includes a steering mechanism 3224. The steering mechanism 3224 of the catheter handle 3132 controls deflection of the distal end 3180 of the catheter 3130. The steering mechanism 3224 may be any known or future developed mechanism that is capable of deflecting the distal end of the catheter by selectively pulling the steering wires. In the embodiment shown in FIGS. 33 and 34, the steering mechanism 3224 includes two rotatable knobs for effecting 4-way steering of the catheter distal end in the up/down direction and in the right/left direction. This mechanism 3224 includes an outer knob 3280 to control up/down steering and an inner knob 3284 to control right/left steering. Alternatively, the inner knob 3284 may function to control right/left steering and an outer knob 3280 may function to control up/down steering. The knobs are connected to the distal end of the catheter 3130 via the steering wires 3204, respectively, that extend through the catheter 3130. While a manually actuated steering mechanism for effecting 4-way steering of the distal is shown, it will be appreciated that a manually actuated steering mechanism that effects 2-way steering may be practiced with and is therefore considered to be within the scope of the present invention.

Figure 42:
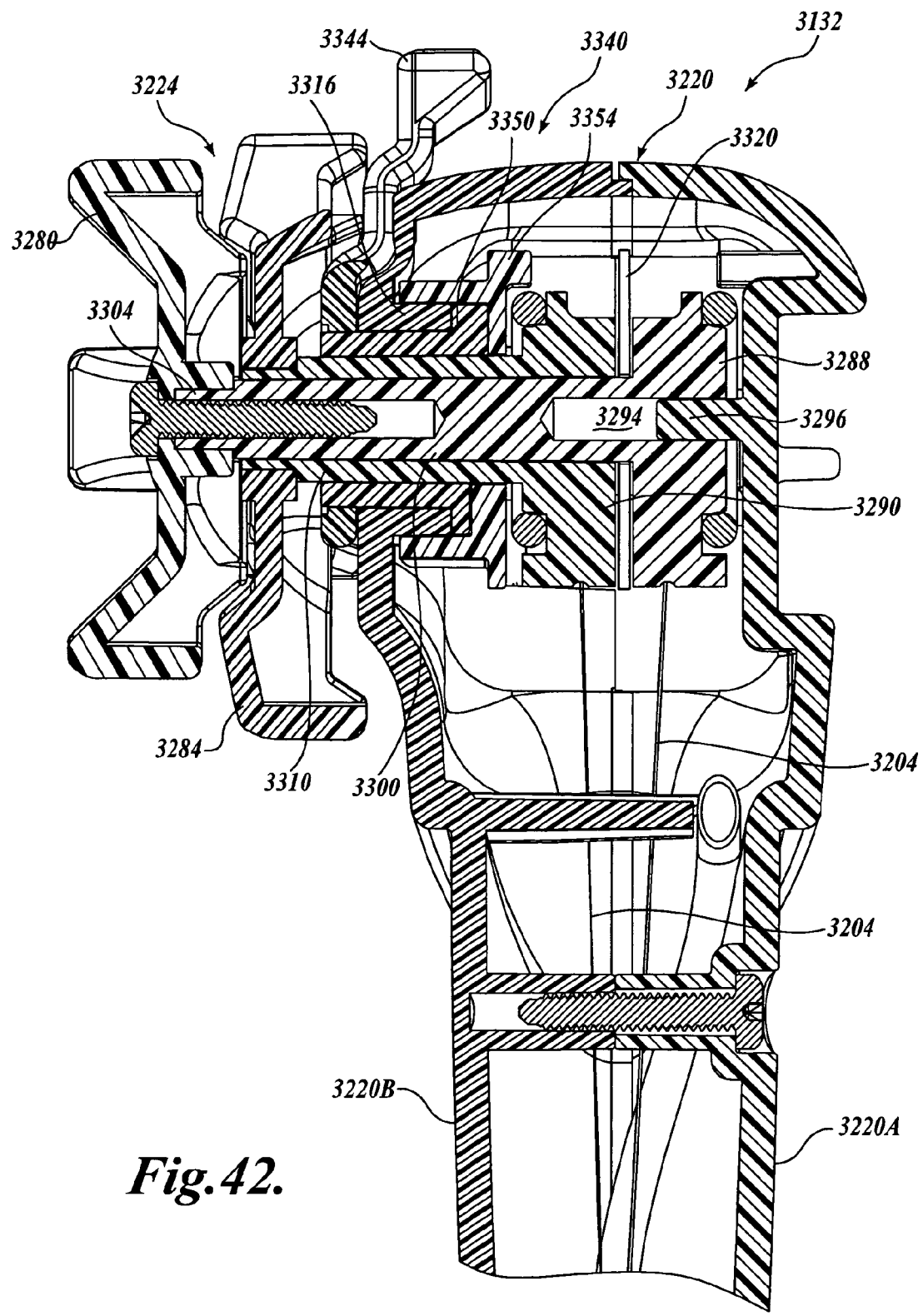
FIG. 42 is a partial cross section view of the catheter handle showing the steering mechanism and the optional locking mechanism.

Referring now to FIG. 42, there is shown one embodiment of the steering mechanism 3224 that may be practiced with the present invention. The steering mechanism 3224 includes inner and outer pulleys 3288 and 3290, and control knobs 3280 and 3284. The inner pulley 3288 for left and right bending control is mounted via an inner bore 3294 for rotation on a shaft 3296 integrally formed or otherwise positioned to extend into the interior of the handle housing 3220 in a fixed manner from the housing half 3220A. The inner pulley 3288 is integrally formed or keyed for rotation with one end of an inner rotary shaft 3300. The opposite end of the inner rotary shaft 3300 extends outside the handle housing 3220 to which the control knob 3280 is attached for co-rotation. In one embodiment, the end 3304 of the inner rotary shaft 3300 is configured to be keyed with a cooperatingly configured control knob opening. The control knob 3280 may then be retained thereon via a threaded fastener. The proximal end of one pair of steering wires 3204 are connected to opposite sides of the inner pulley 3288 in a conventional manner.

The outer pulley 3290 for up and down bending control is rotatably fitted over the inner rotary shaft 3300 for independent rotation with respect to the inner pulley 3288. The outer pulley 3290 is integrally formed or keyed for rotation with one end of an outer rotary shaft 3310. The outer rotary shaft 3310 is concentrically arranged in a rotational manner over the inner rotary shaft 3300. The opposite end of the outer rotary shaft 3310 extends outside the handle housing 3220 to which the control knob 3284 is attached for co-rotation. The rotary shafts 3300, 3310 are further supported for rotation within the housing 3220 by a boss 3316 integrally formed or otherwise positioned to extend inwardly into the handle housing 3220 from the housing half 3220B. It will be appreciated that other structure may be provided that rotatably supports the pulleys 3288, 3290 and shafts 3300, 3310 within the handle housing 3220. When assembled, the proximal ends of the second pair of steering wires 3204 are fixedly connected in a conventional manner to the outer pulley 3290, respectively.

In one embodiment, a thrust plate 3320 is positioned between the inner and outer pulleys 3288, 3290 for isolating rotary motion therebetween. The thrust plate 3320 is restricted from rotation when assembled within the housing 3220.

Figure 40:
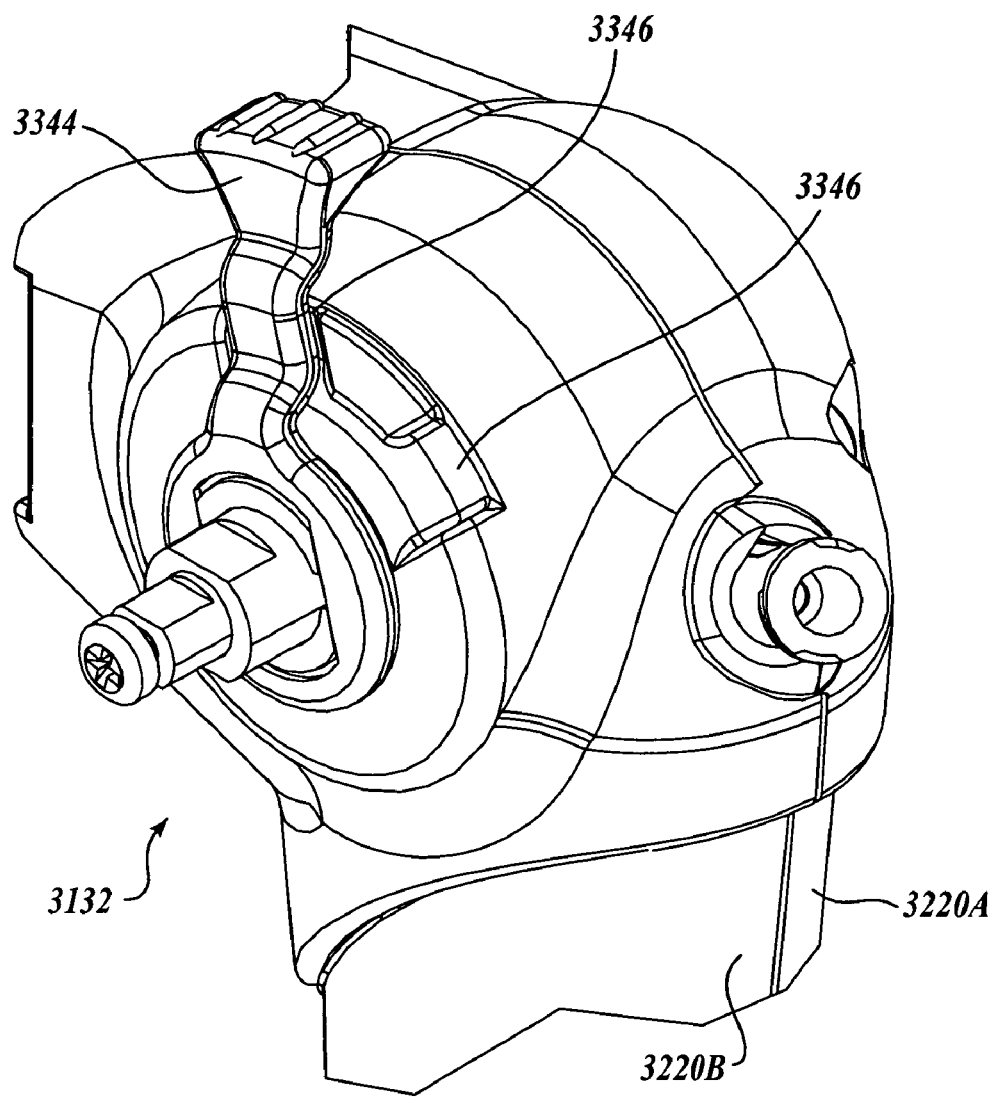
FIG. 40 is a partial perspective view of a catheter handle with the control knobs removed to illustrate a lock lever.

The steering mechanism 3224 may further includes a lock mechanism 3340 that functions to lock the catheter 3130 in a desired deflection position during use. The lock mechanism 3340 includes a lever 3344 that is actuatable between a locked position and an unlocked position. In the embodiment shown in FIG. 40, detents 3346 are provided, and may be molded into the exterior housing half 3220B to index the movement between the locked and unlocked positions. A small protuberance (not shown) may be included to signal the user that the lever 3344 has changed positions.

Figure 43A:
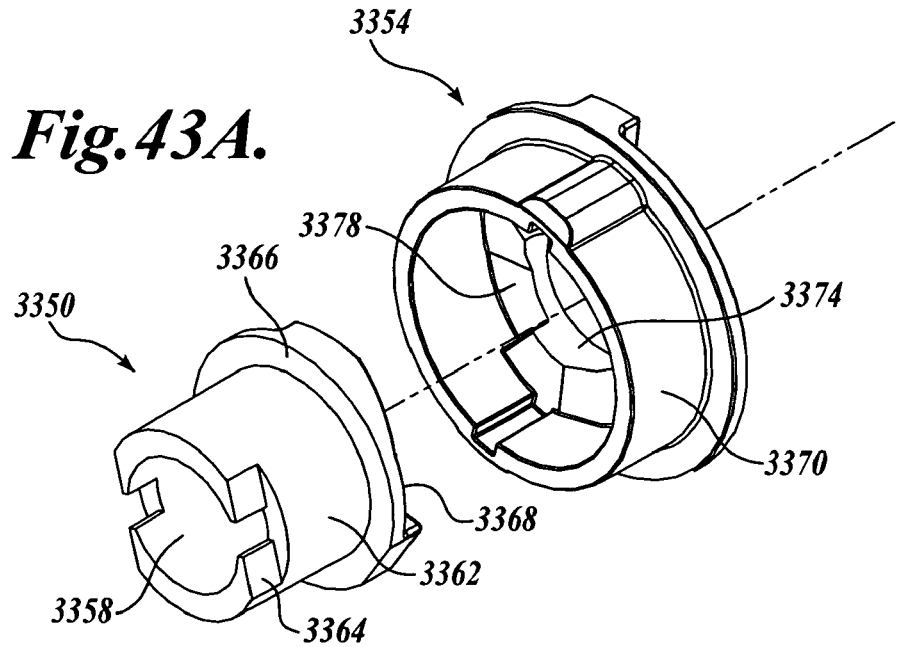
FIG. 43A is a front exploded perspective view of components of the locking mechanism of FIG. 42.
Figure 43B:
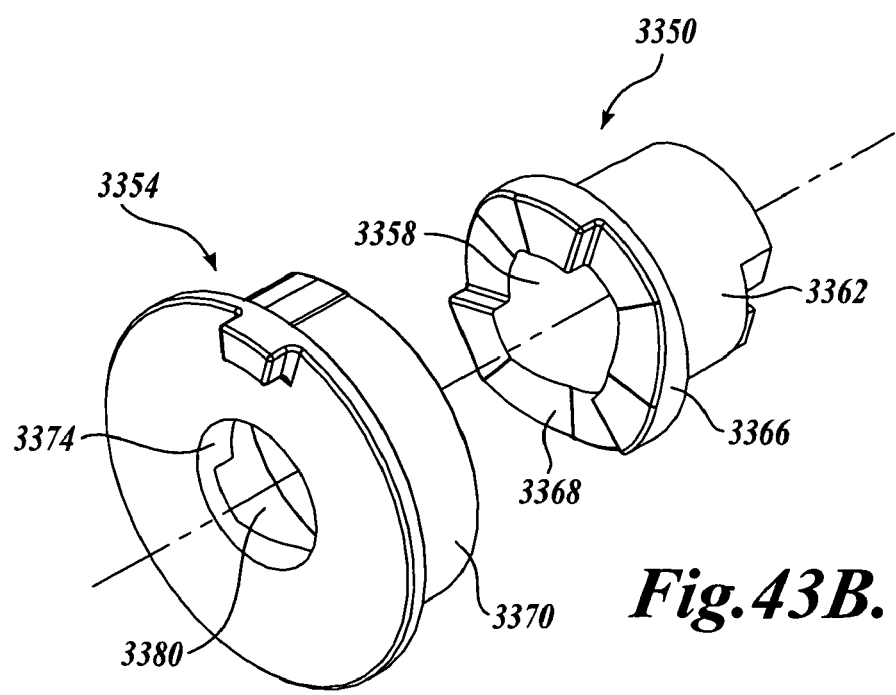
FIG. 43B is a rear exploded perspective view of components of the locking mechanism of FIG. 42.

Referring now to FIGS. 42, 43A, and 43B, the lock mechanism 3340 further includes a lever member 3350 and a pulley member 3354 that are housed within the handle housing 3220 when assembled. The lever member 3350 includes a through-bore 3358 that is size and configured for receiving the outer rotary shaft 3310 in a rotationally supporting manner. The lever member 3350 includes a boss section 3362 that is sized and configured to be rotationally supported by the inwardly extending boss 3316 when assembled. The boss section 3362 is configured at one end 3364 to be keyed for rotation with one end of the lock lever 3344. The lever member 3350 further includes a flange 3366 integrally formed at the other side of the boss section 3362. The end face 3368 of the flange 3366 defines a cam profile that annularly extends around the perimeter of the flange 3366. In the embodiment shown, the cam profile is formed by varying the thickness of the flange. The pulley member 3354 includes a boss section 3370 that is sized and configured for receiving the lever member 3350 therein. The pulley member 3354 includes an inwardly extending flange 3374 that defines a cam profile on the lever member facing surface 3378 of the flange 3374. Similar to the lever member 3350, the cam profile of the pulley member 3354 is formed by varying the thickness of the flanges as it annularly extends. The inwardly extending flange 3374 further defines a throughbore 3380 that is sized and configured for receiving the outer rotary shaft 3310 in a rotationally supporting manner. When assembled, the pulley member 33254 is restricted from rotating with respect to the housing 3220 but allowed to linearly translate, as will be described in more detail below.

When assembled, the lever member 3350 is inserted within the pulley member 3354, the cam profiles mate, and the lever 3344 is keyed for rotation to the lever member 3350. The cam profiles on the lever member 3350 and the pulley member 3354 are specifically configured to transmit a rotary motion of the lever 3344 into translational movement of the pulley member 3354. Thus, when the lever member 3350 rotates by movement of the lever 3344 from the unlocked position to the locked position, the pulley member 3354 moves away from the lever member 3350 in a linear manner by coaction of the cam profiles. Therefore, the lever member 3350 acts like a cam, and the pulley member 3354 acts like a follower to convert rotary motion of the lever 3344 into linear motion of the pulley member. The linear movement of the pulley member 3354 causes the inner pulley 3288 to frictionally engage the housing 3220 and the thrust plate 3320 while the outer pulley 3290 frictionally engages the thrust plate on one side and the pulley member of the other. The friction present between the engaged surfaces prohibits rotation of the inner and outer pulleys 3288 and 3290, and thus, locks the distal end of the catheter in a deflected position.

To change the deflection of the distal end of the catheter from one position to another, the lock lever 3344 is moved from the locked position to the unlocked position. This, in turn, rotates the lever member 3350 with respect to the pulley member 3354. Due to the configuration of the cam profiles of the lever and pulley members, the pulley member 3354 is capable of moving toward the lever member 3350. This alleviates the friction between the engagement surfaces and allows the inner and outer pulleys 3288 and 3290 to rotates by turning the control knobs 3284 and 3280.

Figure 44:
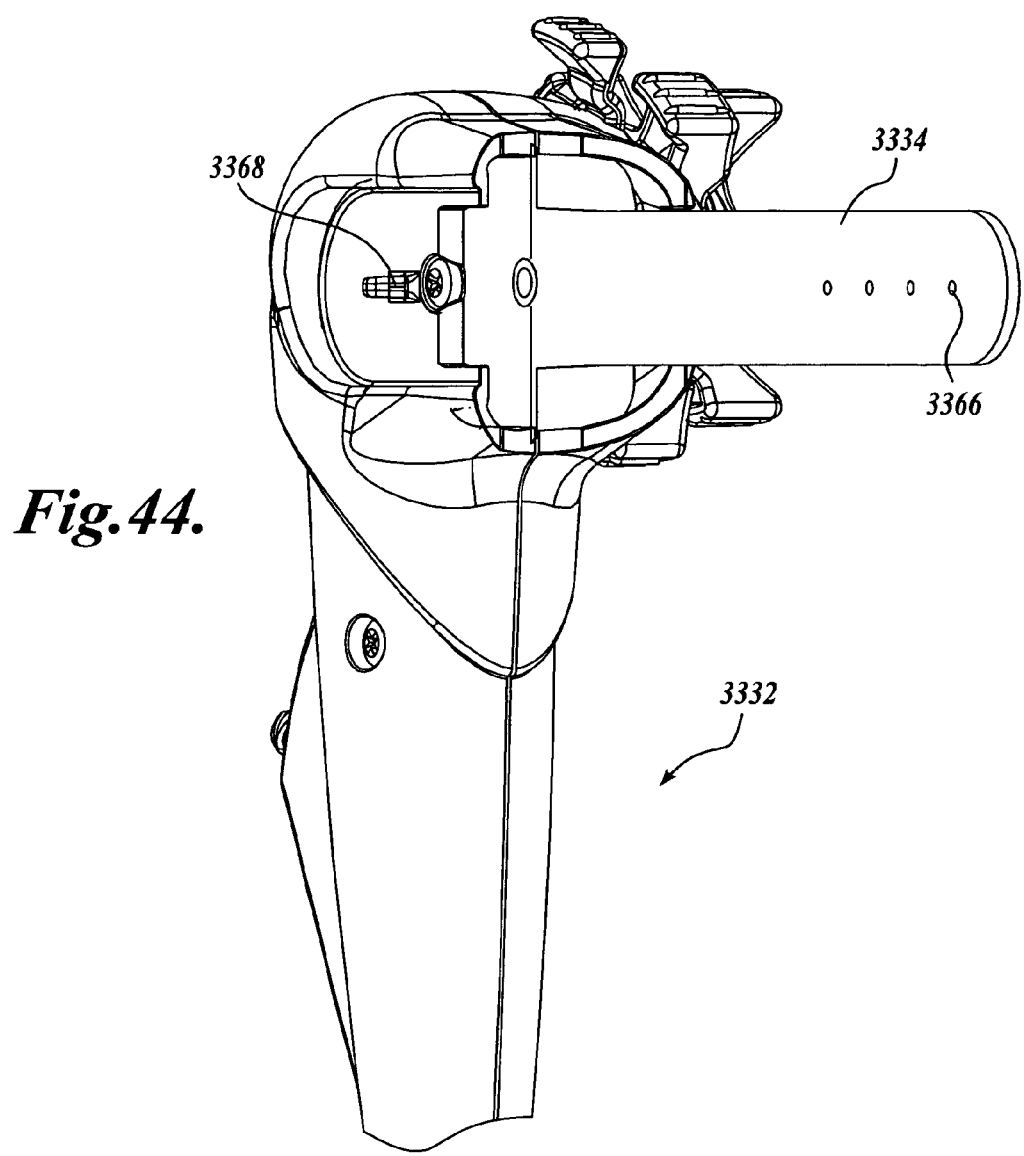
FIG. 44 is a partial perspective view of the catheter handle of FIG. 41 illustrating a suitable embodiment of an endoscope attachment device.

In accordance with aspects of the present invention, the catheter assembly 3128 can be mounted directly to the endoscope handle 3140 so that a single user can manipulate both the endoscope 3124 and the catheter assembly 3128 using two hands. In the embodiment shown, the catheter handle 3132 is attached to the endoscope 3124 via the endoscope attachment device, such as the strap 3234. The strap 3234 can be wrapped around the endoscope handle 3140, as best shown in FIG. 31. The strap 3234 includes a number of notches 3366 into which the head of a housing projection 3368 is selectively inserted to couple the catheter handle to the endoscope, as best shown in FIG. 44. The strap 3234 allows the catheter handle 3132 to rotate around the shaft of the endoscope 3124, if desired. The strap 3234 is positioned such that when used to attach the handle 3132 to the endoscope 3130, the longitudinal axes of the both handles are substantially aligned, as shown best in FIG. 31. Additionally, the strap orientation and the location of the ports on the catheter handle 3132 allow for manipulation of diagnostic or treatment devices and viewing devices through the catheter without interfering with control and use of the endoscope. As a result of directly connecting the catheter assembly 3128 to the endoscope 3124, as shown in FIG. 31, the catheter 3130 creates a loop, known as a service loop, prior to entrance into the biopsy port 3172. In one embodiment, the catheter may include a proximally located stop sleeve or collar (not shown), which limits the minimum diameter of the service loop and the extension of the catheter 3130 beyond the distal end of the conventional endoscope. Alternatively, a mark or indicia may be placed on the catheter 3130 and used to prevent over insertion of the catheter 3130.

In embodiments of the present invention that form a service loop by directly connected the catheter handle 3132 to the endoscope 3124, the catheter 3130 is preferably constructed to be suitably longer than conventional catheters to compensate for the service loop. In several of these embodiments, the catheter handle 3132 is preferable mounted below the biopsy port 3172 of the endoscope 3124 and the catheter 3130 is preferably looped upward and into the biopsy port 3172. In this configuration, the catheter 3130 is accessible and can be gripped by the user just above the biopsy port for catheter insertion, withdrawal, and/or rotation.

While the embodiment above shows a handle connected below the biopsy port and longitudinally oriented with respect to the catheter, other configurations are possible. For example, the handle can be attached to the endoscope so that the longitudinal axis of the catheter handle is substantially transverse to the longitudinal axis of the endoscope handle. Additionally, the catheter handle may be mounted proximally or distally of the biopsy port or may be mounted directly on the biopsy port so that the longitudinal axis of the catheter is coaxial with the biopsy port.

As was discussed briefly above, a small diameter viewing device, such as a fiberscope or other vision device, may be slidably routed through one channel (e.g., imaging device channel) of the catheter 3130 (FIG. 33) to the distal end thereof. The viewing device permits the user of the catheter assembly to view objects at or near the distal end or tip of the catheter. For a detailed description of one viewing device that may be utilized by the visualization system, please see the optical assembly described above with regard to FIGS. 20 and 23A-23B. For other examples of imaging devices that may be practiced with embodiments of the present invention, please see the description of the fiber optic cable in co-pending U.S. application Ser. No. 10/914,411, filed Aug. 9, 2004 to which priority as been claimed, and the guidewire scope described in U.S. Published Patent Application Number 2004/0034311 A1, the disclosures of which are hereby incorporated by reference.

The imaging device 3370 may have a stop collar or sleeve (not shown) to limit movement of the cable 3372 through the imaging device channel of the endoscope and limit the length by which the cable 3372 can extend beyond the distal tip of the catheter 3130. The inner surface of the imaging channel of the catheter may have color markings or other calibration means to indicate to the user when inserting the cable 3372 that the end of the catheter is approaching or has been reached.

One suitable method of operation of the in-vivo visualization system 3120 will now be described in detail with reference to the aforementioned FIGURES. The insertion tube 3142 of the endoscope 3124 is first navigated down the esophagus of a patient under endoscope visualization. The insertion tube 3142 of the endoscope 3124 is advanced through the stomach and into the duodenum at the bottom of the stomach. The biliary tree comprises the cystic duct from the gall bladder, the hepatic duct from the liver and the pancreatic duct from the pancreas. Each of these ducts joins into the common bile duct. The common bile duct intersects with the duodenum a slight distance below the stomach. The papilla controls the size of the opening at the intersection between the bile duct and duodenum.

The papilla must be crossed in order to reach the common bile duct to perform a biliary procedure. The insertion tube 3142 of the endoscope 3124 is navigated under direct visualization so that the exit port of the working channel 3150 is directly across from the papilla or so that the port is slightly below the papilla. After positioning the distal end of the insertion tube 3142 in the proper position, the catheter 3130 with the imaging device 3370 is advanced through the working channel 3150 the endoscope 3124 such that the distal end of the catheter 3130 emerges from the endoscope and cannulates the papilla. The endoscope 3124 provides viewing of the catheter 3130 as it emerges from the endoscope 3124 and is advanced to enter the papilla. After cannulating the papilla, the catheter 3130 may be advanced into the common bile duct. Once advanced into the common bile duct, the fiber optic cable 3372 of the viewing device 3370 located within the catheter 3130 allows a physician to view tissue in the bile duct for diagnosis and/or treatment.

Alternatively, once the insertion tube 3142 of the endoscope 3124 is in place next to the papilla, a conventional guidewire and sphinctertome may be advanced together through the endoscope and through the papilla to enter the common bile duct and pancreatic duct. It may be necessary for the physician to use the sphinctertome to enlarge the papilla. The sphinctertome may then be removed from the patient while leaving the conventional guidewire in place. The catheter 3130 and the fiber optic cable 3372 of the viewing device 3370 may then be advanced together over the conventional guidewire through the papilla and into the common bile duct. Once inside the common bile duct, the fiber optic cable 3372 of the viewing device 3370 allows a physician to view tissue in the bile duct for diagnosis and/or treatment.

It will be appreciated that the selection of materials and use of insertable and removable optics in the catheter allow for the catheter to be constructed as a single use device. Once the procedure is performed, the optics can be removed and sterilized for reuse while the catheter may be removed from the endoscope and discarded.

While the steerable catheter assembly 3128 has been described above for use with an endoscope, it will be appreciated that the catheter assembly may be used with other devices, or may be used as a stand-alone device or in conjunction with the viewing device 3370.

FIGS. 46A-46B illustrates the distal end of an alternative embodiment of a catheter 4630 formed in accordance with aspects of the present invention. In this embodiment, the catheter 4630 has a multi-lumen design with one or more (shown as three) steering wire lumens 4640 around its perimeter. Steering wires (not shown) extend from the proximal end of the catheter to the distal region of the catheter and terminate in an anchored connection at or near the distal end thereof. Deflection of the distal end of the catheter may be effected by the steering wires in a manner well known in the art. The catheter 4630 includes other lumens, for example, a guide wire lumen 4660, a working channel lumen 4662, and a fiberscope or other viewing device lumen 4664. As shown, the guide wire lumen 4660 is offset from the longitudinal axis of the catheter.

In use, the tip of the catheter is advanced beyond the end of the endoscope and is steered in the direction of the papilla. The guide wire is then advanced through the papilla and the catheter is advanced to cannulate the papilla. Once in the biliary tree, and with visualization provided via the fiberscope or other viewing device, the guide wire is advanced again and steered to the target site. The catheter is once more advanced over the guide wire and positioned for use of the accessory instruments at the therapy site while simultaneously viewing such site with the fiberscope.

Figure 47:
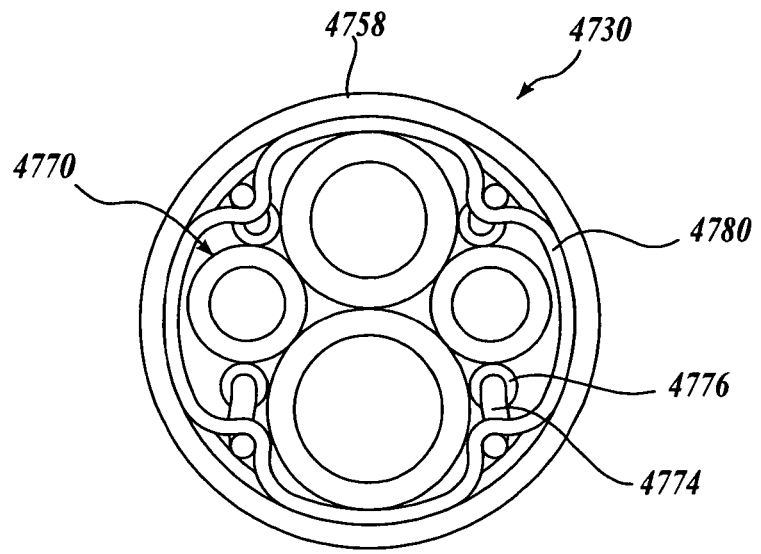
FIG. 47 is an end view of another embodiment of a catheter formed in accordance with the present invention.

In an alternative embodiment, instead of extruding the catheter body, a catheter 4730 may be constructed with an outer sheath 4758 encasing a bundle 4770 of smaller diameter tubes, as best shown in FIG. 47. Each tube of the bundle of tubes may be formed using any known technique, such as extrusion. Each tube extends the length of the catheter and may be used for a specific function, such as steering wire lumens, device working channel, optic channel, fluid or air infusion channel, or section channel, etc. Each tube is preferably separately constructed with materials specifically selected to maximize performance, lubricity, flexibility, and/or other desirable characteristics. When assembled, one or more steering wires 4774 are routed through a corresponding number of steering tubes 4776 of the catheter. The steering wires 4774 may be connected to the distal end of the catheter via adhesive, heat bonding, crimping, or other known techniques. In one embodiment, the steering wires may be attached to a radio opaque marker band 4780 for use in fluoroscopy.

Figure 48:
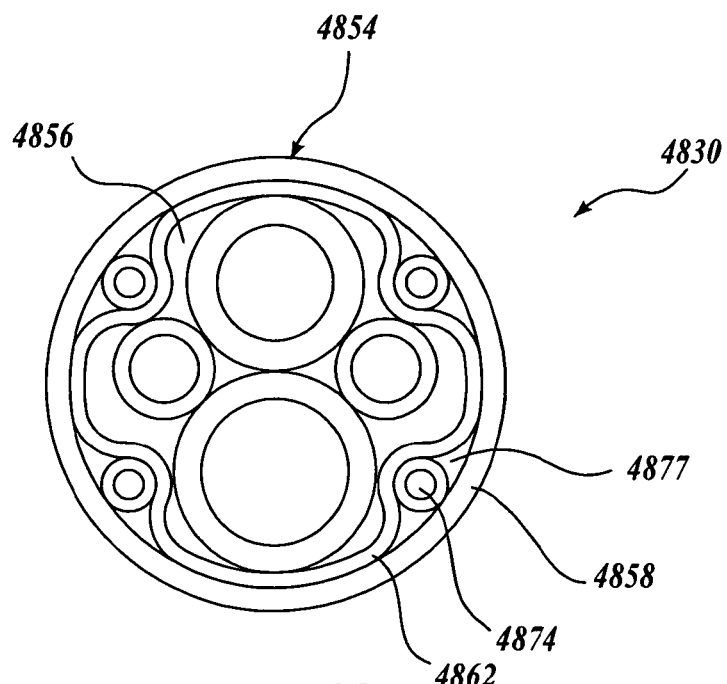
FIG. 48 is an end view of another embodiment of a catheter formed in accordance with the present invention.

Alternatively, as best shown in FIG. 48, a catheter 4830 may be formed from a steering sheath 4854, such as a steering guide catheter of appropriate dimensions, by filling the central longitudinal lumen 4856 with a bundle of tubes. The steering sheath 4854 typically includes an outer sleeve or jacket 4858 with an internal sleeve or liner 4862. The steering wires 4874 typically run along the inner surface of the catheter to the distal end and are located within channels 4877 defined by the internal sleeve or liner 4862. The liner preferably has a low coefficient of friction to facilitate the passage of wires, and may be formed from a polymer containing PTFE or PTFE impregnated thermoplastic elastomers, or may be constructed of thermoplastic materials, such as polyamides, polyurethane, polyethylene, and block copolymers thereof.

The principles, preferred embodiments, and modes of operation of the present invention have been described in the foregoing description. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes, and equivalents which fall within the spirit and scope of the present invention.

The embodiments of the invention in which an exclusive property or privilege is claimed are defined as follows:

1. A medical visualization system, comprising:
  an endoscope having an endoscope insertion tube extending distally from an endoscope handle, the endoscope handle having a longitudinal axis and an access port for accessing an interior lumen of the insertion tube, the endoscope including an imaging device for viewing objects located at the distal end of the insertion tube;
  a catheter assembly comprising a catheter extending distally from a catheter handle, the catheter handle having a longitudinal axis and an access port for accessing an interior lumen of the catheter, wherein the catheter may be inserted into the endoscope access port and routed through a portion of the insertion tube interior lumen; and
  an optical assembly comprising an image transmission member having distal and proximal ends, wherein the image transmission member is configured for insertion into the catheter access port and routable through a portion of the catheter interior lumen during use, the optical assembly being capable of obtaining images located at the distal end of the catheter and transmitting the images to the proximal end of the member, wherein the catheter handle includes an endoscope attachment device configured to selectively mount a proximal end of the catheter handle to the endoscope handle, wherein the endoscope access port is positioned distal of a proximal-most end of the endoscope, wherein the proximal end of the catheter handle is mounted to the endoscope handle at a mounting position distal of the endoscope access port; and wherein the catheter access port is positioned distal to the mounting position.

2. The system of claim 1, wherein the catheter assembly further comprises a second access port for accessing a second access lumen, and wherein the second access port is positioned proximal to the catheter access port.

3. The system of claim 2, wherein the catheter assembly further comprises a third access port for accessing a third access lumen.

4. The system of claim 3, wherein the third access lumen is configured as an irrigation and/or insufflation lumen.

5. The system of claim 2, wherein the second access lumen is configured to contain a guidewire.

6. The system of claim 1, wherein the catheter extends from the catheter handle at a first position, and the catheter is inserted into the endoscope access port at a second position, and wherein the first position is distal to the second position.

7. The system of claim 1, wherein when the catheter handle is mounted to the endoscope handle and the catheter is inserted into the endoscope access port, the catheter creates a loop.

8. The system of claim 1, wherein the catheter comprises a distal portion furthest from the catheter handle, a proximal portion connected to the catheter handle, and a middle portion connecting the distal portion to the proximal portion, wherein the distal portion of the catheter is distal to both the middle portion of the catheter and the proximal portion of the catheter when the catheter handle is mounted to the endoscope handle and the catheter is inserted into the endoscope access port, and wherein the proximal portion of the catheter is distal to the middle portion of the catheter when the catheter handle is mounted to the endoscope handle and the catheter is inserted into the endoscope access port.

9. The system of claim 1, wherein the optical assembly is configured such that a distal-most end of the image transmission member is prevented from extending past a distal-most end of the catheter.

10. The system of claim 1, wherein a distal end of the optical assembly and a distal end of the catheter are configured so as to prevent rotation of the distal end of the optical assembly with respect to the distal end of the catheter when engaged.

11. The system of claim 1, wherein the endoscope attachment device includes an adjustable strap configured to selectively mount the proximal end of the catheter handle to the endoscope handle, wherein the adjustable strap is configured to receive a housing projection.

12. The system of claim 11, wherein the adjustable strap further comprises at least two adjustment notches, and wherein each of the at least two adjustment notches is configured to receive the housing projection.

13. The system of claim 11, wherein the adjustable strap is configured to permit the catheter handle to rotate around the endoscope when the catheter handle is mounted to the endoscope handle.

14. The system of claim 1, wherein the optical assembly further includes an image viewing device permanently or detachably connected to the proximal end of the image transmission member, the image viewing device capable of viewing images transmitted thereto via the member.

15. The system of claim 1, wherein the catheter assembly is disposable.

16. The system of claim 1, wherein the image transmission member includes an indicator that indicates the orientation of the catheter assembly or the image transmission member when inserted into the catheter interior lumen.

17. The system of claim 1, wherein the image transmission member is a cable.

* * * * *